United States Patent
Fung et al.

(10) Patent No.: US 9,936,956 B2
(45) Date of Patent: Apr. 10, 2018

(54) DEVICES AND METHODS FOR LEFT ATRIAL APPENDAGE CLOSURE

(71) Applicant: SentreHEART, Inc., Redwood City, CA (US)

(72) Inventors: Gregory W. Fung, Redwood Shores, CA (US); Alan L. Bradley, San Francisco, CA (US); Robert L. Clark, III, Hayward, CA (US); Russell Pong, Newark, CA (US); Russell A. Seiber, Cullowhee, NC (US)

(73) Assignee: SentreHEART, Inc., Redwood City, CA (US)

( * ) Notice: Subject to any disclaimer, the term of this patent is extended or adjusted under 35 U.S.C. 154(b) by 132 days.

(21) Appl. No.: 15/080,410

(22) Filed: Mar. 24, 2016

(65) Prior Publication Data

US 2016/0278781 A1 Sep. 29, 2016

Related U.S. Application Data

(60) Provisional application No. 62/137,738, filed on Mar. 24, 2015.

(51) Int. Cl.
*A61B 17/04* (2006.01)
*A61B 17/12* (2006.01)
(Continued)

(52) U.S. Cl.
CPC ...... *A61B 17/12013* (2013.01); *A61B 90/361* (2016.02); *A61B 2017/00243* (2013.01);
(Continued)

(58) Field of Classification Search
CPC .............. A61B 17/32056; A61B 17/12; A61B 17/12009; A61B 17/12018;
(Continued)

(56) References Cited

U.S. PATENT DOCUMENTS 3,496,932 A  2/1970  Prisk et al.
3,677,597 A  7/1972  Stipek
(Continued)

FOREIGN PATENT DOCUMENTS

CN  101262823 B  12/2011
EP  0 598 219 A2  5/1994
(Continued)

OTHER PUBLICATIONS

Notice of Allowance dated Apr. 11, 2016, for U.S. Appl. No. 14/195,797, filed Mar. 3, 2014; 14 pages.
(Continued)

*Primary Examiner* — Melanie Tyson
(74) *Attorney, Agent, or Firm* — Cooley LLP

(57) ABSTRACT

Surgical and percutaneous devices for closing tissue, for example, the left atrial appendage, may have an elongate body with a stiffened proximal portion, a flexible middle portion, a distal portion, a closure element with a loop having a continuous aperture therethrough, and a suture loop. The closure devices may have a malleable member attached to the elongate body that may be configured to retain a curve after a force is applied to the malleable member. System and methods for closing the left atrial appendage may utilize a closure device and a curved guide device, and the closure device and curved guide device may be self-orienting.

15 Claims, 30 Drawing Sheets

(51) Int. Cl.
  *A61B 90/00* (2016.01)
  *A61B 17/00* (2006.01)
(52) U.S. Cl.
  CPC .............. *A61B 2017/00309* (2013.01); *A61B 2017/00358* (2013.01)
(58) Field of Classification Search
  CPC ............ A61B 17/12013; A61B 17/128; A61B 17/1285; A61B 17/0469; A61B 2017/12018; A61B 2017/00243; A61B 2017/003; A61B 2017/00305; A61B 2017/00309; A61B 2017/00358
  USPC .......................... 606/113, 139, 140–142, 144
  See application file for complete search history.

(56) References Cited

U.S. PATENT DOCUMENTS

| | | |
|---|---|---|
| 3,802,074 A | 4/1974 | Hoppe |
| 3,841,685 A | 10/1974 | Kolodziej |
| 3,999,555 A | 12/1976 | Person |
| 4,018,229 A | 4/1977 | Komiya |
| 4,030,509 A | 6/1977 | Heilman et al. |
| 4,078,305 A | 3/1978 | Akiyama |
| 4,181,123 A | 1/1980 | Crosby |
| 4,249,536 A | 2/1981 | Vega |
| 4,257,278 A | 3/1981 | Papadofrangakis et al. |
| 4,319,562 A | 3/1982 | Crosby |
| 4,428,375 A | 1/1984 | Ellman |
| 4,596,530 A | 6/1986 | McGlinn |
| 4,662,377 A | 5/1987 | Heilman et al. |
| 4,765,341 A | 8/1988 | Mower et al. |
| 4,817,608 A | 4/1989 | Shapland et al. |
| 4,901,405 A | 2/1990 | Grover et al. |
| 4,944,753 A | 7/1990 | Burgess et al. |
| 4,991,578 A | 2/1991 | Cohen |
| 4,991,603 A | 2/1991 | Cohen et al. |
| 4,998,975 A | 3/1991 | Cohen et al. |
| 5,033,477 A | 7/1991 | Chin et al. |
| 5,108,406 A | 4/1992 | Lee |
| 5,163,942 A | 11/1992 | Rydell |
| 5,163,946 A | 11/1992 | Li |
| 5,176,691 A | 1/1993 | Pierce |
| 5,181,123 A | 1/1993 | Swank |
| 5,226,535 A | 7/1993 | Roshdy et al. |
| 5,226,908 A | 7/1993 | Yoon |
| 5,242,459 A | 9/1993 | Buelna |
| 5,243,977 A | 9/1993 | Trabucco et al. |
| 5,269,326 A | 12/1993 | Verrier |
| 5,279,539 A | 1/1994 | Bohan et al. |
| 5,281,238 A | 1/1994 | Chin et al. |
| 5,300,078 A | 4/1994 | Buelna |
| 5,306,234 A | 4/1994 | Johnson |
| 5,318,578 A | 6/1994 | Hasson |
| 5,336,229 A | 8/1994 | Noda |
| 5,336,231 A | 8/1994 | Adair |
| 5,336,252 A | 8/1994 | Cohen |
| 5,385,156 A | 1/1995 | Oliva |
| 5,387,219 A | 2/1995 | Rappe |
| 5,398,944 A | 3/1995 | Holster |
| 5,403,331 A | 4/1995 | Chesterfield et al. |
| 5,405,351 A | 4/1995 | Kinet et al. |
| 5,417,684 A | 5/1995 | Jackson et al. |
| 5,423,821 A | 6/1995 | Pasque |
| 5,423,830 A | 6/1995 | Schneebaum et al. |
| 5,433,457 A | 7/1995 | Wright |
| 5,433,730 A | 7/1995 | Alt |
| 5,443,481 A | 8/1995 | Lee |
| 5,449,361 A | 9/1995 | Preissman |
| 5,449,637 A | 9/1995 | Kadry |
| 5,465,731 A | 11/1995 | Bell et al. |
| 5,494,240 A | 2/1996 | Waugh |
| 5,498,228 A | 3/1996 | Royalty et al. |
| 5,522,819 A * | 6/1996 | Graves .................. A61B 17/221 606/110 |
| 5,540,711 A | 7/1996 | Kieturakis et al. |
| 5,545,178 A | 8/1996 | Kensey et al. |
| 5,571,161 A | 11/1996 | Starksen |
| 5,591,177 A | 1/1997 | Lehrer |
| 5,609,597 A | 3/1997 | Lehrer |
| 5,624,430 A | 4/1997 | Eton et al. |
| 5,624,453 A | 4/1997 | Ahmed |
| 5,634,895 A | 6/1997 | Igo et al. |
| 5,636,780 A | 6/1997 | Green et al. |
| 5,676,162 A | 10/1997 | Larson, Jr. et al. |
| 5,676,651 A | 10/1997 | Larson, Jr. et al. |
| 5,678,547 A | 10/1997 | Faupel et al. |
| 5,681,278 A | 10/1997 | Igo et al. |
| 5,682,906 A | 11/1997 | Sterman et al. |
| 5,683,348 A | 11/1997 | Diener |
| 5,683,364 A | 11/1997 | Zadini et al. |
| 5,683,445 A | 11/1997 | Swoyer |
| 5,693,059 A | 12/1997 | Yoon |
| 5,693,091 A | 12/1997 | Larson, Jr. et al. |
| 5,699,748 A | 12/1997 | Linskey, Jr. et al. |
| 5,702,430 A | 12/1997 | Larson, Jr. et al. |
| 5,707,336 A | 1/1998 | Rubin |
| 5,716,367 A | 2/1998 | Koike et al. |
| 5,716,392 A | 2/1998 | Bourgeois et al. |
| 5,727,569 A | 3/1998 | Benetti et al. |
| 5,728,151 A | 3/1998 | Garrison et al. |
| 5,735,877 A | 4/1998 | Pagedas |
| 5,741,281 A | 4/1998 | Martin |
| 5,752,526 A | 5/1998 | Cosgrove |
| 5,766,151 A | 6/1998 | Valley et al. |
| 5,766,216 A | 6/1998 | Gangal et al. |
| 5,766,217 A | 6/1998 | Christy |
| 5,769,863 A | 6/1998 | Garrison |
| 5,779,727 A | 7/1998 | Orejola |
| 5,788,715 A | 8/1998 | Watson, Jr. et al. |
| 5,792,151 A | 8/1998 | Heck et al. |
| 5,797,870 A | 8/1998 | March et al. |
| 5,797,929 A | 8/1998 | Andreas et al. |
| 5,797,946 A | 8/1998 | Chin |
| 5,799,661 A | 9/1998 | Boyd et al. |
| 5,810,845 A | 9/1998 | Yoon |
| 5,814,052 A | 9/1998 | Nakao et al. |
| 5,823,946 A | 10/1998 | Chin |
| 5,827,216 A | 10/1998 | Igo et al. |
| 5,840,059 A | 11/1998 | March et al. |
| 5,855,586 A | 1/1999 | Habara et al. |
| 5,865,791 A | 2/1999 | Whayne et al. |
| 5,871,531 A | 2/1999 | Struble |
| 5,873,876 A | 2/1999 | Christy |
| 5,879,375 A | 3/1999 | Larson, Jr. et al. |
| 5,882,299 A | 3/1999 | Rastegar et al. |
| 5,893,869 A | 4/1999 | Barnhart et al. |
| 5,895,298 A | 4/1999 | Faupel et al. |
| 5,897,586 A | 4/1999 | Molina |
| 5,900,433 A | 5/1999 | Igo et al. |
| 5,906,579 A | 5/1999 | Vander Salm et al. |
| 5,906,620 A | 5/1999 | Nakao et al. |
| 5,908,429 A | 6/1999 | Yoon |
| 5,908,435 A | 6/1999 | Samuels |
| 5,910,124 A | 6/1999 | Rubin |
| 5,910,129 A | 6/1999 | Koblish et al. |
| 5,921,994 A | 7/1999 | Andreas et al. |
| 5,924,424 A | 7/1999 | Stevens et al. |
| RE36,269 E | 8/1999 | Wright |
| 5,941,819 A | 8/1999 | Chin |
| 5,957,936 A | 9/1999 | Yoon et al. |
| 5,961,440 A | 10/1999 | Schweich, Jr. et al. |
| 5,964,699 A | 10/1999 | Rullo et al. |
| 5,968,010 A | 10/1999 | Waxman et al. |
| 5,972,013 A | 10/1999 | Schmidt |
| 5,984,866 A | 11/1999 | Rullo et al. |
| 5,984,917 A | 11/1999 | Fleischman et al. |
| 5,991,668 A | 11/1999 | Leinders et al. |
| 5,997,525 A | 12/1999 | March et al. |
| 6,006,122 A | 12/1999 | Smits |
| 6,010,531 A | 1/2000 | Donlon et al. |
| 6,015,382 A | 1/2000 | Zwart et al. |
| 6,045,570 A | 4/2000 | Epstein et al. |
| 6,048,329 A | 4/2000 | Thompson et al. |

(56) References Cited

U.S. PATENT DOCUMENTS

| | | |
|---|---|---|
| 6,059,750 A | 5/2000 | Fogarty et al. |
| 6,067,942 A | 5/2000 | Fernandez |
| 6,071,281 A | 6/2000 | Burnside et al. |
| 6,081,738 A | 6/2000 | Hinohara et al. |
| 6,083,153 A | 7/2000 | Rullo et al. |
| 6,090,042 A | 7/2000 | Rullo et al. |
| 6,095,968 A | 8/2000 | Snyders |
| 6,110,170 A | 8/2000 | Taylor et al. |
| 6,120,431 A | 9/2000 | Magovern et al. |
| 6,132,438 A | 10/2000 | Fleischman et al. |
| 6,148,230 A | 11/2000 | KenKnight |
| 6,149,595 A | 11/2000 | Seitz et al. |
| 6,152,144 A | 11/2000 | Lesh et al. |
| 6,152,920 A | 11/2000 | Thompson et al. |
| 6,152,936 A | 11/2000 | Christy et al. |
| 6,155,968 A | 12/2000 | Wilk |
| 6,157,852 A | 12/2000 | Selmon et al. |
| 6,161,543 A | 12/2000 | Cox et al. |
| 6,162,195 A | 12/2000 | Igo et al. |
| 6,167,889 B1 | 1/2001 | Benetti |
| 6,199,556 B1 | 3/2001 | Benetti et al. |
| 6,200,303 B1 | 3/2001 | Verrior et al. |
| 6,206,004 B1 | 3/2001 | Schmidt et al. |
| 6,224,584 B1 | 5/2001 | March et al. |
| 6,231,518 B1 | 5/2001 | Grabek et al. |
| 6,237,605 B1 | 5/2001 | Vaska et al. |
| 6,241,667 B1 | 6/2001 | Vetter et al. |
| 6,258,021 B1 | 7/2001 | Wilk |
| 6,266,550 B1 | 7/2001 | Selmon et al. |
| 6,280,415 B1 | 8/2001 | Johnson |
| 6,283,127 B1 | 9/2001 | Sterman et al. |
| 6,290,674 B1 | 9/2001 | Roue et al. |
| 6,293,906 B1 | 9/2001 | Vanden Hoek et al. |
| 6,296,630 B1 | 10/2001 | Altman et al. |
| 6,311,692 B1 | 11/2001 | Vaska et al. |
| 6,311,693 B1 | 11/2001 | Sterman et al. |
| 6,314,962 B1 | 11/2001 | Vaska et al. |
| 6,314,963 B1 | 11/2001 | Vaska et al. |
| 6,319,201 B1 | 11/2001 | Wilk |
| 6,333,347 B1 | 12/2001 | Hunter et al. |
| 6,346,074 B1 | 2/2002 | Roth |
| 6,379,366 B1 | 4/2002 | Fleischman et al. |
| 6,423,051 B1 | 7/2002 | Kaplan et al. |
| 6,474,340 B1 | 11/2002 | Vaska et al. |
| 6,485,407 B2 | 11/2002 | Alferness et al. |
| 6,488,689 B1 | 12/2002 | Kaplan et al. |
| 6,494,211 B1 | 12/2002 | Boyd et al. |
| 6,551,303 B1 | 4/2003 | Van Tassel et al. |
| 6,561,969 B2 | 5/2003 | Frazier et al. |
| 6,592,552 B1 | 7/2003 | Schmidt |
| 6,610,055 B1 | 8/2003 | Swanson et al. |
| 6,610,072 B1 | 8/2003 | Christy et al. |
| 6,613,062 B1 | 9/2003 | Leckrone et al. |
| 6,632,229 B1 | 10/2003 | Yamanouchi |
| 6,652,555 B1 | 11/2003 | VanTassel et al. |
| 6,656,175 B2 | 12/2003 | Francischelli et al. |
| 6,666,861 B1 | 12/2003 | Grabek |
| 6,692,491 B1 | 2/2004 | Phan |
| 6,733,509 B2 | 5/2004 | Nobles et al. |
| 6,736,774 B2 | 5/2004 | Benetti et al. |
| 6,755,338 B2 | 6/2004 | Hahnen et al. |
| 6,786,898 B2 | 9/2004 | Guenst |
| 6,789,509 B1 | 9/2004 | Motsinger |
| 6,830,174 B2 | 12/2004 | Hillstead et al. |
| 6,830,576 B2 | 12/2004 | Fleischman et al. |
| 6,985,776 B2 | 1/2006 | Kane et al. |
| 7,011,671 B2 | 3/2006 | Welch |
| 7,041,111 B2 | 5/2006 | Chu |
| 7,056,294 B2 | 6/2006 | Khairkhahan et al. |
| 7,063,682 B1 | 6/2006 | Whayne et al. |
| 7,063,693 B2 | 6/2006 | Guenst |
| 7,175,619 B2 | 2/2007 | Koblish et al. |
| 7,186,214 B2 | 3/2007 | Ness |
| 7,207,988 B2 | 4/2007 | Leckrone et al. |
| 7,226,440 B2 | 6/2007 | Gelfand et al. |
| 7,226,458 B2 | 6/2007 | Kaplan et al. |
| 7,264,587 B2 | 9/2007 | Chin |
| 7,294,115 B1 | 11/2007 | Wilk |
| 7,297,144 B2 | 11/2007 | Fleischman et al. |
| 7,309,328 B2 | 12/2007 | Kaplan et al. |
| 7,318,829 B2 | 1/2008 | Kaplan et al. |
| 7,326,221 B2 | 2/2008 | Sakamoto et al. |
| 7,331,979 B2 | 2/2008 | Khosravi et al. |
| 7,473,260 B2 | 1/2009 | Opolski et al. |
| 7,608,091 B2 | 10/2009 | Goldfarb et al. |
| 7,610,104 B2 | 10/2009 | Kaplan et al. |
| 7,618,425 B2 | 11/2009 | Yamamoto et al. |
| 7,722,641 B2 | 5/2010 | van der Burg et al. |
| 7,736,347 B2 | 6/2010 | Kaplan et al. |
| 7,828,810 B2 | 11/2010 | Liddicoat et al. |
| 7,846,168 B2 | 12/2010 | Liddicoat et al. |
| 7,905,900 B2 | 3/2011 | Palermo et al. |
| 7,918,865 B2 | 4/2011 | Liddicoat et al. |
| 7,967,808 B2 | 6/2011 | Fitzgerald et al. |
| 8,105,342 B2 | 1/2012 | Onuki et al. |
| 8,157,818 B2 | 4/2012 | Gartner et al. |
| 8,287,561 B2 | 10/2012 | Nunez et al. |
| 8,469,983 B2 | 6/2013 | Fung et al. |
| 8,636,767 B2 | 1/2014 | McClain |
| 8,715,302 B2 | 5/2014 | Ibrahim et al. |
| 8,721,663 B2 | 5/2014 | Kaplan et al. |
| 8,771,297 B2 | 7/2014 | Miller et al. |
| 8,795,297 B2 | 8/2014 | Liddicoat et al. |
| 8,795,310 B2 | 8/2014 | Fung et al. |
| 8,814,778 B2 | 8/2014 | Kiser et al. |
| 8,932,276 B1 | 1/2015 | Morriss et al. |
| 8,961,543 B2 | 2/2015 | Friedman et al. |
| 8,974,473 B2 | 3/2015 | Kaplan et al. |
| 8,986,278 B2 | 3/2015 | Fung et al. |
| 8,986,325 B2 | 3/2015 | Miller et al. |
| 8,996,133 B2 | 3/2015 | Kaplan et al. |
| 9,089,324 B2 | 7/2015 | McCaw et al. |
| 9,186,174 B2 | 11/2015 | Krishnan et al. |
| 9,198,664 B2 | 12/2015 | Fung et al. |
| 9,198,683 B2 | 12/2015 | Friedman et al. |
| 9,271,819 B2 | 3/2016 | Liddicoat et al. |
| 9,339,295 B2 | 5/2016 | Fung et al. |
| 9,498,223 B2 | 11/2016 | Miller et al. |
| 2001/0025132 A1 | 9/2001 | Alferness et al. |
| 2002/0017306 A1 | 2/2002 | Cox et al. |
| 2002/0022860 A1 | 2/2002 | Borillo et al. |
| 2002/0049457 A1 | 4/2002 | Kaplan et al. |
| 2002/0058925 A1 | 5/2002 | Kaplan et al. |
| 2002/0062136 A1 | 5/2002 | Hillstead et al. |
| 2002/0068970 A1 | 6/2002 | Cox et al. |
| 2002/0099390 A1 | 7/2002 | Kaplan et al. |
| 2002/0103492 A1 | 8/2002 | Kaplan et al. |
| 2002/0107531 A1 | 8/2002 | Schreck et al. |
| 2002/0111636 A1 | 8/2002 | Fleischman et al. |
| 2002/0111637 A1 | 8/2002 | Kaplan et al. |
| 2002/0147456 A1 | 10/2002 | Diduch et al. |
| 2003/0014049 A1 | 1/2003 | Koblish et al. |
| 2003/0024537 A1 | 2/2003 | Cox et al. |
| 2003/0045900 A1 | 3/2003 | Hahnen et al. |
| 2003/0069577 A1 | 4/2003 | Vaska et al. |
| 2003/0083542 A1 | 5/2003 | Alferness et al. |
| 2003/0083674 A1 | 5/2003 | Gibbens, III |
| 2003/0109863 A1 | 6/2003 | Francischelli et al. |
| 2003/0120264 A1 | 6/2003 | Lattouf |
| 2003/0158464 A1 | 8/2003 | Bertolero |
| 2003/0181942 A1 | 9/2003 | Sutton et al. |
| 2003/0187460 A1 | 10/2003 | Chin et al. |
| 2003/0236535 A1 | 12/2003 | Onuki et al. |
| 2004/0030335 A1 | 2/2004 | Zenati et al. |
| 2004/0034347 A1 | 2/2004 | Hall et al. |
| 2004/0044361 A1 | 3/2004 | Frazier et al. |
| 2004/0049210 A1 | 3/2004 | VanTassel et al. |
| 2004/0059352 A1 | 3/2004 | Burbank et al. |
| 2004/0064138 A1 | 4/2004 | Grabek |
| 2004/0068267 A1 | 4/2004 | Harvie et al. |
| 2004/0078069 A1 | 4/2004 | Francischelli et al. |
| 2004/0102804 A1 | 5/2004 | Chin |
| 2004/0106918 A1 | 6/2004 | Cox et al. |
| 2004/0111101 A1 | 6/2004 | Chin |

(56) References Cited

U.S. PATENT DOCUMENTS

| | | |
|---|---|---|
| 2004/0116943 A1 | 6/2004 | Brandt et al. |
| 2004/0158127 A1 | 8/2004 | Okada |
| 2004/0162579 A1 | 8/2004 | Foerster |
| 2004/0225212 A1 | 11/2004 | Okerlund et al. |
| 2004/0225300 A1 | 11/2004 | Goldfarb et al. |
| 2004/0243176 A1 | 12/2004 | Hahnen et al. |
| 2004/0260273 A1 | 12/2004 | Wan |
| 2005/0033280 A1 | 2/2005 | Francischelli et al. |
| 2005/0033287 A1 | 2/2005 | Sra |
| 2005/0033321 A1 | 2/2005 | Fleischman et al. |
| 2005/0043743 A1 | 2/2005 | Dennis |
| 2005/0043745 A1 | 2/2005 | Alferness et al. |
| 2005/0080454 A1 | 4/2005 | Drews et al. |
| 2005/0085843 A1 | 4/2005 | Opolski et al. |
| 2005/0107824 A1 | 5/2005 | Hillstead et al. |
| 2005/0149068 A1 | 7/2005 | Williams et al. |
| 2005/0149069 A1 | 7/2005 | Bertolero et al. |
| 2005/0154376 A1 | 7/2005 | Riviere et al. |
| 2005/0165466 A1 | 7/2005 | Morris et al. |
| 2005/0256532 A1 | 11/2005 | Nayak et al. |
| 2006/0004323 A1 | 1/2006 | Chang et al. |
| 2006/0004388 A1 | 1/2006 | Whayne et al. |
| 2006/0009715 A1 | 1/2006 | Khairkhahan et al. |
| 2006/0020162 A1 | 1/2006 | Whayne et al. |
| 2006/0020271 A1 | 1/2006 | Stewart et al. |
| 2006/0020336 A1 | 1/2006 | Liddicoat |
| 2006/0034930 A1 | 2/2006 | Khosravi et al. |
| 2006/0095066 A1* | 5/2006 | Chang ............... A61B 17/1204 606/199 |
| 2006/0100545 A1 | 5/2006 | Ayala et al. |
| 2006/0200169 A1 | 9/2006 | Sniffin |
| 2006/0212045 A1 | 9/2006 | Schilling et al. |
| 2006/0247672 A1 | 11/2006 | Vidlund et al. |
| 2006/0253128 A1 | 11/2006 | Sekine et al. |
| 2007/0010829 A1 | 1/2007 | Nobles et al. |
| 2007/0016228 A1 | 1/2007 | Salas |
| 2007/0027456 A1 | 2/2007 | Gartner et al. |
| 2007/0038229 A1 | 2/2007 | de la Torre |
| 2007/0060951 A1 | 3/2007 | Shannon |
| 2007/0083082 A1 | 4/2007 | Kiser et al. |
| 2007/0083225 A1 | 4/2007 | Kiser et al. |
| 2007/0083232 A1 | 4/2007 | Lee |
| 2007/0088369 A1 | 4/2007 | Shaw et al. |
| 2007/0100405 A1 | 5/2007 | Thompson et al. |
| 2007/0135822 A1 | 6/2007 | Onuki et al. |
| 2007/0149988 A1 | 6/2007 | Michler et al. |
| 2007/0179345 A1 | 8/2007 | Santilli |
| 2007/0249991 A1 | 10/2007 | Whayne et al. |
| 2007/0260278 A1 | 11/2007 | Wheeler et al. |
| 2007/0270637 A1 | 11/2007 | Takemoto et al. |
| 2007/0270891 A1 | 11/2007 | McGuckin, Jr. |
| 2008/0009843 A1 | 1/2008 | de la Torre |
| 2008/0015406 A1 | 1/2008 | Dlugos et al. |
| 2008/0033241 A1 | 2/2008 | Peh et al. |
| 2008/0033457 A1 | 2/2008 | Francischelli et al. |
| 2008/0039879 A1 | 2/2008 | Chin et al. |
| 2008/0097489 A1 | 4/2008 | Goldfarb et al. |
| 2008/0154260 A1 | 6/2008 | Hoof |
| 2008/0214889 A1 | 9/2008 | Saadat et al. |
| 2008/0228265 A1 | 9/2008 | Spence et al. |
| 2008/0245371 A1 | 10/2008 | Gruber |
| 2008/0269782 A1 | 10/2008 | Stefanchik et al. |
| 2008/0294174 A1 | 11/2008 | Bardsley et al. |
| 2008/0294175 A1 | 11/2008 | Bardsley et al. |
| 2008/0312664 A1 | 12/2008 | Bardsley et al. |
| 2009/0043317 A1 | 2/2009 | Cavanaugh et al. |
| 2009/0088728 A1* | 4/2009 | Dollar ............... A61M 25/0041 604/528 |
| 2009/0088778 A1 | 4/2009 | Miyamoto et al. |
| 2009/0157118 A1 | 6/2009 | Miller et al. |
| 2009/0182326 A1 | 7/2009 | Zenati et al. |
| 2009/0196696 A1 | 8/2009 | Otsuka et al. |
| 2010/0069925 A1 | 3/2010 | Friedman et al. |
| 2010/0094314 A1 | 4/2010 | Hernlund |
| 2010/0174296 A1 | 7/2010 | Vakharia et al. |
| 2010/0191253 A1 | 7/2010 | Oostman et al. |
| 2010/0331820 A1 | 12/2010 | Giuseppe et al. |
| 2011/0034804 A1* | 2/2011 | Hubregtse ........ A61B 17/00234 600/433 |
| 2011/0060350 A1 | 3/2011 | Powers et al. |
| 2011/0087270 A1 | 4/2011 | Penner et al. |
| 2011/0092997 A1 | 4/2011 | Kang |
| 2011/0106107 A1 | 5/2011 | Binmoeller et al. |
| 2011/0112537 A1 | 5/2011 | Bernstein et al. |
| 2011/0144660 A1 | 6/2011 | Liddicoat et al. |
| 2011/0276075 A1 | 11/2011 | Fung et al. |
| 2011/0282250 A1 | 11/2011 | Fung et al. |
| 2011/0295060 A1 | 12/2011 | Zenati et al. |
| 2012/0022558 A1 | 1/2012 | Friedman et al. |
| 2012/0158022 A1 | 6/2012 | Kaplan et al. |
| 2012/0209300 A1 | 8/2012 | Torrie |
| 2012/0330351 A1 | 12/2012 | Friedman et al. |
| 2013/0144311 A1* | 6/2013 | Fung ................. A61B 17/12013 606/139 |
| 2014/0018831 A1 | 1/2014 | Kassab et al. |
| 2014/0171733 A1 | 6/2014 | Sternik |
| 2014/0222138 A1 | 8/2014 | Machold et al. |
| 2014/0276911 A1 | 9/2014 | Smith et al. |
| 2014/0276985 A1 | 9/2014 | Clark et al. |
| 2014/0303721 A1 | 10/2014 | Fung et al. |
| 2014/0330074 A1* | 11/2014 | Morriss .............. A61B 17/1657 600/104 |
| 2014/0336572 A1 | 11/2014 | Heisel et al. |
| 2014/0336676 A1 | 11/2014 | Pong et al. |
| 2014/0364901 A1 | 12/2014 | Kiser et al. |
| 2014/0364907 A1 | 12/2014 | White et al. |
| 2015/0018853 A1 | 1/2015 | Friedman et al. |
| 2015/0025312 A1 | 1/2015 | de Canniere |
| 2015/0173765 A1 | 1/2015 | Friedman et al. |
| 2015/0119884 A1 | 4/2015 | Fung et al. |
| 2015/0157328 A1 | 6/2015 | Miller et al. |
| 2015/0182225 A1 | 7/2015 | Morejohn et al. |
| 2015/0190135 A1 | 7/2015 | Ibrahim et al. |
| 2015/0223813 A1 | 8/2015 | Williamson et al. |
| 2015/0250482 A1 | 9/2015 | Slaughter et al. |
| 2015/0272618 A1 | 10/2015 | Fung et al. |
| 2015/0374380 A1 | 12/2015 | Miller et al. |
| 2016/0008001 A1 | 1/2016 | Winkler et al. |
| 2016/0008061 A1 | 1/2016 | Fung et al. |
| 2016/0106421 A1 | 4/2016 | Eliachar et al. |
| 2016/0120549 A1 | 5/2016 | Fung et al. |
| 2016/0302793 A1 | 10/2016 | Fung et al. |
| 2016/0310144 A1 | 10/2016 | Kimura et al. |
| 2016/0317155 A1 | 11/2016 | Kimura et al. |
| 2016/0346028 A1 | 12/2016 | Rogers et al. |
| 2017/0290592 A1 | 10/2017 | Miller et al. |
| 2018/0008342 A1 | 1/2018 | Ibrahim et al. |

FOREIGN PATENT DOCUMENTS

| | | |
|---|---|---|
| EP | 0 598 219 A3 | 5/1994 |
| EP | 0 598 219 B1 | 5/1994 |
| EP | 0625336 A2 | 11/1994 |
| EP | 1 010 397 A | 6/2000 |
| GB | 1 506 142 A | 4/1978 |
| JP | 6-319742 | 11/1994 |
| JP | 7-296645 A2 | 11/1995 |
| JP | 7-299073 A | 11/1995 |
| JP | 11-507262 A | 6/1999 |
| JP | 2001-120560 A | 5/2001 |
| JP | 2002-512071 A | 4/2002 |
| JP | 2002-540834 A | 12/2002 |
| JP | 2002-540901 A | 12/2002 |
| JP | 2003-225241 A | 8/2003 |
| JP | 2004-601 A | 1/2004 |
| JP | 2005-110860 A | 4/2005 |
| JP | 2005-296645 A | 10/2005 |
| JP | 2005-531360 A | 10/2005 |
| JP | 2007-504886 A | 3/2007 |
| JP | 2010-523171 A | 7/2010 |
| JP | 2012-522596 A | 9/2012 |
| WO | WO-94/01045 A1 | 1/1994 |
| WO | WO-94/04079 A1 | 3/1994 |
| WO | WO-94/08514 A1 | 4/1994 |

(56) References Cited

FOREIGN PATENT DOCUMENTS

| | | |
|---|---|---|
| WO | WO-96/04854 A1 | 2/1996 |
| WO | WO-96/40356 A1 | 12/1996 |
| WO | WO-97/11644 A1 | 4/1997 |
| WO | WO-97/43957 A1 | 11/1997 |
| WO | WO-99/53845 A1 | 10/1999 |
| WO | WO-00/59383 A1 | 10/2000 |
| WO | WO-00/61202 A1 | 10/2000 |
| WO | WO-2004/002327 A1 | 1/2004 |
| WO | WO-2004/066828 A2 | 8/2004 |
| WO | WO-2004/066828 A3 | 8/2004 |
| WO | WO-2005/034767 A1 | 4/2005 |
| WO | WO-2005/034802 A2 | 4/2005 |
| WO | WO-2005/034802 A3 | 4/2005 |
| WO | WO-2006/096805 A1 | 9/2006 |
| WO | WO-2006/110734 A2 | 10/2006 |
| WO | WO-2006/115689 A1 | 11/2006 |
| WO | WO-2007/037516 A2 | 4/2007 |
| WO | WO-2007/056502 A1 | 5/2007 |
| WO | WO-2008/017080 A2 | 2/2008 |
| WO | WO-2008/017080 A3 | 2/2008 |
| WO | WO-2008/036408 A2 | 3/2008 |
| WO | WO-2008/036408 A3 | 3/2008 |
| WO | WO-2008/091612 A2 | 7/2008 |
| WO | WO-2008/091612 A3 | 7/2008 |
| WO | WO-2008/121278 A2 | 10/2008 |
| WO | WO-2009/039191 A2 | 3/2009 |
| WO | WO-2009/094237 A1 | 7/2009 |
| WO | WO-2010/006061 A2 | 1/2010 |
| WO | WO-2010/006061 A3 | 1/2010 |
| WO | WO-2010/048141 A2 | 4/2010 |
| WO | WO-2010/048141 A3 | 4/2010 |
| WO | WO-2010/115030 A1 | 10/2010 |
| WO | WO-2012/170652 A1 | 12/2012 |

OTHER PUBLICATIONS afibfacts.com (Date Unknown). "Cox-Maze III: The Gold Standard Treatment for Atrial Fibrillation: Developing a Surgical Option for Atrial Fibrillation," located at <http://www.afibfacts.com/Treatment_Options_for_Atrial_Fibrillation/Cox-Maze_III%_3a_The_Gold_Standard_Treatment_for_Atrial_Fibrillation>, last visited on Apr. 20, 2007, 4 pages.

Al-Saady, N.M. et al. (1999). "Left Atrial Appendage: Structure, Function, and Role in Thromboembolism," *Heart* 82:547-554.

Albers, G.W. (Jul. 11, 1994). "Atrial Fibrillation and Stroke: Three New Studies, Three Remaining Questions," *Arch Intern Med* 154:1443-1448.

Alonso, M. et al. (Mar. 4, 2003). "Complications With Femoral Access in Cardiac Catheterization. Impact of Previous Systematic Femoral Angiography and Hemostasis With VasoSeal-Es® Collagen Plug," *Rev. Esp. Cardiol.* 56(6):569-577.

Aronow, W.S. et al. (Apr. 2009). "Atrial Fibrillation: The New Epidemic of the Age-ing World," *Journal of Atrial Fibrillation* 1(6):337-361.

Babaliaros, V.C. et al. (Jun. 3, 2008). "Emerging Applications for Transseptal Left Heart Catheterization: Old Techniques for New Procedures," *Journal of the American College of Cardiology* 51(22):2116-2122.

Bath, P.M.W. et al. (2005). "Current Status of Stroke Prevention in Patients with Atrial Fibrillation," *European Heart Journal Supplements* 7(Supplement C):C12-C18.

Benjamin, B.A. et al. (1994). "Effect of Bilateral Atrial Appendectomy on Postprandial Sodium Excretion in Conscious Monkeys," *Society for Experimental Biology and Medicine* 2006: 1 page.

Beygui, F. et al. (2005, e-pub. Oct. 21, 2005). "Multimodality Imaging of Percutaneous Closure of the Left Atrial Appendage," *Clinical Vignette*, 1 page.

Bisleri, G. et al. (Jun. 3, 2005). "Innovative Monolateral Approach for Closed-Chest Atrial Fibrillation Surgery," *The Annals of Thoracic Surgery* 80:e22-e25.

Björk, V.O. et al. (Aug. 1961). "Sequelae of Left Ventricular Puncture with Angiocardiography," *Circulation* 24:204-212.

Blackshear, J.L. et al. (Feb. 1996). "Appendage Obliteration to Reduce Stroke in Cardiac Surgical Patients With Atrial Fibrillation," *Ann. Thorac. Surg.* 61(2), 13 pages.

Blackshear, J.L. et al. (Oct. 1, 2003). "Thorascopic Extracardiac Obliteration of the Left Atrial Appendage for Stroke Risk Reduction in Atrial Fibrillation," *J. Am. Coll. Cardiol.* 42(7):1249-1252.

Bonanomi, G. et al. (Jan. 1, 2003). "Left Atrial Appendectomy and Maze," *Journal of the American College of Cardiology* 41(1):169-171.

Bonow, R.O. et al. (1998). "Guidelines for the Management of Patients With Valvular Heart Disease: Executive Summary: A Report of the American College of Cardiology/American Heart Association Task Force on Practice Guidelines (Committee on Management of Patients With Valvular Heart Disease)," *Journal of the American Heart Association* 98:1949-1984.

Botham, R.J. et al. (May 1959). "Pericardial Tamponade Following Percutaneous Left Ventricular Puncture," *Circulation* 19:741-744.

Brock, R. et al. (1956). "Percutaneous Left Ventricular Puncture in the Assessment of Aortic Stenosis," *Thorax* 11:163-171.

Burke, R.P. et al. (1992). "Improved Surgical Approach to Left Atrial Appendage Aneurysm," *Journal of Cardiac Surgery* 7(2):104-107.

Canaccord Adams (Aug. 11, 2008). "A-Fib: Near a Tipping Point," 167 pages.

Chung, M.K. (Jul. 2003). "Current Clinical Issues in Atrial Fibrillation," *Cleveland Clinic Journal of Medicine* 70(Supp. 3):S6-S11.

Coffin, L.H. (Jun. 1985). "Use of the Surgical Stapler to Obliterate the Left Atrial Appendage," *Surgery, Gynecology & Obstetric* 160:565-566.

Connolly, S.J. (Sep. 7, 1999). "Preventing Stroke in Atrial Fibrillation: Why Are So Many Eligible Patients Not Receiving Anticoagulant Therapy?" *Canadian Medical Association* 161(5):533-534.

Costa, R. et al. (2006). "Bi-Atrial Subxiphoid Epicardial Pacemaker in Superior Vena Cava Syndrome," *Arq. Bras. Cardiol.* 87:e45-e47.

Cox, J.L. et al. (Apr. 1991). "The Surgical Treatment of Atrial Fibrillation: IV. Surgical Technique," *J. Thorac. Cardiovasc. Surg.* 101(4):584-592.

Cox, J.L. et al. (Aug. 1995). "Modification of the Maze Procedure for Atrial Flutter and Atrial Fibrillation I. Rationale and Surgical Results," *J. Thorac. Cardiovasc. Surg.* 110(2):473-484.

Cox, J.L. et al. (Aug. 1995). "Modification of the Maze Procedure for Atrial Flutter and Atrial Fibrillation II. Surgical Technique of the Maze III Procedure," *J. Thorac. Cardiovasc. Surg.* 110(2):485-495.

Cox, J.L. et al. (Nov. 1999). "Impact of the Maze Procedure on the Stroke Rate in Patients with Atrial Fibrillation," *J. Thorac. Cardiovasc. Surg.* 118:833-840.

Cox, J.L. et al. (2004). "The Role of Surgical Intervention in the Management of Atrial Fibrillation," *Texas Heart Institute Journal* 31(3):257-265.

Crystal, E. et al. (Jan. 2003). "Left Atrial Appendage Occlusion Study (LAAOS): A Randomized Clinical Trial of Left Atrial Appendage Occlusion During Routine Coronary Artery Bypass Graft Surgery for Long-term Stroke Prevention," *Am Heart J* 145(1):174-178.

D'Avila, A. et al. (Apr. 2003). "Pericardial Anatomy for the Interventional Electrophysiologist," *Journal of Cardiovascular Electrophysiology* 14(4):422-430.

D'Avila, A. et al. (Nov. 2007). "Experimental Efficacy of Pericardial Instillation of Anti-inflammatory Agents During Percutaneous Epicardial Catheter Ablation to Prevent Postprocedure Pericarditis," *Journal of Cardiovascular Electrophysiology* 18(11):1178-1183.

Demaria, A.N. et al. (Dec. 17, 2003). "Highlights of the Year JACC 2003," *Journal of the American College of Cardiology* 42(12):2156-2166.

Deneu, S. et al. (Jul. 11, 1999). "Catheter Entrapment by Atrial Suture During Minimally Invasive Port-access Cardiac Surgery," *Canadian Journal of Anesthesia* 46(10):983-986.

Deponti, R. et al. (Mar. 7, 2006). "Trans-Septal Catheterization in the Electrophysiology Laboratory: Data From a Multicenter Survey Spanning 12 Years," *Journal of the American College of Cardiology* 47(5):1037-1042.

(56) References Cited

OTHER PUBLICATIONS

Donal, E. et al. (Sep. 2005). "The Left Atrial Appendage, a Small, Blind-Ended Structure: A Review of Its Echocardiographic Evaluation and Its Clinical Role," *Chest* 128(3):1853-1862.

Donnino, R. et al. (2007). "Left Atrial Appendage Thrombus Outside of a 'Successful' Ligation," *European Journal of Echocardiography* pp. 1-2.

Dullum, M.K.C. et al. (1999). "Xyphoid MIDCAB: Report of the Technique and Experience with a Less Invasive Midcab Procedure," *Heart Surgery Forum* 2(1):77-81.

Feinberg, W.M. et al. (Mar. 13, 1995). "Prevalence, Age Distribution, and Gender of Patients With Atrial Fibrillation," *Arch Intern Med* 155:469-473.

Fieguth, H.G. et al. (1997). "Inhibition of Atrial Fibrillation by Pulmonary Vein Isolation and Auricular Resection—Experimental Study in a Sheep Model," *European Journal of Cardio-Thoracic Surgery* 11:714-721.

Fisher, D.C. et al. (Dec. 1998). "Large Gradient Across a Partially Ligated Left Atrial Appendage," *Journal of the American Society of Echocardiography* 11(12):1163-1165.

Friberg, L. et al. (2006). "Stroke Prophylaxis in Atrial Fibrillation: Who Gets it and Who Does Not?" *European Heart Journal* 27:1954-1964.

Friedman, P.A. et al. (Aug. 2009). "Percutaneous Epicardial Left Atrial Appendage Closure: Preliminary Results of an Electrogram Guided Approach," *Journal of Cardiovascular Electrophysiology* 20(8):908-915.

Fuster, V. et al. (Oct. 2001). "ACC/AHA/ESC Guidelines for the Management of Patients with Atrial Fibrillation," *European Heart Journal* 22(20):1852-1923.

Garcia-Fernandez, M.A. et al. (Oct. 1, 2003). "Role of Left Atrial Appendage Obliteration in Stroke Reduction in Patients With Mitral Valve Prosthesis," *Journal of the American College of Cardiology* 42(7):1253-1258.

Gardiner, G.A. Jr. et al. (Apr. 1986). "Complications of Transluminal Angioplasty," *Radiology* 159:201-208.

Gillinov, A.M. (2007). "Advances in Surgical Treatment of Atrial Fibrillation," *Stroke* 38(part 2):618-623.

Gilman, R.A. et al. (Apr. 1963). "Direct Left Ventricular Puncture," *California Medicine* 98(4):200-203.

Goodwin, W.E. et al. (Nov. 1950). "Translumbar Aortic Puncture and Retrograde Catheterization of the Aorta in Aortography and Renal Arteriography," *Annals of Surgery* 132(5):944-958.

Gottlieb, L.K. et al. (Sep. 12, 1994). "Anticoagulation in Atrial Fibrillation," *Arch Intern Med.* 154:1945-1953.

Graffigna, A. et al. (1993). "Surgical Treatment of Wolff-Parkinson-White Syndrome: Epicardial Approach Without the Use of Cardiopulmonary Bypass," *J. Card. Surg.* 8:108-116.

Haissaguerre, M. et al. (Nov. 2005). "Catheter Ablation of Long-Lasting Persistent Atrial Fibrillation: Clinical Outcome and Mechanisms of Subsequent Arrhythmias," *Journal of Cardiovascular Electrophysiology* 16(11):1138-1147.

Halperin, J.L. et al. (Aug. 1988). "Atrial Fibrillation and Stroke: New Ideas, Persisting Dilemmas," *Journal of the American Heart Association* 19(8):937-941.

Halperin, J.L. et al. (Oct. 1, 2003). "Obliteration of the Left Atrial Appendage for Prevention of Thromboembolism," *Journal of the American College of Cardiology* 42(7):1259-1261.

Hammill, S.C. (May 2006). "Epicardial Ablation: Reducing the Risks," *J. Cardiovasc. Electrophysiol.* 17:550-552.

Hara, H. et al. (Jan. 2008). "Percutaneous Left Atrial Appendage Obliteration," *JACC: Cardiovascular Imagin* 1(1):92-93.

Hart, R.G. et al. (Nov. 2, 1999). "Atrial Fibrillation and Thromboembolism: A Decade of Progress in Stroke Prevention," *Annals of Internal Medicine* 131(9):688-695.

Hart, R.G. et al. (2001). "Atrial Fibrillation and Stroke: Concepts and Controversies," *Stroke* 32:803-808.

Hart, R.G. (Sep. 11, 2003). "Atrial Fibrillation and Stroke Prevention," *The New England Journal of Medicine* 349(11):1015-1016.

Healey, J.S. et al. (Oct. 2003). "Surgical Closure of the Left Atrial Appendage for the Prevention of Stroke: A Randomized Pilot Trial of Safety and Efficacy (The Left Atrial Appendage Occlusion Study—LAAOS)," presented at the Canadian Cardiovascular Congress 2003, Toronto, Canada, Abstract No. 666, 2 pages.

Healey, J.S. et al. (Aug. 2005). "Left Atrial Appendage Occlusion Study (LAAOS): Results of a Randomized Controlled Pilot Study of Left Atrial Appendage Occlusion During Coronary Bypass Surgery in Patients At Risk for Stroke," *American Heart Journal* 150(2):288-293.

Hein, R. et al. (2005). "Patent Foramen Ovale and Left Atrial Appendage: New Devices and Methods for Closure," *Pediatric Cardiology* 26(3):234-240.

Heist, E.K. et al. (Nov. 2006). "Analysis of the Left Atrial Appendage by Magnetic Resonance Angiography in Patients with Atrial Fibrillation," *Heart Rhythm* 3(11):1313-1318.

Ho, I. et al. (Apr. 24, 2007). "Percutaneous Epicardial Mapping Ablation of a Posteroseptal Accessory Pathway," *Circulation* 115:e418-e421.

Ho, S.Y. et al. (Nov. 1999). "Anatomy of the Left Atrium: Implications for Radiofrequency Ablation of Atrial Fibrillation," *Journal of Cardiovascular Electrophysiology* 10(11):1525-1533.

Hoit, B.D. et al. (Jan. 1993). "Altered Left Atrial Compliance After Atrial Appendectomy. Influence on Left Atrial and Ventricular Filling," *Circulation Research* 72(1):167-175.

Inoue, Y. et al. (Jul.-Aug. 1997). "Video Assisted Thoracoscopic and Cardioscopic Radiofrequency Maze Ablation," *Asaio Journal* 43(4):334-337, Abstract Only.

Jaïs, P. et al. (2003). "Radiofrequency Ablation for Atrial Fibrillation," *European Society of Cardiology* 5(Supplement H):H34-H39.

Johnson, W.D. et al. (2000). "The Left Atrial Appendage: Our Most Lethal Human Attachment! Surgical Implications," *Euro. J. Cardiothoracic. Surg.* 17:718-722.

Jongbloed, M.R.M. et al. (2005). "Clinical Applications of Intracardiac Echocardiography in Interventional Procedures," *Heart* 91:981-990.

Kamohara, K. et al. (Aug. 2006). "Evaluation of a Novel Device for Left Atrial Appendage Exclusion: The Second-generation Atrial Exclusion Device," *The Journal of Thoracic and Cardiovascular Surgery* 132(2):340-346.

Kanderian, A.S. et al. (2008). "Success of Surgical Left Atrial Appendage Closure: Assessment by Transesophageal Echocardiography," *Journal of the American College of Cardiology* 52(11):924-929.

Kato, H. et al. (Aug. 1, 1996). "Evaluation of Left Atrial Appendage Stasis in Patients With Atrial Fibrillation Using Transesophageal Echocardiography With an Intravenous Albumin-Contrast Agent," *The American Journal of Cardiology* 78:365-369.

Katz, E.S. et al. (Aug. 2000). "Surgical Left Atrial Appendage Ligation is Frequently Incomplete: A Transesophageal Echocardiographic Study," *Journal of the American College of Cardiology* 36(2):468-471.

Kenner, H.M. et al. (Dec. 1966). "Intrapericardial, Intrapleural, and Intracardiac Pressures During Acute Heart Failure in Dogs Studied without Thoracotomy," *Circulation Research* 19:1071-1079.

Kerut, E.K. et al. (Jul. 2008). "Anatomy of the Left Atrial Appendage," *Echocardiography* 25(6):669-673.

Khargi, K. et al. (2005). "Surgical Treatment of Atrial Fibrillation: A Systematic Review," *European Journal of Cardiothoracic Surgery* 27:258-265.

Kim, K.B. et al. (Jan. 1998). "Effect of the Cox Maze Procedure on the Secretion of Atrial Natriuretic Peptide," *J. Thorac. Cardiovasc. Surg.* 115(1):139-146; discussion 146-147.

Kistler, P.M. et al. (May 2007). "The Left Atrial Appendage: Not Just an Innocent Bystander," *J. Cardiovasc Electrophysiol* 18(5):465-466.

Klein, H. et al. (Apr. 1990). "The Implantable Automatic Cardioverter-Defibrillator," *Herz* 15(2):111-125, Abstract Only.

Kolb, C. et al. (Feb. 2004). "Incidence of Antitachycardia Therapy Suspension Due to Magnet Reversion in Implantable Cardioverter Defibrillators," *Pace* 27:221-223.

Krikorian, J.G. et al. (Nov. 1978). "Pericardiocentesis," *Am. J. Med.* 65(5):808-814.

(56) References Cited

OTHER PUBLICATIONS

Krum, D. et al. (2004). "Visualization of Remnants of the left Atrial Appendage Following Epicardial Surgical Removal," *Heart Rhythm* 1:249.

Lacomis, J.M. et al. (Oct. 2003). "Multi-Detector Row CT of the Left Atrium and Pulmonary Veins before Radio-frequency Catheter Ablation for Atrial Fibrillation," *Radio Graphics* 23:S35-S48.

Lacomis, J.M. et al. (2007, e-pub. Oct. 17, 2007). "Dynamic Multidimensional Imaging of the Human Left Atrial Appendage," *Europace* 9:1134-1140.

Lee, R. et al. (1999). "The Closed Heart MAZE: A Nonbypass Surgical Technique," *The Annals of Thoracic Surgery* 67:1696-1702.

Levinson, M.L. et al. (1998). "Minimally Invasive Atrial Septal Defect Closure Using the Subxyphoid Approach," *Heart Surg. Forum* 1(1):49-53, Abstract Only.

Lewis, D.R. et al. (1999). "Vascular Surgical Intervention for Complications of Cardiovascular Radiology: 13 Years' Experience in a Single Centre," *Ann. R. Coll. Surg. Engl.* 81:23-26.

Li, H. (2007). "Magnet Decoration, Beautiful But Potentially Dangerous for Patients with Implantable Pacemakers or Defibrillators," *Heart Rhythm* 4(1):5-6.

Lindsay, B.D. (1996). "Obliteration of the Left Atrial Appendage: A Concept Worth Testing," *The Annals of Thoracic Surgery* 61:515.

Lip, G.Y.H. et al. (Jun. 2001). "Thromboprophylaxis for Atrial Flutter," *European Heart Journal* 22(12):984-987.

Lustgarten, D.L. et al. (May/Jun. 1999). "Cryothermal Ablation: Mechanism of Tissue Injury and Current Experience in the Treatment of Tachyarrhythmias," *Progress in Cardiovascular Diseases* 41(6):481-498.

Macris, M. et al. (Jan. 1999). "Minimally Invasive Access of the Normal Pericardium: Initial Clinical Experience with a Novel Device," *Clin. Cardiol.* 22(Suppl. I):I-36-I-39.

Maisch, B. et al. (Jan. 1999). "Intrapreicardial Treatment of Inflammatory and Neoplastic Pericarditis Guided by Pericardioscopy and Epicardial Biopsy—Results from a Pilot Study," *Clin. Cardiol.* 22(Supp. I):I-17-I-22.

Mannam, A.P. et al. (Apr. 1, 2002). "Safety of Subxyphoid Pericardial Access Using a Blunt-Tip Needle," *The American Journal of Cardiology* 89:891-893.

Mattox, K.L. et al. (May 1997). "Newer Diagnostic Measure and Emergency Management," *Ches Surg Clin N Am.* 7(2):213-226, Abstract Only.

McCarthy, P.M. et al. (2008). "Epicardial Atrial Fibrillation Ablation," Chapter 23 in *Contemporary Cardiology: Atrial Fibrillation, From Bench to Bedside*, Natale, A. et al. eds., Humana Press,: Totowa, NJ, pp. 323-332.

McCaughan, J.J. Jr., et al. (Nov. 1957). "Aortography Utilizing Percutaneous Left Ventricular Puncture," located at <http://www.archsurg.com>, last visited on Apr. 7, 2009, 73:746-751, Abstract Only.

McClelland, R.R. (1978). "Congenital Aneurysmal Dilatation of the Left Auricle Demonstrated by Sequential Cardiac Blood-Pool Scintiscanning," *J. Nucl. Med.* 19(5):507-509.

Melo, J. et al. (Apr. 21, 2008). "Surgery for Atrial Fibrillation in Patients with Mitral Valve Disease: Results at Five Years from the International Registry of Atrial Fibrillation Surgery," *The Journal of Thoracic and Cardiovascular Surgery* 135(4):863-869.

Miller, P.S.J. et al. (Feb. 2005). "Are Cost Benefits of Anticoagulation for Stroke Prevention in Atrial Fibrillation Underestimated?" *Stroke* 36:360-366.

Miyasaka, Y. et al. (Jul. 11, 2006). "Secular Trends in Incidence of Atrial Fibrillation in Olmsted County, Minnesota, 1980 to 2000, and Implications on the Projections for Future Prevalence," *Circulation* 114:119-125.

Morris, J.J. Jr. (1979). "Transvenous versus Transthoracic Cardiac Pacing," Chapter 16 in *Cardiac Pacing: A Concise Guide to Clinical Practice*, pp. 239-245.

Mráz, T. et al. (Apr. 2007). "Role of Echocardiography in Percutaneous Occlusion of the left Atrial Appendage," *Echocardiography* 24(4):401-404.

Naclerio, E.A. et al. (1979). "Surgical Techniques for Permanent Ventricular Pacing," Chapter 10 in *Cardiac Pacing: A Concise Guide to Clinical Practice*, pp. 145-168.

Nakai, T. et al. (May 7, 2002). "Percutaneous Left Atrial Appendage Occlusion (PLAATO) for Preventing Cardioembolism: First Experience in Canine Model," *Circulation* 105:2217-2222.

Nakajima, H. et al. (2004). "Consequence of Atrial Fibrillation and the Risk of Embolism After Percutaneous Mitral Commissurotomy: The Necessity of the Maze Procedure," *The Annals of Thoracic Surgery* 78:800-806.

Odell, J.A. et al. (1996). "Thorascopic Obliteration of the Left Atrial Appendage: Potential for Stroke Reduction?" *Ann. Thorac. Surg.* 61:565-569.

O'Donnell, M. et al. (2005). "Emerging Therapies for Stroke Prevention in Atrial Fibrillation," *European Heart Journal* 7(Supplement C):C19-C27.

Omran, H. et al. (1997). "Left Atrial Appendage Function in Patients with Atrial Flutter," *Heart* 78:250-254.

Onalan, O. et al. (2005). "Nonpharmacologic Stroke Prevention in Atrial Fibrillation," *Expert Rev. Cardiovasc. Ther.* 3(4):619-633.

Onalan, O. et al. (2007). "Left Atrial Appendage Exclusion for Stroke Prevention in Patients With Nonrheumatic Atrial Fibrillation," *Stroke* 38(part 2):624-630.

Ostermayer, S. et al. (2003). "Percutaneous Closure of the Left Atrial Appendage," *Journal of Interventional Cardiology* 16(6):553-556.

Ota, T. et al. (2006). "Epicardial Atrial Ablation Using a Novel Articulated Robotic Medical Probe Via a Percutaneous Subxiphoid Approach," *National Institute of Health* 1(6):335-340.

Ota, T. et al. (Oct. 2007). "Impact of Beating Heart left Atrial Ablation on Left-sided Heart Mechanics," *The Journal of Thoracic and Cardiovascular Surgery* 134:982-988.

Pennec, P.-Y. et al. (2003). "Assessment of Different Procedures for Surgical Left Atrial Appendage Exclusion," *The Annals of Thoracic Surgery* 76:2167-2168.

Perk, G. et al. (Aug. 2009). "Use of Real Time Three-Dimensional Transesophageal Echocardiography in Intracardiac Catheter Based Interventions," *J. Am Soc Echocardiogr* 22(8):865-882.

Pollick C. (Feb. 2000). "Left Atrial Appendage Myopathy," *Chest* 117(2):297-308.

Poulsen, T.S. et al. (Feb. 15, 2005). "Is Aspirin Resistance or Female Gender Associated With a High Incidence of Myonecrosis After Nonurgent Percutaneous Coronary Intervention?" *J. Am. Coll. Cardiol.* 45(4):635-636.

Reznik, G. et al. (Oct. 1992). "Percutaneous Endoscopic Implantation of Automatic Implantable Cardioverter/Defibrillator (AICD): An Animal Study of a New Nonthoracotomy Technique," *J. Laparoendosc. Surg.* 2(5):255-261, Abstract Only.

Robicsek, F. (1987). "Closed-Chest Decannulation of Transthoracically Inserted Aortic Balloon Catheter without Grafting," *Journal of Cardiac Surgery* 2(2):327-329.

Ross, J. Jr. et al. (Jun. 3, 2008). "Transseptal Left Heart Catheterization: A 50-Year Odyssey," *Journal of the American College of Cardiology* 51(22):2107-2115.

Rubin, D.N. et al. (Oct. 1, 1996). "Evaluation of Left Atrial Appendage Anatomy and Function in Recent-Onset Atrial Fibrillation by Transesophageal Echocardiography," *Am J Cardiol* 78:774-778.

Ruchat, P. et al. (2002). "Off-pump Epicardial Compartmentalization for Ablation of Atrial Fibrillation," *Interactive Cardio Vascular and Thoracic Surgery* 1:55-57.

Salzberg, S.P. et al. (2008). "Surgical Left Atrial Appendage Occlusion: Evaluation of a Novel Device with Magnetic Resonance Imaging," *European Journal of Cardiothoracic Surgery* 34:766-770.

Sapp, J. et al. (Dec. 2001). "Electrophysiology and Anatomic Characterization of an Epicardial Accessory Pathway," *Journal of Cardiovascular Electrophysiology* 12(12):1411-1414.

(56) References Cited

OTHER PUBLICATIONS

Scharf, C. et al. (2005). "Catheter Ablation for Atrial Fibrillation: Pathophysiology, Techniques, Results and Current Indications," *Continuous Medical Education* 8:53-61.

Scherr, D. et al. (Apr. 2009). "Incidence and Predictors of left Atrial Thrombus Prior to Catheter Ablation of Atrial Fibrillation," *Journal of Cardiovascular Electrophysiology* 20(4):379-384.

Schmidt, H. et al. (Sep. 2001). "Prevalence of Left Atrial Chamber and Appendage Thrombi in Patients With Atrial Flutter and Its Clinical Significance," *Journal of the American College of Cardiology* 38(3):778-784.

Schneider, B. et al. (2005, e-pub. Aug. 22, 2005). "Surgical Closure of the Left Atrial Appendage—A Beneficial Procedure?" *Cardiology* 104:127-132.

Schweikert, R.A. et al. (Sep. 16, 2003). "Percutaneous Pericardial Instrumentation for Endo-Epicardial Mapping of Previously Failed Ablation," *Circulation* 108:1329-1335.

Schweikert, R.A. et al. (2005). "Epicardial Access: Present and Future Applications for Interventional Electrophysiologists," Chapter 25 in *New Arrhythmia Technolgies*, Wang, P.J. ed., Blackwell Publishing, pp. 242-256.

Seferovic, P. et al. (Jan. 1999). "Initial Clinical Experience with the PerDUCER® Device: Promising New Tool in the Diagnosis and Treatment of Pericardial Disease," *Clin. Cardiol.* 22(Supp I):I-30-I-35.

Sengupta, P.P. et al. (2005). "Transoesophageal Echocardiography," *Heart* 91:541-547.

Sharada, K. et al. (2005). "Non-Surgical Transpericardial Catheter Ablation of Post-Infarction Ventricular Tachycardia," *Indian Heart J* 57:58-61.

Sievert, H. et al. (Apr. 23, 2002). "Percutaneous Left Atrial Appendage Transcatheter Occlusion to Prevent Stroke in High-Risk Patients With Atrial Fibrillation," *Circulation* 105:1887-1889.

Singer, D.E. et al. (Sep. 2004). "Antithrombotic Therapy in Atrial Fibrillation: The Seventh ACCP Conference on Antithrombotic and Thrombolytic Therapy," *Chest* 126(3):429S-456S.

Smith, P.W. et al. (Nov. 1956). "Diagnosis of Mitral Regurgitation by Cardioangiography," *Circulation* 14:847-853.

Soejima, K. et al. (2004). "Subxiphoid Surgical Approach for Epicardial Catheter-Based Mapping and Ablation in Patients With Prior Cardiac Surgery or Difficult Pericardial Access," *Circulation* 110:1197-1201.

Sosa, E. et al. (1996). "A New Technique to Perform Epicardial Mapping in the EP Laboratory," *J. Cardiovasc. Electrophysiol.* 7(6):531-536.

Sosa, E. et al. (Mar. 1998). "Endocardial and Epicardial Ablation Guided by Nonsurgical Transthoracic Epicardial Mapping to Treat Recurrent Ventricular Tachycardia," *J. Cardiovasc. Elecytophysiol.* 9(3):229-239.

Sosa, E. et al. (Dec. 14, 1999). "Different Ways of Approaching the Normal Pericardial Space," *Circulation* 100(24):e115-e116.

Sosa, E. et al. (Jul. 15, 2002). "Gaining Access to the Pericardial Space," *The American Journal of Cardiology* 90:203-204.

Sosa, E. et al. (Apr. 2005). "Epicardial Mapping and Ablation Techniques to Control Centricular Tachycardia," *Journal of Cardiovasc. Electrphsiol.* 16(4):449-452.

Sparks, P.B. et al. (2001). "Is Atrial Flutter a Risk Factor for Stroke?" *Journal of the American College of Cardiology* 38(3):785-788.

Spodick, D.H. (Nov. 1970). "Medical History of the Pericardium," *The American Journal of Cardiology* 26:447-454.

Stewart, J.M. et al. (Apr. 1992). "Bilateral Atrial Appendectomy Abolishes Increased Plasma Atrial Natriuretic Peptide Release and Blunts Sodium and Water Excretion During Volume Loading in Conscious Dogs," *Circulation Research* 70(4):724-732.

Stewart, S. (1974). "Placement of the Sutureless Epicardial Pacemaker Lead by the Subxiphoid Approach," *Ann. of Thoracic Surg.* 18(3):308-313.

Stoddard, M.F. et al. (1995). "Left Atrial Appendage Thrombus is not Uncommon in Patients with Acute Atrial Fibrillation and a Recent Embolic Event: A Transesophageal Echocardiographic Study," *J. Am. Coll. Cardiol.* 25:452-459, Abstract Only.

Stokes, K. (Jun. 1990). "Implantable Pacing Lead Technology," *IEEE Engineering in Medicine and Biology* pp. 43-49.

Stöllberger, C. et al. (2000). "Is the Left Atrial Appendage Our Most Lethal Attachment?" *European Journal of Cardio-Thoracic Surgery* 18:625-626.

Stöllberger, C. et al. (Dec. 2003). "Elimination of the Left Atrial Appendage to Prevent Stroke or Embolism?: Anatomic, Physiologic, and Pathophysiologic Considerations," 124(6):2356-2362.

Stöllberger, C. et al. (2006). "Stroke Prevention by Means of Epicardial Occlusion of the Left Atrial Appendage," *Journal of Thoracic and Cardiovascular Surgery* 132(1):207-208.

Stöllberger, C. et al. (2007). "Arguments Against Left Atrial Appendage Occlusion for Stroke Prevention," *Stroke* 38:e77.

Stöllberger, C. et al. (2007). "Leave the Left Atrial Appendage Untouched for Stroke Prevention!" *Journal of Thoracic and Cardiovascular Surgery* 134(2):549-550.

Su, P. et al. (Sep. 2008, e-pub. May 8, 2007). "Occluding the Left Atrial Appendage: Anatomical Considerations," *Heart* 94(9):1166-1170.

Subramanian, V.A. (Jun. 1997). "Less Invasive Arterial CABG on a Beating Heart," *Ann. Thorac. Surg.* 63(6 Suppl.):S68-S71.

Subramanian, V.A. et al. (Dec. 1997). "Minimally Invasive Direct Coronary Artery Bypass Grafting: two-Year Clinical Experience," *Ann. Thorac. Surg.* 64(6):1648-1653, Abstract Only.

Suehiro, S. et al. (1996). "Echocardiography-Guided Pericardiocentesis With a Needle Attached to a Probe," *Ann. Thoracic Surg.* 61:741-742.

Sun, F. et al. (Feb. 2006). "Subxiphoid Access to Normal Pericardium with Micropuncture Set: Technical Feasibility Study in Pigs," *Radiology* 238(2):719-724.

Szili-Torok, T. et al. (2001). "Transseptal Left heart Catheterisation Guided by Intracardiac Echocardiography," *Heart* 86:e11-e15.

Tabata, T. et al. (Feb. 1, 1998). "Role of Left Atrial Appendage in left Atrial Reservoir Function as Evaluated by Left Atrial Appendage Clamping During Cardiac Surgery," *The American Journal of Cardiology* 81:327-332.

Tomar, M. et al. (Jul.-Aug. 2006). "Transcatheter Closure of Fossa Ovalis Atrial Septal Defect: A Single Institutional Experience," *Indian Heart Journal* 58(4):325-329.

Troughton, R.W. et al. (Feb. 28, 2004). "Pericarditis," *The Lancet* 363:717-727.

Ulicny K.S. et al. (Jun. 1992). "Conjoined Subrectus Pocket for Permanent Pacemaker Placement in the Neonate," *Ann Thorac Surg.* 53(6):1130-1131, Abstract Only.

Valderrabano, M. et al. (Sep. 2004). "Percutaneous Epicardial Mapping During Ablation of Difficult Accessory Pathways as an Alternative to Cardiac Surgery," *Heart Rhythm* 1(3):311-316.

Von Korn, H. et al. (2006). "Simultaneous Combined Interventional Percutaneous Left Atrial Auricle and Atrial Septal Defect Closure," *Heart* 92:1462.

Wang, T.J. et al. (Aug. 27, 2003). "A Risk Score for Predicting Stroke or Death in Individuals With New-Onset Atrial Fibrillation in the Community," *American Medical Association* 290(8):1049-1056.

Watkins, L. et al. (Nov. 1982). "Implantation of the Automatic Defibrillator: The Subxiphoid Approach," *Ann. of Thoracic Surg.* 34(5):515-520.

W.L. Gore & Associates (Aug. 11, 2006). "Gore Helex™ Septal Occluder," located at <http://www.fda.gov/cdrh/pdf5/p050006a. pdf>, last visited on Jun. 14, 2007, 3 pages.

Wolber, T. et al. (Jan. 2007). "Potential Interference of Small Neodymium Magnets with Cardiac pacemakers and Implantable Cardioverter-defibrillators," *Heart Rhythm* 4(1):1-4.

Wolf, P.A. et al. (Oct. 1978). "Epidemiologic Assessment of Chronic Atrial Fibrillation and Risk of Stroke: The Fiamingham Study," *Neurology* 28:973-977.

Wolf, P.A. et al. (Aug. 1991). "Atrial Fibrillation as an Independent Risk Factor for Stroke: The Framingham Study," *Stroke* 22(8):983-988.

(56) References Cited

OTHER PUBLICATIONS

Wolf, P.A. et al. (Feb. 9, 1998). "Impact of Atrial Fibrillation on Mortality, Stroke, and Medical Costs," *Arch Intern Med* 158:229-234.
Wong, J.W.W. et al. (2006). "Impact of Maze and Concomitant Mitral Valve Surgery on Clinical Outcomes," *The Annals of Thoracic Surgery* 82:1938-1947.
Wongcharoen, W. et al. (Sep. 2006). "Morphologic Characteristics of the Left Atrial Appendage, Roof, and Septum: Implications for the Ablation of Atrial Fibrillation," *Journal of Cardiovascular Electrophysiology* 17(9):951-956.
Wood, M.A. (Jan. 2006). "Percutaneous Pericardial Instrumentation in the Electrophysiology Laboratory: A Case of Need," *Heart Rhythm* 3(1):11-12.
Wudel, J.H. et al. (Apr. 3, 2008). "Video-Assisted Epicardial Ablation and left Atrial Appendage Exclusion for Atrial Fibrillation: Extended Follow-Up," *The Annals of Thoracic Surgery* 85:34-38.
Wyse, D.G. et al. (Dec. 5, 2002). "Of 'Left Atrial Appendage Amputation, Ligation, or Occlusion in Patients with Atrial Fibrillation'," *N Engl J Med* 347(23):1825-1833, Abstract Only.
Yamada, Y. et al. (Aug. 2006). "Video-Assisted Thoracoscopy to Treat Atrial Tachycardia Arising from Left Atrial Appendage," *Journal of Cardiovascular Electrophysiology* 17(8):895-898.
Zapolanski, A. et al. (May 2008). "Safe and Complete Exclusion of the left Atrial Appendage, A Simple Epicardial Approach," *Innovations* 3(3):161-163.
Zenati, M.A. et al. (Sep. 2003). "Left Heart Pacing Lead Implantation Using Subxiphoid Videopericardioscopy," *Journal of Cardiovascular Electrophysiology* 14(9):949-953.
Zenati, M.A. et al. (2004). "Mechanical Function of the Left Atrial Appendage Following Epicardial Bipolar Radiofrequency Ablation," *Cardiothoracic Techniques and Technologies X*, Abstract 121A, p. 176.
Zenati, M.A. et al. (2005). "Modification of the Left Atrial Appendage," Chapter 12 in *Innovative Management of Atrial Fibrillation*, Schwartzman, David ed., Blackwell Science Ltd., 5 pages.
Non-Final Office Action dated Mar. 13, 2008 for U.S. Appl. No. 10/963,371, filed Oct. 11, 2004, 13 pages.
Non-Final Office Action dated Aug. 6, 2008 for U.S. Appl. No. 10/963,371, filed Oct. 11, 2004, 12 pages.
Final Office Action dated Jun. 22, 2009, for U.S. Appl. No. 10/963,371, filed Oct. 11, 2004, 11 pages.
Notice of Allowance dated Sep. 17, 2010, for U.S. Appl. No. 10/963,371, filed Oct. 11, 2004, 7 pages.
Non-Final Office Action dated Jun. 26, 2009, for U.S. Appl. No. 11/600,671, filed Nov. 15, 2006, 9 pages.
Final Office Action dated Apr. 14, 2010, for U.S. Appl. No. 11/600,671, filed Nov. 15, 2006, 7 pages.
Notice of Allowance dated Sep. 17, 2010, for U.S. Appl. No. 11/600,671, filed Nov. 15, 2006, 7 pages.
Non-Final Office Action dated Jul. 22, 2010, for U.S. Appl. No. 12/037,802, filed Feb. 26, 2008, 10 pages.
Final Office Action dated Apr. 26, 2011, for U.S. Appl. No. 12/037,802, filed Feb. 26, 2008, 9 pages.
Non-Final Office Action dated Jan. 16, 2013, for U.S. Appl. No. 12/037,802, filed Feb. 26, 2008, 11 pages.
Final Office Action dated Nov. 8, 2013, for U.S. Appl. No. 12/037,802, filed Feb. 26, 2008, 15 pages. (1.02).
Notice of Allowance dated Apr. 3, 2014, for U.S. Appl. No. 12/037,802, filed Feb. 26, 2008, 8 pages. (1.02).
Non-Final Office Action dated Mar. 7, 2012, for U.S. Appl. No. 12/124,023, filed May 20, 2008, 13 pages. (1.03).
Final Office Action dated Oct. 18, 2012, for U.S. Appl. No. 12/124,023, filed May 20, 2008, 15 pages.
Non-Final Office Action dated May 31, 2013, for U.S. Appl. No. 12/124,023, filed May 20, 2008, 14 pages.
Non-Final Office Action dated May 4, 2015, for U.S. Appl. No. 12/124,023, filed May 20, 2008, 8 pages.
Notice of Allowance dated Oct. 21, 2015, for U.S. Appl. No. 12/124,023, filed May 20, 2008, 9 pages.

Non-Final Office Action dated Dec. 30, 2009, for U.S. Appl. No. 11/400,714, filed Apr. 7, 2006, 8 pages.
Final Office Action dated Jul. 21, 2010, for U.S. Appl. No. 11/400,714, filed Apr. 7, 2006, 10 pages.
Notice of Allowance dated Nov. 24, 2010, for U.S. Appl. No. 11/400,714, filed Apr. 7, 2006, 8 pages.
Non-Final Office Action dated Dec. 22, 2011, for U.S. Appl. No. 13/033,532, filed Feb. 23, 2011, 8 pages.
Final Office Action dated Jul. 11, 2012, for U.S. Appl. No. 13/033,532, filed Feb. 23, 2011, 8 pages.
Non-Final Office Action dated Apr. 2, 2014, for U.S. Appl. No. 13/033,532, filed Feb. 23, 2011, 8 pages.
Final Office Action dated Aug. 12, 2014, for U.S. Appl. No. 13/033,532, filed Feb. 23, 2011, 7 pages.
Non-Final Office Action dated Oct. 28, 2015, for U.S. Appl. No. 13/033,532, filed Feb. 23, 2011, 9 pages.
Final Office Action dated Apr. 1, 2016, for U.S. Appl. No. 13/033,532, filed Feb. 23, 2011, 8 pages.
Non-Final Office Action dated Nov. 15, 2010, for U.S. Appl. No. 12/055,213, filed Mar. 25, 2008, 18 pages.
Non-Final Office Action dated Apr. 28, 2011, for U.S. Appl. No. 12/055,213, filed Mar. 25, 2008, 20 pages.
Final Office Action dated Oct. 28, 2011, for U.S. Appl. No. 12/055,213, filed Mar. 25, 2008, 15 pages.
Non-Final Office Action dated Sep. 18, 2013, for U.S. Appl. No. 12/055,213, filed Mar. 25, 2008, 15 pages.
Notice of Allowance dated Mar. 4, 2014, for U.S. Appl. No. 12/055,213, filed Mar. 25, 2008, 9 pages.
Non-Final Office Action dated Oct. 27, 2011, for U.S. Appl. No. 12/363,359, filed Jan. 30, 2009, 11 pages.
Final Office Action dated May 4, 2012, for U.S. Appl. No. 12/363,359, filed Jan. 30, 2009, 10 pages.
Non-Final Office Action dated Jun. 17, 2014, for U.S. Appl. No. 12/363,359, filed Jan. 30, 2009, 7 pages.
Final Office Action dated Nov. 14, 2014, for U.S. Appl. No. 12/363,359, filed Jan. 30, 2009, 10 pages.
Non-Final Office Action dated Sep. 10, 2015, for U.S. Appl. No. 12/363,359, filed Jan. 30, 2009, 13 pages.
Final Office Action dated Mar. 17, 2016, for U.S. Appl. No. 12/363,359, filed Jan. 30, 2009, 10 pages.
Non-Final Office Action dated Nov. 9, 2011, for U.S. Appl. No. 12/363,381, filed Jan. 30, 2009, 10 pages.
Final Office Action dated May 16, 2012, for U.S. Appl. No. 12/363,381, filed Jan. 30, 2009, 8 pages.
Notice of Allowance dated Apr. 1, 2014, for U.S. Appl. No. 12/363,381, filed Jan. 30, 2009, 9 pages.
Notice of Allowance dated Dec. 29, 2014, for U.S. Appl. No. 12/363,381, filed Jan. 30, 2009, 9 pages.
Non-Final Office Action dated Feb. 17, 2011, for U.S. Appl. No. 12/212,511, filed Sep. 17, 2008, 14 pages.
Final Office Action dated Sep. 20, 2011, for U.S. Appl. No. 12/212,511, filed Sep. 17, 2008, 8 pages.
Non-Final Office Action dated Apr. 2, 2012, for U.S. Appl. No. 12/212,511, filed Sep. 17, 2008, 5 pages.
Final Office Action dated Jul. 24, 2012, for U.S. Appl. No. 12/212,511, filed Sep. 17, 2008, 6 pages.
Notice of Allowance dated Feb. 22, 2013, for U.S. Appl. No. 12/212,511, filed Sep. 17, 2008, 8 pages.
Corrected Notice of Allowability dated Mar. 18, 2013, for U.S. Appl. No. 12/212,511, filed Sep. 17, 2008, 4 pages.
Non-Final Office Action dated Mar. 29, 2013, for U.S. Appl. No. 12/752,873, filed Apr. 1, 2010, 16 pages.
Final Office Action dated Jan. 13, 2014, for U.S. Appl. No. 12/752,873, filed Apr. 1, 2010, 10 pages.
Non-Final Office Action dated Nov. 10, 2014, for U.S. Appl. No. 12/752,873, filed Apr. 1, 2010, 10 pages.
Notice of Allowance dated Jul. 22, 2015, for U.S. Appl. No. 12/752,873, filed Apr. 1, 2010, 8 pages.
Non-Final Office Action dated Mar. 31, 2015, for U.S. Appl. No. 13/490,919, filed Jun. 7, 2012; 14 pages.
Final Office Action dated Nov. 18, 2015, for U.S. Appl. No. 13/490,919, filed Jun. 7, 2012; 10 pages.

(56) References Cited

OTHER PUBLICATIONS

Extended European Search Report dated Jul. 10, 2015, for European Patent Application No. 15153029.2, filed on Mar. 25, 2008, 6 pages.
Extended European Search Report dated Feb. 10, 2017, for EP Application No. 10 759 425.1, filed on Apr. 1, 2010, 7 pages.
International Search Report dated Feb. 27, 2007, for PCT Application No. PCT/US2008/003938, filed on Mar. 25, 2008, 5 pages.
International Search Report dated Jun. 1, 2010, for PCT Application No. PCT/US2010/029668, filed on Apr. 1, 2010, 2 pages.
Written Opinion of the International Searching Authority dated Feb. 27, 2007, for PCT Application No. PCT/US2008/003938, filed on Mar. 25, 2008, 10 pages.
Written Opinion of the International Searching Authority dated Jun. 1, 2010, for PCT Application No. PCT/US2010/029668, filed on Apr. 1, 2010, 8 pages.
Final Office Action dated Jun. 8, 2017, for U.S. Appl. No. 14/625,540, filed Feb. 18, 2015, 14 pages.
Non-Final Office Action dated Dec. 2, 2016, for U.S. Appl. No. 14/625,540, filed Feb. 18, 2015, 20 pages.
Non-Final Office Action dated Jan. 4, 2018, for U.S. Appl. No. 15/080,398, filed Mar. 24, 2016, 6 pages.
Non-Final Office Action dated Jan. 12, 2018, for U.S. Appl. No. 14/928,836, filed Oct. 30, 2015, 12 pages.
Non-Final Office Action dated Jan. 26, 2018, for U.S. Appl. No. 14/625,540, filed Feb. 18, 2015, 16 pages.

\* cited by examiner

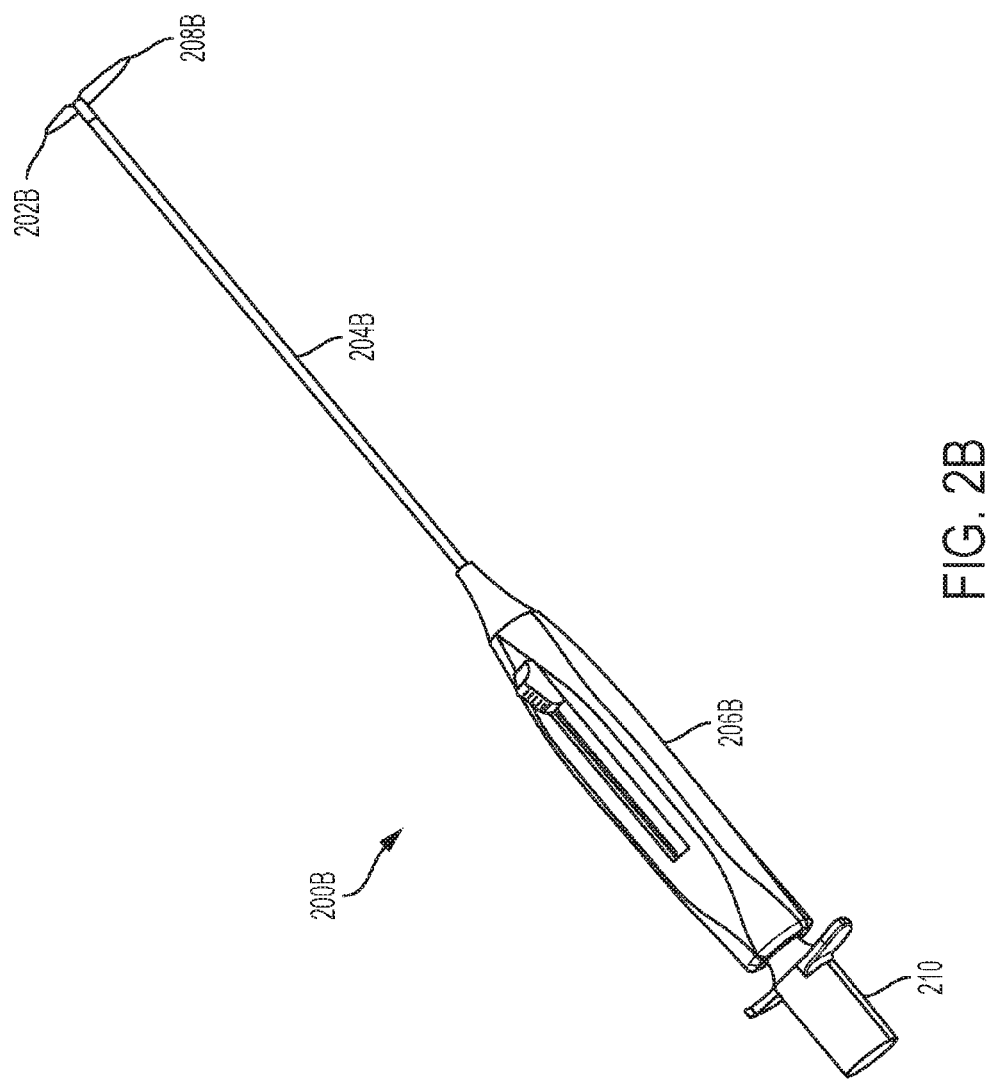

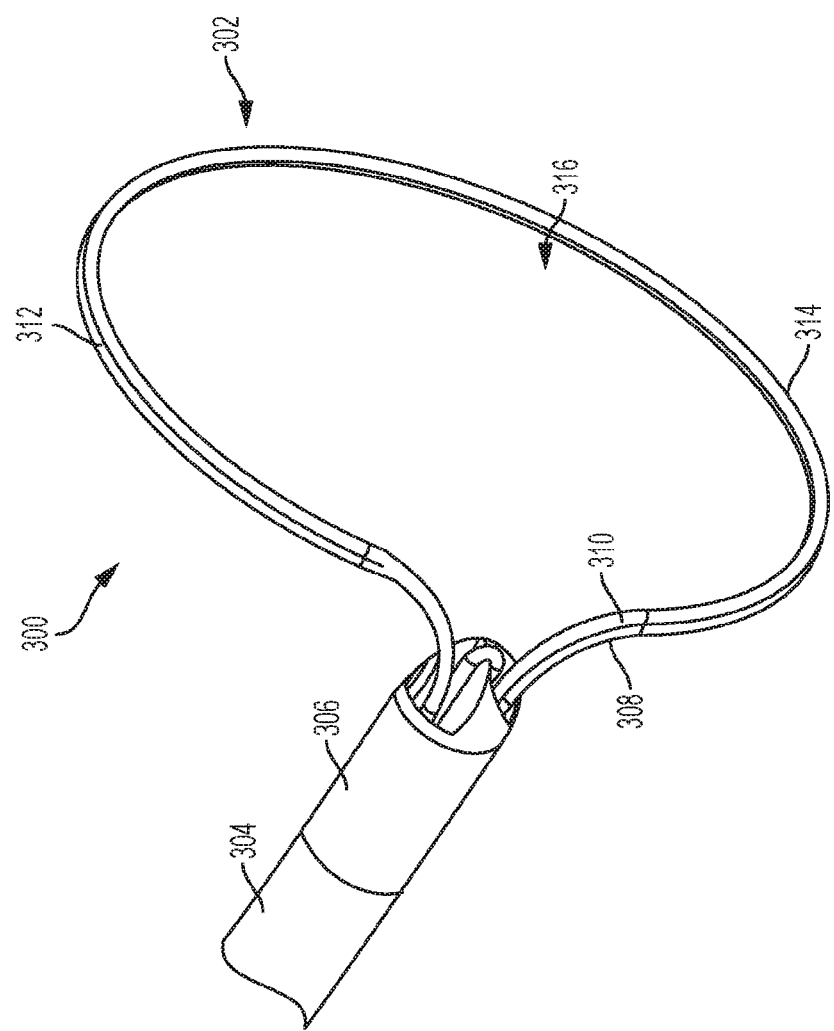

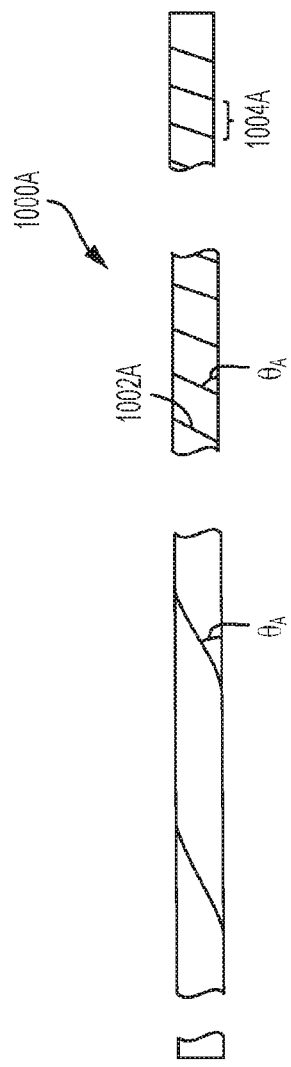
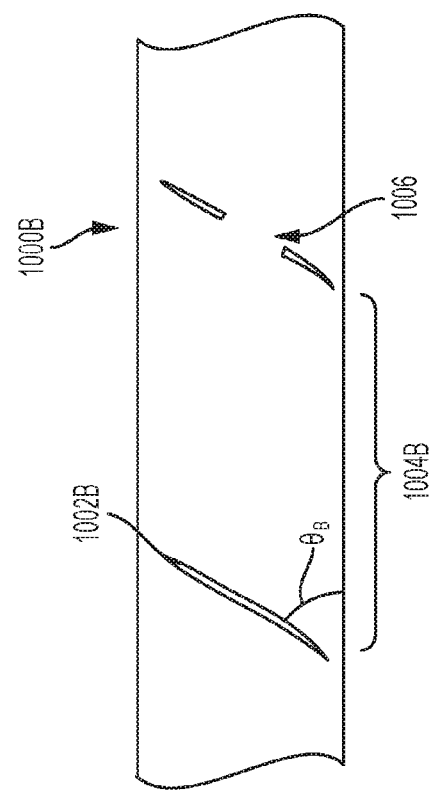
FIG. 10A
FIG. 10B

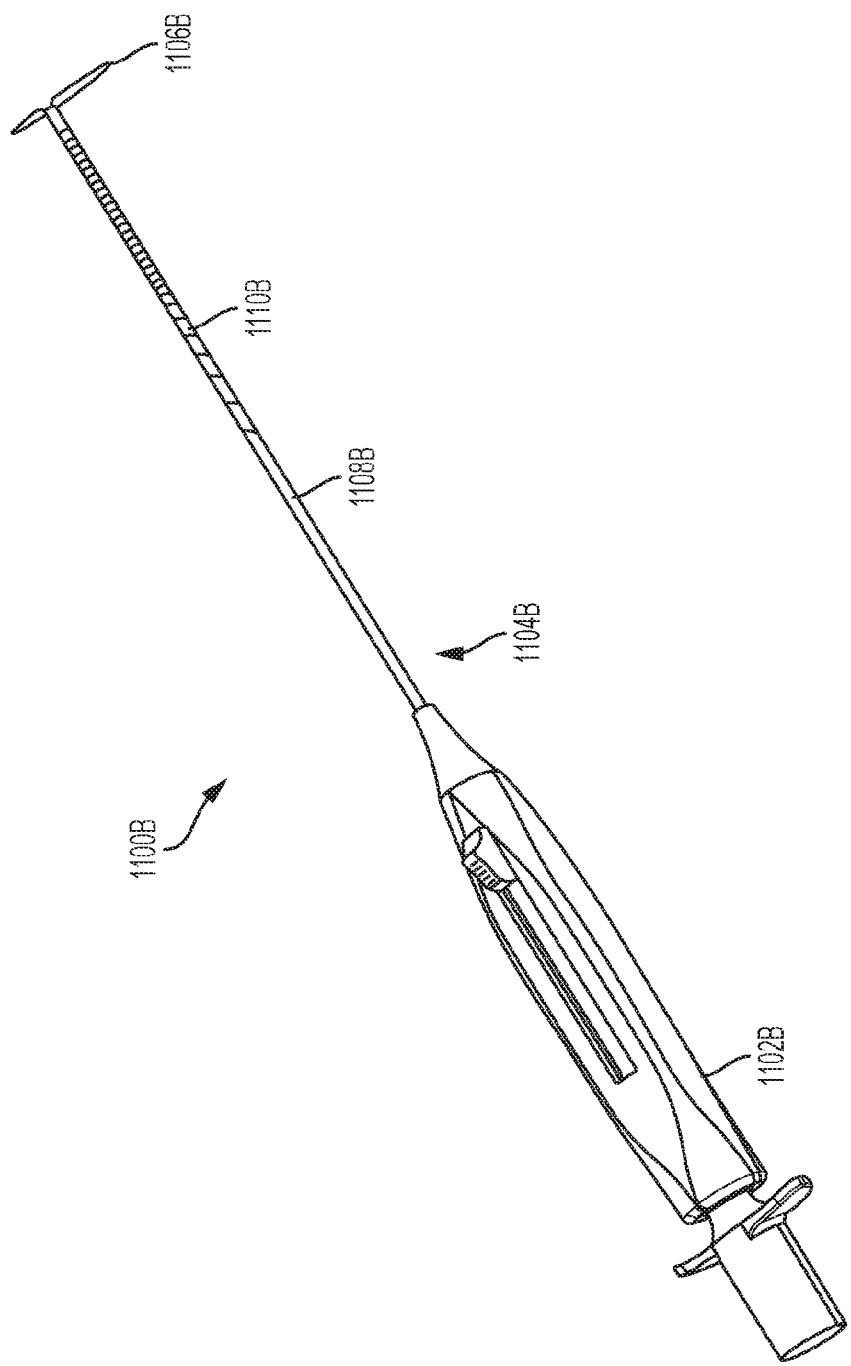

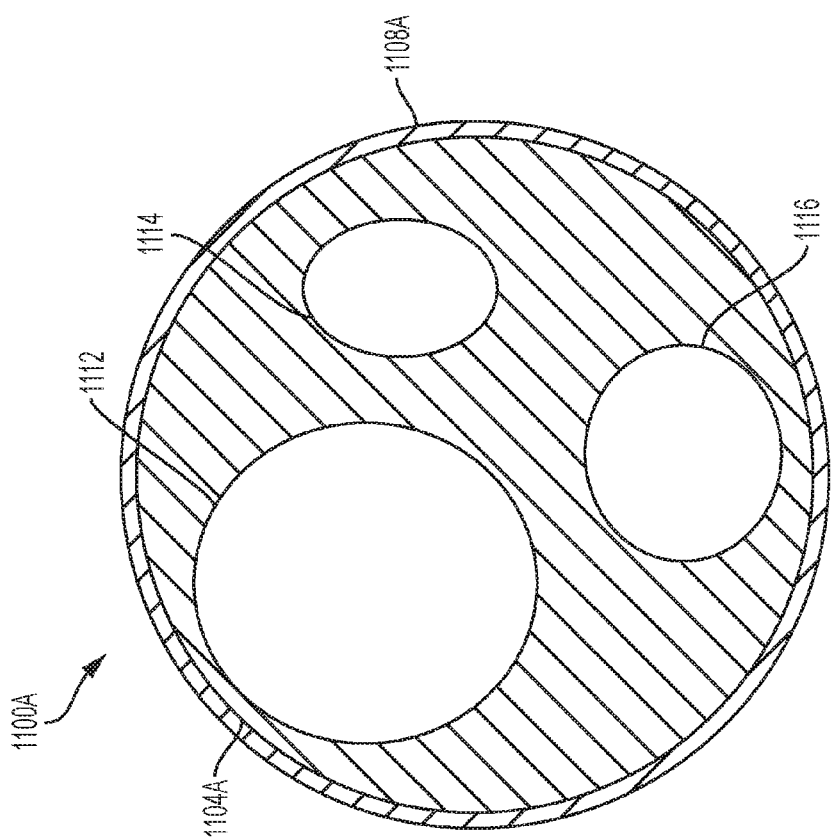

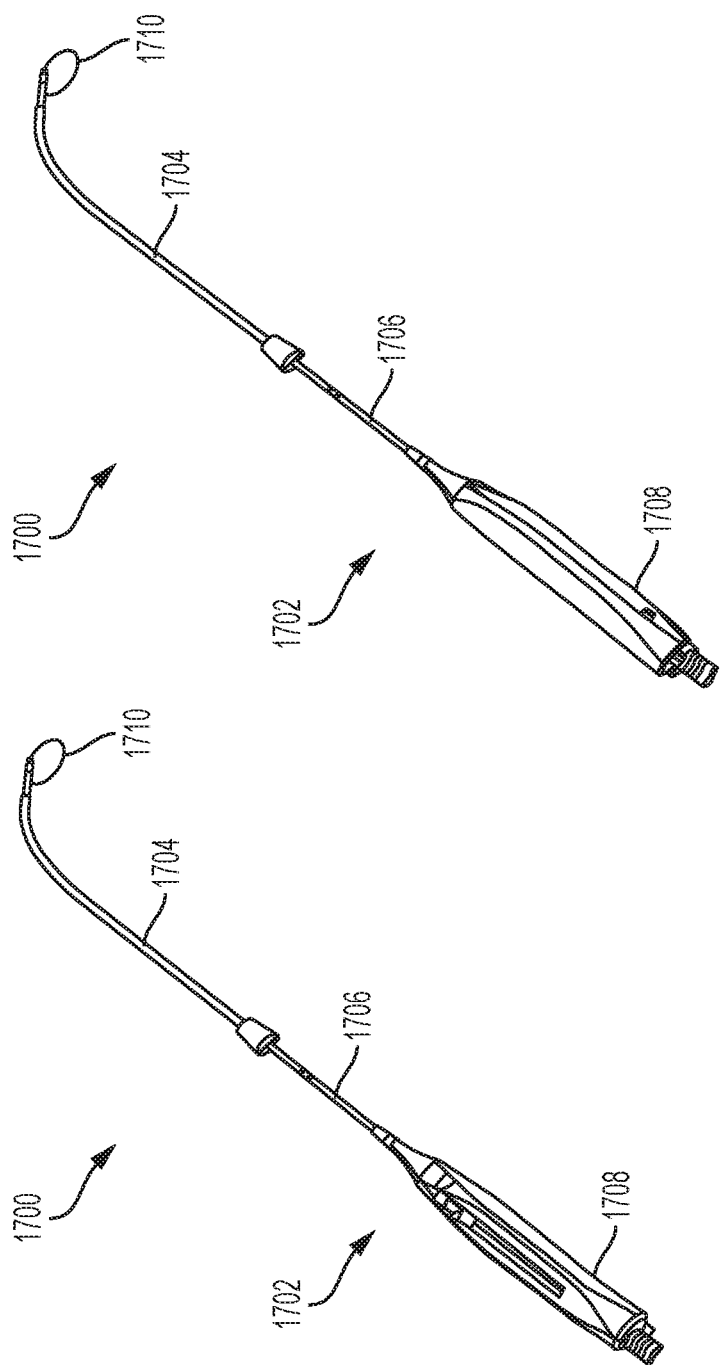

DEVICES AND METHODS FOR LEFT ATRIAL APPENDAGE CLOSURE

CROSS-REFERENCE TO RELATED APPLICATIONS

This application claims priority to U.S. Provisional Patent Application Ser. No. 62/137,738, filed on Mar. 24, 2015, which is hereby incorporated by reference herein in its entirety.

FIELD

This invention relates generally to devices and methods for ligating tissue, such as the left atrial appendage, using surgically, minimally invasive, or intravascular approaches.

BACKGROUND OF THE INVENTION

Atrial fibrillation is a common problem that afflicts millions of patients. Atrial fibrillation often results in the formation of a thrombus, or clot, in the appendage of the left atrium. This presents a problem, inasmuch as the thrombus can dislodge and embolize to distant organs, which may result in adverse events such as a stroke. For this reason, most patients with atrial fibrillation are treated with one or more blood thinners to help prevent the formation of a thrombus. Blood thinners, however, can present health risks of their own, especially in the elderly. These risks, such as bleeding, often require a user to make significant lifestyle changes.

Several methods have been developed to address the potential problem of thrombus formation in the left atrial appendage. One such method includes suturing the left atrial appendage along the base or ostial neck where it joins the atrial chamber. In this way, blood flow into the atrial appendage is cut off, eliminating the risk of thrombus formation therein. Other methods have also been investigated. These methods include stapling the base of the appendage and filling the appendage with a space-occupying or occluding member. Stapling is not preferred given the fragility of the appendage and its tendency to rupture, whereas occlusion devices may not effectively prevent all blood flow into the appendage.

Most of these procedures are typically performed through open-heart surgery; however, some may also be performed using minimally invasive techniques. Open-heart surgery may limit the availability of these procedures to those who are at a particularly high risk, or who are otherwise undergoing an open-heart procedure. In addition, open-heart surgery requires general anesthesia and has a number of well-known risks, which may make it less desirable for some. Therefore, additional devices and methods for closing the left atrial appendage using minimally invasive, intravascular, or a combination of these techniques would be desirable in order to avoid the need for opening the chest.

However, at times, the closure of the left atrial appendage is a concomitant procedure during other cardiac procedures, and performing the closure during an open-heart procedure may provide benefits in comparison to a minimally invasive procedure. For example, performing the closure during an open-heart procedure may make it easier for instruments to access the heart and may allow for better control or maneuverability of those instruments. Additionally, using an open-heart approach may provide a better view of the heart and the surrounding tissue during the procedure. Thus, additional devices for use in open surgical procedures are desirable, especially when those devices offer additional advantages over standard devices.

BRIEF SUMMARY OF THE INVENTION

Described here are devices, systems, and methods for closing the left atrial appendage. In general, the devices described here may comprise an elongate body, a closure element, and a suture loop. In some variations, the elongate body may comprise a stiffened proximal portion, a flexible middle portion, and a flexible distal portion. The stiffened proximal portion and the flexible middle portion may comprise cylindrical cross-sections, and the flexible distal portion may comprise a D-shaped cross-section having a height. In some variations, a diameter of the stiffened proximal portion may be greater than a diameter of the flexible middle portion, and a diameter of the flexible middle portion may be greater than the height of the distal portion. In some instances, the elongate body may be configured to resist rotating when a torsional force is applied. The closure element may comprise a loop defining a continuous aperture therethough and may be at least partially housed within the elongate body. In some variations, the stiffened proximal portion may comprise a braided catheter.

In these embodiments, the elongate body may comprise a lumen therethrough and a hypotube disposed within the lumen. In some variations, the hypotube and the stiffened proximal portion may be similar lengths. Additionally, the hypotube may comprise a laser cut pattern. In other embodiments, the stiffened proximal portion may comprise a catheter and a stiffening element. For example, the stiffening element may comprise a braided sheath adhered to the catheter and/or a wire embedded in the catheter. In some variations, the catheter may comprise a lumen therethrough and the stiffening element may comprise a polymer tube disposed in the lumen. In these variations, the polymer tube may be more resistant to bending than the catheter. In other variations, the catheter may comprise a lumen therethrough and the stiffening element may comprise a stainless steel hypotube disposed in the lumen. The closure devices may further comprise a laminated jacket on the stiffened proximal portion and the flexible middle portion.

In some variations, the elongate body of the devices described here may comprise a tapered transition between the flexible middle portion and the flexible distal portion. In some instances, the elongate body may comprise a second flexible middle portion between the flexible middle portion and the flexible distal portion, and the second flexible middle portion may comprise a D-shaped cross-section. The length of the flexible middle portion may be between about 1.50 inches (3.81 cm) and about 2.50 inches (6.35 cm), and in some variations, it may be about 1.90 inches (4.83 cm). The length of the second flexible middle portion may be between about 2.00 inches (5.08 cm) and 3.00 inches (7.62 cm), and in some instances, may be about 2.30 inches (5.84 cm). In some embodiments, the elongate body may further comprise a tapered transition between the second flexible middle portion and the flexible distal portion.

The stiffened proximal portion of the devices described here may have a diameter between about 0.160 inches (4.064 mm) and about 0.169 inches (4.293 mm), and in some instances, the diameter of the stiffened proximal portion may be about 0.163 inches (4.115 mm). The flexible middle portion of the devices described here may have a diameter of between about 0.156 inches (3.962 mm) and 0.162 inches (4.115 mm), and in some instances, the diameter of the flexible middle portion may be about 0.160 inches (4.064 mm). The flexible distal portion may have a height between about 0.094 inches (2.388 mm) and about 0.098 inches (2.489 mm), and in some instances, the height of the flexible distal portion may be about 0.096 inches (2.438 mm). In some variations, the diameter of the stiffened proximal portion may be less than or equal to 1.06 times the diameter of the flexible middle portion.

The stiffened proximal portion may have a length between about 12.00 inches (30.48 cm) and about 14.00 inches (35.56 cm), and in some instances, the length of the stiffened proximal portion may be about 13.00 inches (33.02 cm). The flexible middle portion may have a length between about 3.50 inches (8.89 cm) and about 5.0 inches (12.7 cm), and in some instances, the length of the flexible middle portion may be about 4.20 inches (10.67 cm). The flexible distal portion of the devices described here may have a length of between about 0.20 inches (5.08 mm) and about 0.40 inches (10.16 mm), and in some instances, the flexible distal portion may have a length of about 0.25 inches (6.35 mm). In some embodiments, the length of the stiffened proximal portion may be at least 2.5 times greater than the length of the flexible middle portion. In some variations, the length of the stiffened proximal portion may be at least 3.0 times greater than the length of the flexible middle portion.

The closure devices may further comprise a first lumen and a second lumen. In some variations, there may be at least about 0.005 inches (0.127 mm) between the first and second lumens. In some embodiments, the closure devices may also comprise a handle, and rotating the handle 180 degrees may cause a distal tip of the elongate body to rotate at least 120 degrees, at least 160 degrees, or at least 175 degrees. Moreover, in some variations, the closure device may further comprise a lumen configured to retain an end of the suture loop, and the lumen may comprise a PTFE lining.

In some embodiments, surgical devices for closing the left atrial appendage may comprise an elongate body, a closure element, and a malleable member. The elongate body may comprise a first lumen, a second lumen, and a third lumen. The closure element may comprise a loop defining a continuous aperture therethrough. A first end of the closure element may be slideably disposed in the first lumen, and a second end of the closure element may be fixedly disposed in the second lumen. The malleable member may be fixedly attached to the elongate body and may be configured to retain a curve after a force is applied. In some variations, applying a force to the malleable member may modify the curvature of the elongate body. The surgical closure devices may be configured to close a left atrial appendage during an open surgical procedure, for example, a median sternotomy, a mini sternotomy, a thoracotomy, or a thoracoscopy. In some variations, the closure devices described here may further comprise at least one of a scope, a light, or a camera.

In some variations, the malleable member may be disposed in the third lumen. For example, the malleable member may comprise a first end and a second end, and the first end may be fixedly attached to a proximal end of the third lumen while the second end is fixedly attached to a distal end of the third lumen. In some instances, the malleable member may comprise an annealed stainless steel wire. The malleable member may also comprise a jacket around the elongate body, and the surgical closure device may further comprise a pull wire disposed in the third lumen. The pull wire may be configured to deflect a distal end of the elongate body. In some variations, the jacket may be annealed stainless steel and/or may comprise a spiral cut pattern.

The closure devices described here may further comprise a handle and a tensioning mechanism releasably coupled to the handle. For example, the tensioning mechanism may be rotatably coupled to the handle. In some instances, the closure device may further comprise a suture loop, and the tensioning mechanism may be configured to close the suture loop around tissue after it is released from the handle. In some variations, the tensioning mechanism may lock into the handle.

Also described here are systems for closing the left atrial appendage. Any of the closure devices described here may be used with any of the described systems. A system for closing the left atrial appendage may comprise a closure device and a curved guide device. The closure device may comprise a curved elongate body, a closure loop, and a handle, and the curved elongate body may comprise a stiffened proximal portion and a flexible distal portion. The stiffened proximal portion may comprise a first outer diameter, and the flexible distal portion may comprise a second outer diameter. In some variations, the first outer diameter may be greater than the second outer diameter.

The closure device may comprise a first configuration in which the handle and the closure loop may be aligned, and a second configuration in which the closure loop is rotated with respect to the handle. The curved guide device may comprise a lumen that may be configured to slideably receive the elongate body of the closure device. The curved guide device and the closure device may comprise a delivery configuration in which the curves of the guide device and the closure device have different orientations. In some embodiments, the closure device may be configured to remain in the first configuration when the closure device and the guide device are in the delivery configuration.

Methods for closing the left atrial appendage are also described here. Any of the closure devices described here may be used with any of the described methods. A method for closing the left atrial appendage may comprise positioning a closure device in a guide device. The closure device may comprise an elongate body, a closure loop, and a handle, and the elongate body may comprise a stiffened proximal portion and a flexible distal portion. The stiffened proximal portion may comprise a first outer diameter, and the flexible distal portion may comprise a second outer diameter. In some variations, the first outer diameter may be greater than the second outer diameter. In some instances, the guide device may comprise a lumen that may be configured to slideably receive the elongate body of the closure device. Moreover, in some embodiments, the closure device and the guide device may be self-orienting.

BRIEF DESCRIPTION OF THE DRAWINGS

FIGS. 2A and 2B depict embodiments of a closure device that may be used to close the left atrial appendage.

FIG. 3A depicts a distal section of an illustrative variation of a closure device with a snare loop assembly and FIGS. 3B-3F depict different orientations of the snare loop assembly.

FIGS. 10A and 10B depict variations of an embodiment of a stiffening element.

FIGS. 11A and 11B illustrate variations of an embodiment of a closure device with a malleable member. FIG. 11C is a cross-sectional view of the embodiment of the closure device shown in FIG. 11A.

FIGS. 17A-17C depict systems described here having a closure device and a guide device.

DETAILED DESCRIPTION OF THE INVENTION

Figure 1:
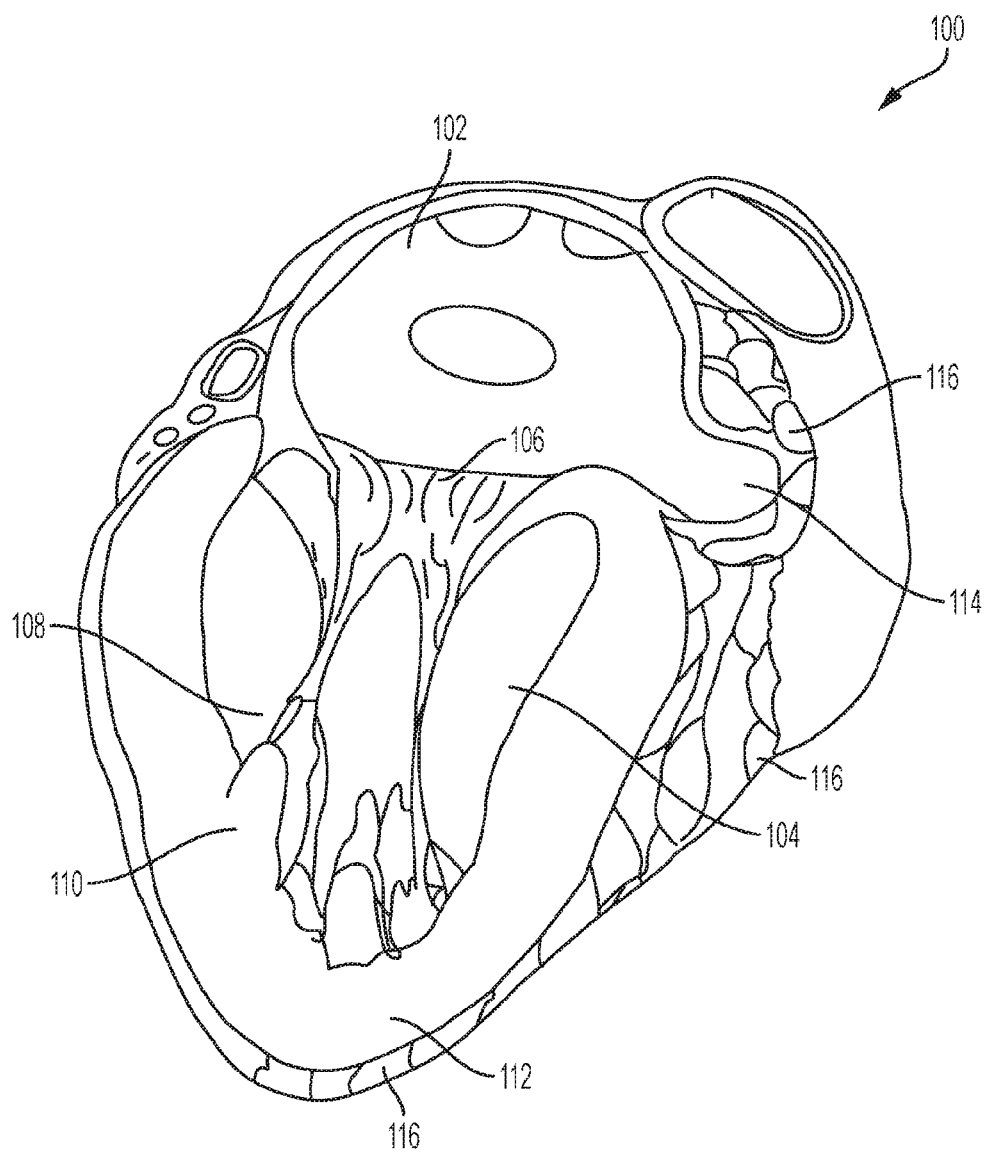
FIG. 1 provides a cross-sectional representation of a heart showing various anatomical structures.

Described here are devices, systems, and methods for closing tissue, for example, the left atrial appendage. In instances where the heart is the relevant anatomy, it may be helpful to briefly identify and describe the relevant heart anatomy. FIG. 1 is a cross-sectional view of the heart (100). Shown there is the left atrium (102) and the left ventricle (104). In between the left atrium (102) and the left ventricle (104) is the mitral valve (also known as the bicuspid valve), which is defined by a pair of mitral valve leaflets (106). The leaflets are connected to chordae tendinae (108) that are connected to papillary muscles (110). The papillary muscles join the ventricular wall (112). The left atrial appendage (114) is shown adjacent to, and is formed from, the wall of the left atrium (102).

As can be seen, the left atrial appendage (114) lies within the boundaries of the pericardium (116) and is in close proximity to the ventricular wall (112). The left atrial appendage typically has a tubular shape that approximates a cone, with a slight narrowing or neck in the plane of the orifice where it joins the left atrium (102). In patients with atrial fibrillation, the left atrial appendage (114) is the most common location for thrombosis formation, which, in time, may dislodge and cause a devastating stroke. Because stroke is the primary complication of atrial fibrillation, the left atrial appendage is frequently excluded from the left atrium in those patients undergoing procedures to treat atrial fibrillation, and is often removed or excluded at the time of other surgical procedures, such as mitral valve surgery, to reduce the risk of a future stroke. The devices and systems described here help ensure proper closure of the left atrial appendage at the neck or base of the left atrial appendage, along the anatomic ostial plane. In this way, exclusion of the entire left atrial appendage from systemic circulation may be facilitated.

I. Devices

Described here are closure devices, and methods for closing tissues using these closure devices. Generally, the closure devices comprise an elongate body and a snare loop assembly that may extend at least partially from the elongate body to capture and hold tissue. The snare loop assembly typically comprises a closure element, for example, a snare, and a suture loop releasably coupled to the snare. The snare loop assembly may be closed around tissue to temporarily or permanently close, ligate, or otherwise tighten tissue, and the suture loop may be tightened and released from the snare to hold or otherwise maintain the tissue in the closed configuration.

The closure devices described here may be suitable for advancement to the left atrial appendage using minimally invasive (e.g., through a small incision above, beneath, or through the rib cage, through an incision in the costal cartilage or the xiphoid, through a port, through the vasculature, and the like.) and surgical (e.g., median sternotomy, mini sternotomy, thoracotomy, thoracoscopy, and the like) approaches. When the closure devices are advanced through confined body spaces, such as the pericardial space, advancement or manipulation of the snare loop assembly within or through these tight spaces may result in the twisting of one or more sections of the elongate body, which may result in the rotation of the snare loop assembly. Accordingly, devices of the current invention may resist torsional forces during advancement through the body. Additionally, in some instances, it may be difficult to access a target tissue during a procedure because, for example, it may be underneath or covered by other anatomical structures. Thus, the closure devices described here may be configured to be shapeable such that they may retain a curvature in their shafts, which may assist in maneuvering the closure devices through the body, positioning the closure devices, and accessing and ligating the target tissue. Additionally, the closure devices described here may comprise elongate bodies with flexible sections or portions, which may also assist in maneuvering the closure devices through the body, positioning the closure devices, and accessing and ligating the target tissue.

The closure devices described here may include any suitable elements or combinations of elements such as those described in U.S. patent application Ser. No. 12/752,873, now U.S. Pat. No. 9,198,664, entitled "Tissue Ligation Devices and Controls Therefor" and filed on Apr. 1, 2010, the contents of which are incorporated by reference herein in its entirety. In addition to having an elongate body and a snare loop assembly, the closure devices typically comprise one or more mechanisms for controlling manipulation and advancement of the elongate body and/or the snare loop assembly. For example, a handle or other control mechanism (e.g., a surgical master-slave robotic system) may be used to control and actuate the snare loop assembly through the elongate body. The handle or other control mechanism may change the snare loop assembly between a delivery, or "closed," configuration and a deployed, or "open," configuration, and vice versa. Placing the snare loop assembly in a closed configuration may allow for a low-profile advancement of the snare loop assembly to a target location and/or may allow the snare loop assembly to close around a target tissue. Conversely, placing the snare loop assembly in an open configuration may allow the snare loop assembly to be placed around one or more target tissues and/or may allow the snare loop assembly to release one or more target tissues previously closed by the snare loop assembly.

In use, a distal end of an elongate body may be advanced into the body toward a target tissue (e.g., the left atrial appendage). During advancement, the snare loop assembly may be in a closed configuration to help prevent the snare loop assembly from snagging or catching on tissue or other obstructions. Once the distal end of the elongate body has reached a location at or near the target tissue, the snare loop assembly may be opened to a deployed configuration. The snare loop assembly may then be advanced, moved, or otherwise manipulated to encircle at least a portion of the target tissue. The snare loop assembly may then be closed around the encircled tissue to close, ligate, or otherwise restrict the target tissue. The snare loop assembly may be re-opened, repositioned, and re-closed as necessary. In some instances, a suture loop or other restricting device may be tightened and released from the closure device to maintain the target tissue in a closed fashion. To remove the closure device from the body, the snare loop assembly may again be opened to release the target tissue (the suture loop or other restricting device may remain in place) such that the snare loop assembly and the elongate body may be withdrawn. Once the target tissue is released, the snare loop assembly may be closed to facilitate a low-profile withdrawal. In variations where the closure device comprises a tensioning device or mechanism, the tensioning device or mechanism may be used to release the suture loop from the snare loop assembly and/or tighten the suture loop.

The closure devices may contain one or more additional features, as will be described in more detail below. In some variations, the elongate body may comprise multiple sections which may have one or more defining characteristics, for example, a particular stiffness, cross-sectional shape, diameter, etc. Utilizing a closure device with multiple sections may allow a user to more easily maneuver the device through the body and may provide more control over the device during a closure procedure. In some instances, the elongate body may be shapeable, meaning that the elongate body may be manipulated (e.g., bent) and may retain the manipulated shape until a user or other applied force (e.g., from tissue within the body) further modifies it. These and other features will be described in more detail below. It should be appreciated that the closure devices described here may comprise any combination of these features and the other features described below.

Figure 2A:
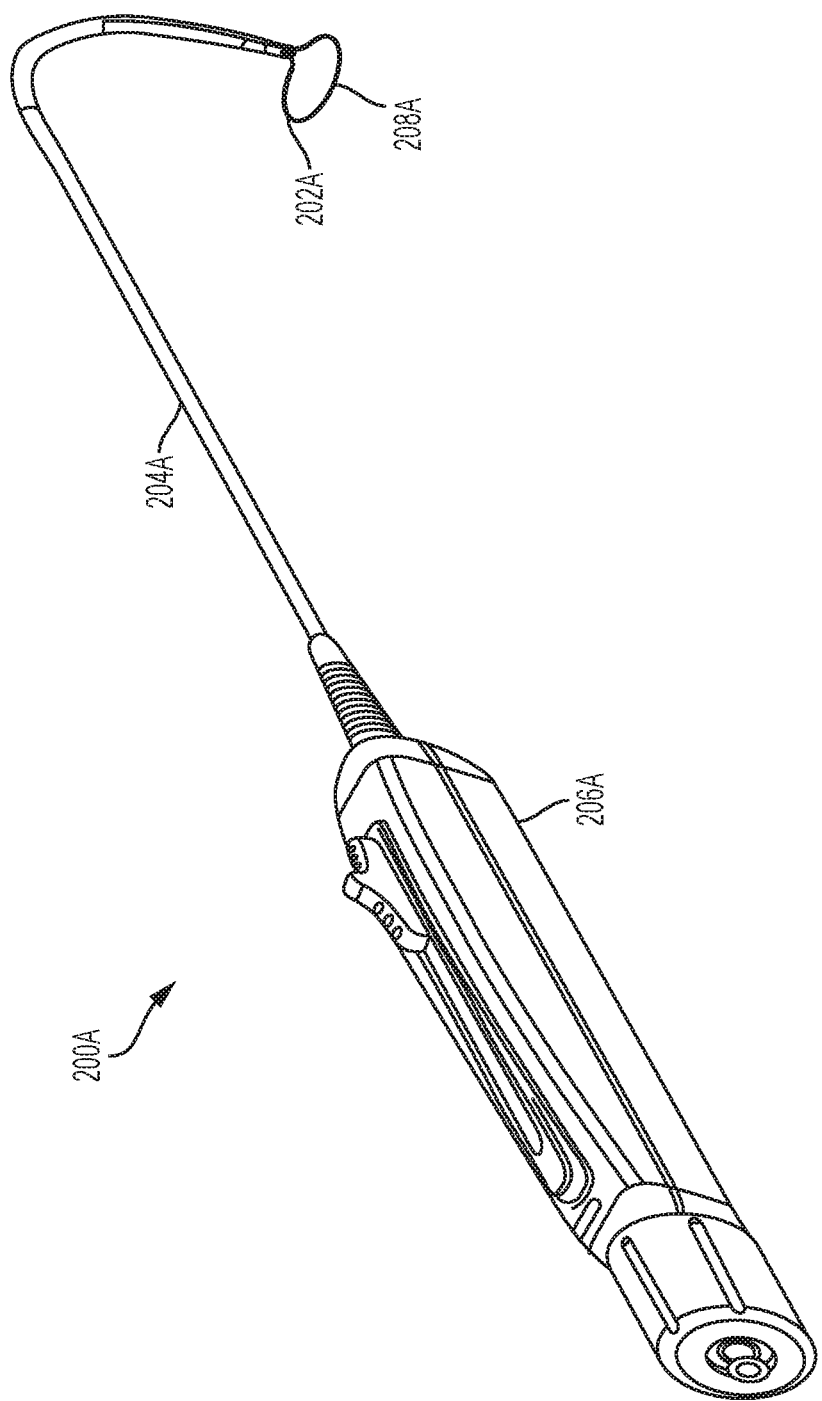

FIGS. 2A and 2B depict exemplary devices (200A, 200B) that may be used to close the left atrial appendage. Shown there are a snare loop assembly (202A, 202B), an elongate body (204A, 204B), and a handle (206A, 206B). As noted above, the handle (206A, 206B) may be used to control and actuate the snare loop assembly (202A, 202B) through the elongate body (204A, 204B) in order to move the snare loop assembly (202A, 202B) between a closed configuration and an open configuration, and vice versa. In some variations, and as shown in FIG. 2B, the handle may comprise a suture tensioning element (210) that may deploy and/or tighten a suture loop. When in an open configuration, the snare loop assembly (202A, 202B) and the elongate body (204A, 204B) may form a continuous loop (208A, 208B) (e.g., such that the snare loop assembly (202A, 202B) and the elongate body (204A, 204B) may fully encircle tissue placed in the loop (208A, 208B)). When moved from the open configuration to the closed configuration, the size of the loop (208A, 208B) may be reduced as some or all of the snare loop assembly (202A, 202B) is withdrawn into the elongate body (204A, 204B). Individual components of the closure devices described here are described in more detail below.

Snare Loop Assembly

As mentioned above, the snare loop assemblies of the closure devices described here may be used to temporarily close or restrict one or more target tissues. Generally, the snare loop assembly comprises a closure element, e.g., a snare, and a suture loop releasably attached to the closure element. In some variations, the snare loop assembly may comprise a retention member at least temporarily connecting the closure element and the suture loop. FIG. 3A shows a distal section of an illustrative variation of a closure device (300) comprising a snare loop assembly (302), an elongate body (304), and a tip (306) coupled to the elongate body (304). As shown there, the snare loop assembly (302) may comprise a snare (308), a suture loop (310), and a retention member (312), and may be disposed relative to the elongate body (304) such that at least a portion of the snare loop assembly (302) extends from the elongate body (304) (e.g., via tip (306)). The snare loop assembly (302) is shown in FIG. 3A in an open configuration, and the portion of the snare loop assembly (302) extending out of elongate body (304) may form a loop (314) having an aperture (316) therethrough. The loop (314) and the corresponding aperture (316) may be defined by one or more components of the snare loop assembly (302) (e.g., the snare) and may be suitable for encircling tissue such as the left atrial appendage. Generally, the snare (308) may be used to open and close the snare loop assembly (302). In some instances, the retention member (312) may be configured to releasably couple the suture loop (310) and the snare (308) and may be configured to release the suture loop (310) from the snare loop assembly (302) upon application of a sufficient force to suture loop (310).

In variations of snare loop assemblies comprising a snare, the snare may be at least partially moveable to change a snare loop assembly between open and closed configurations. Generally, a portion of the snare may be housed in the elongate body, and another portion of the snare may extend outside of the distal end of the elongate body to at least partially define the loop and aperture of the snare loop assembly. In some variations, one end of the snare may be fixed relative to one or more portions of the closure device, while the other end may be advanced or retracted through the elongate body. Movement of the free end of the snare may change the amount of the snare loop assembly that is disposed outside of elongate body, and thus may change the size (e.g., diameter, circumference, area, etc.) of the loop and the aperture defined thereby. Specifically, advancement of the snare through the elongate body may increase the size of the loop and aperture of the snare loop assembly, while retraction of the snare may decrease the size of the loop and aperture of the snare loop assembly. The free end of the snare may be manipulated in any suitable manner. In some variations, the snare may be attached directly to one or more portions of the handle. In other variations, a hypotube, rod, or other rigid structure may be attached to the free end of the snare. This structure may in turn be moved by the handle, which may help facilitate advancement or withdrawal of the snare through the elongate body.

The closure elements or snares described here may be made of any suitable material or combination of materials. For example, in some variations, the snare may be made from a shape-memory material, such as a shape-memory alloy (e.g., a nickel titanium alloy, etc.), or may be made from stainless steel, polyester, nylon, polyethylene, polypropylene, combinations thereof, and the like. In variations where the snare is made from a shape-memory material, the snare may be configured to take on a particular shape or configuration when the snare loop assembly is placed in an open configuration, but may still be at least partially withdrawn into the elongate body to place the snare loop assembly in a closed configuration. For example, the snare may form a generally circular, teardrop-shaped, oval or ellipsoid, or triangular loop when the snare loop assembly is placed in an open configuration.

Figure 3B:
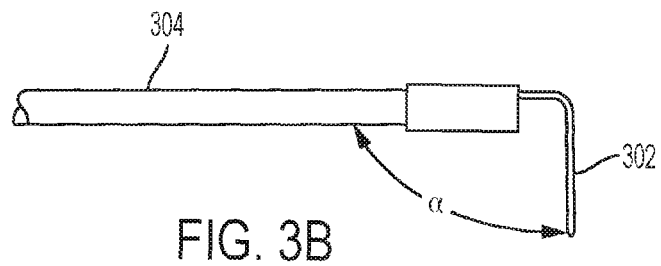
Figure 3C:
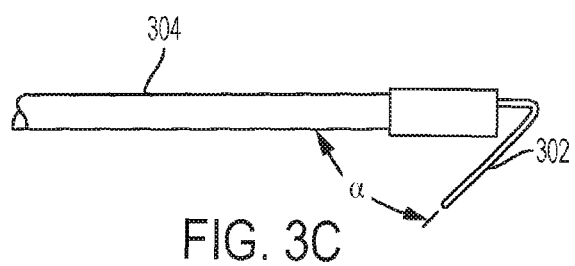
Figure 3D:
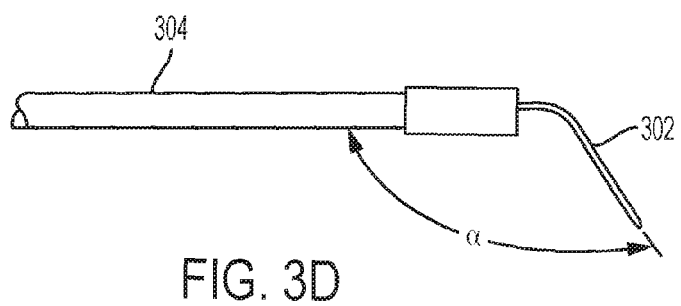
Figure 3E:
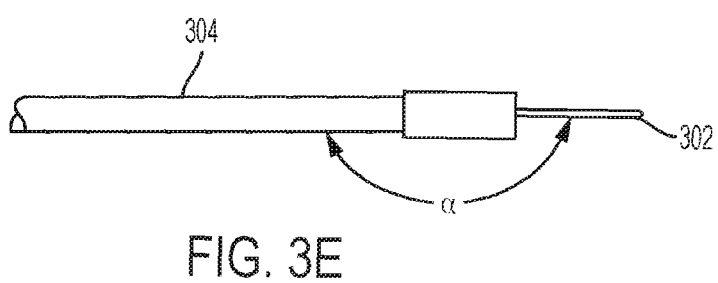
Figure 3F:
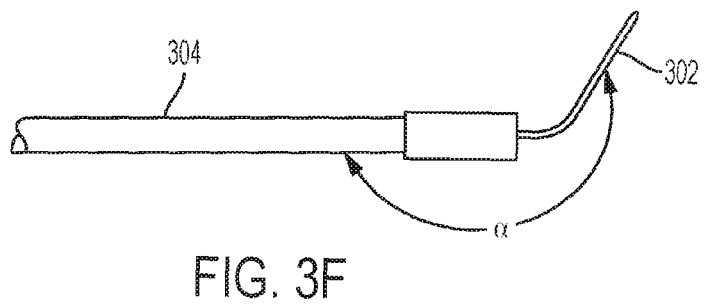

Furthermore, in some variations, the snare loop assembly may be angled relative to the elongate body. As shown in FIGS. 3A and 3B, the snare loop assembly (302) is in a plane that is approximately perpendicular to the distal end of the elongate body (304), however, the plane of the snare loop assembly (302) may be varied over a wide range of angles (a), as depicted in FIGS. 3B-3F. For example, the angle (a) formed between the plane of the snare loop assembly (302) and the distal end of the elongate body (304) may be between about 5 degrees and about 85 degrees (FIG. 3C), may be about 90 degrees (FIGS. 3A and 3B), may be between about 95 degrees and about 175 degrees (FIG. 3D), may be about 180 degrees (FIG. 3E), or may be between about 185 degrees and about 270 degrees (FIG. 3F). In some variations, the angle (a) formed between the plane of the snare loop assembly (302) and the distal end of the elongate body (302) may be between about 5 degrees and about 45 degrees. Angling the snare relative to the elongate body may aid the snare in capturing tissue, as angling may better position the snare relative to tissue as the closure device is moved in the body.

Suture Loop

The snare loop assemblies described here may also comprise a suture loop for maintaining tissue in a closed manner. Generally, the suture loop may be releasably attached to the snare, for example, via a retention member, as will be described in more detail below. Furthermore, the suture loop may comprise a suture knot, but need not. This suture knot may be any suitable knot, including, but not limited to, a slip knot (e.g., a one-way slip knot) or a Meltzer knot. In some variations, at least a portion of the knot may be held within the tip of the elongate body. In other variations, the suture knot at least partially extends from the tip of the elongate body or may be positioned outside of the tip and may be temporarily held in fixed relation to the elongate body. When the suture loop comprises a suture knot, the suture loop may comprise a loop portion, a suture knot, and a tail extending from the suture knot. The suture tail may be pulled through the suture knot to reduce the diameter of the loop portion.

In variations where the suture loop comprises a slip knot, suture may be advanced or withdrawn through the slip knot to change the size of the suture loop. In instances where the suture knot is held within or against a tip of the elongate body, the suture knot may not move while the size of the suture loop is changed. This may help prevent the closure device from damaging tissue. In some variations, the suture loop may comprise a unidirectional locking structure. In these variations, the unidirectional locking structure may be any structure capable of being advanced along the suture in one direction but resisting movement in a second direction. In these variations, the locking structure may be advanced over a portion of the suture loop to help lock a suture knot in place. For example, in some variations, the unidirectional locking structure may comprise a bead or a mechanical structure that is placed at least partially around the suture. In these variations, the bead may comprise one or more teeth or projections that allow the bead to be advanced along the suture in one direction, but prevent or resist movement in the opposite direction. The locking structure may be advanced via one of the closure devices described here, or it may be advanced by a separate device after the suture loop has been released from the closure device.

The suture loop may be made from any suitable material useful in tissue exclusion or closure. For example, it may be made of a biodegradable material (e.g., polylactic acid, polyglycolic acid, polylactic-co-glycolic acid, etc.), or it may be made of a non-biodegradable material (e.g., metal, steel, polyester, nylon, propylene, silk, combinations thereof, etc.).

Retention Member

When the snare loop assemblies described here comprise a retention member releasably coupling the snare and the suture loop, the retention member may be any suitable member, such as dual-lumen tubing. In some variations, one lumen may have a slit, perforation, or other opening along its length, which may allow the suture to pass therethrough when it is ready to be deployed. The slit need not extend or be continuous along the entire length of the retention member. In some variations, the slit may have prongs or arms along its length to help capture and retain the suture in the retention member. In other variations, the slit may be covered at spaced-apart locations with a biodegradable polymer, which may temporarily tack or hold down the suture. Of course, in still other variations, the retention member does not comprise a slit, and instead comprises some other type of retention mechanism, such as the prongs or tacks described just above. In yet other variations, there are no slits or openings in the retention member, and the suture loop is released upon removing or withdrawing the retention member.

Elongate Body

As mentioned briefly above, the closure devices described here generally comprise an elongate body. The elongate body may connect the distal end of the snare loop assembly and the handle or actuating mechanism while still allowing for control of the snare loop assembly through the elongate body. Specifically, at least a portion of some of the snare loop assembly components may be housed within the elongate body and may be connected to the handle through the elongate body. In some variations, portions of the elongate body may be flexible, which may help facilitate movement and navigation of the elongate body through tissue. The elongate body may comprise various sections or portions with different characteristics, for example, different diameters, cross-sectional shapes, stiffnesses, materials, and the like, which may increase the steerability and maneuverability of the closure device.

Geometry

Figure 4:
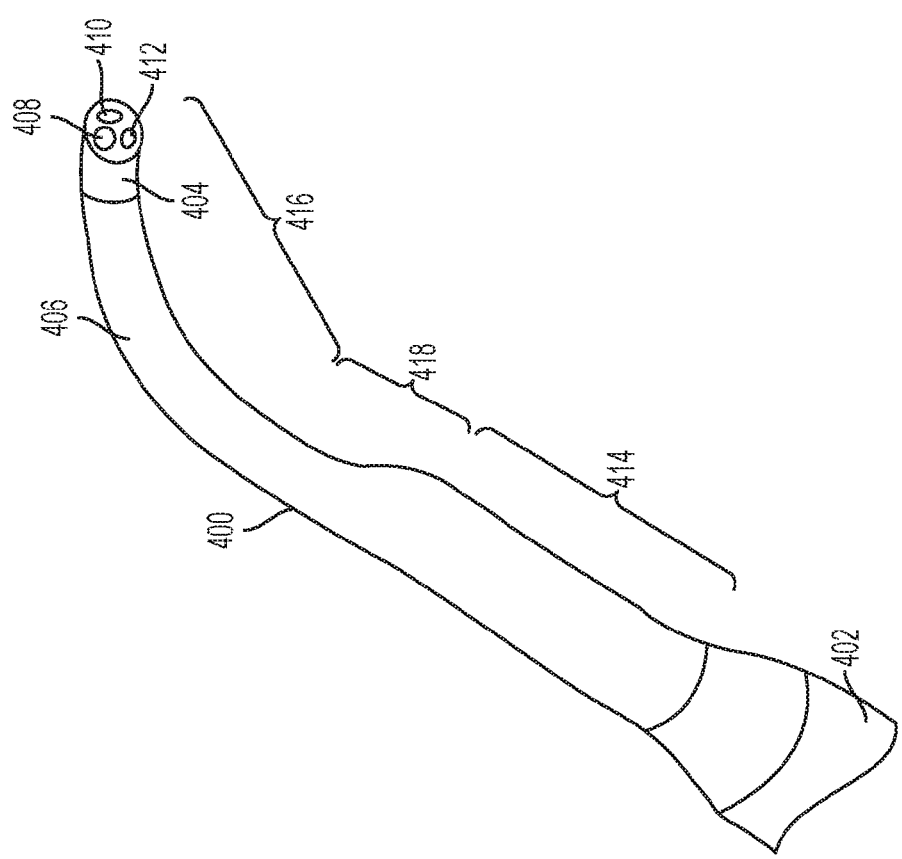
FIG. 4 depicts an illustrative variation of an elongate body suitable for use with the closure devices described here.
Figure 18:
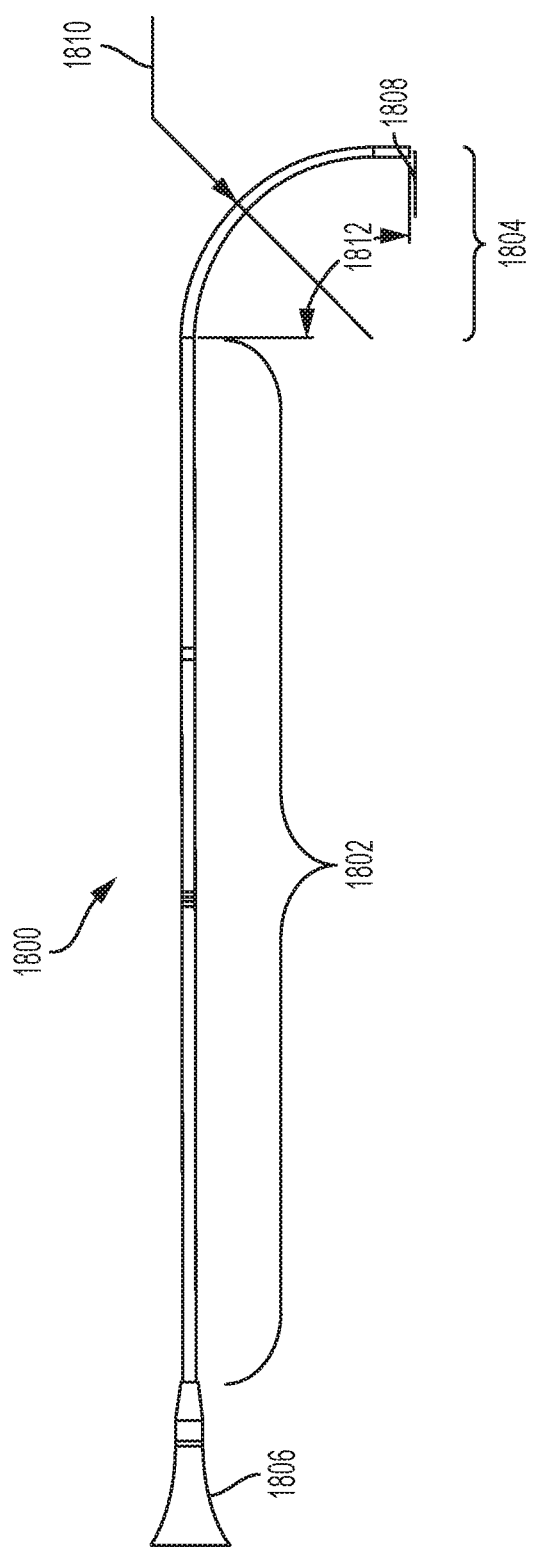
FIG. 18 illustrates an embodiment of a closure device comprising a curved distal segment.

FIG. 4 shows an illustrative variation of an elongate body suitable for use with the closure devices described here. Shown there is an elongate body (400) attached to a handle (402). The elongate body (400) may comprise a curved segment (406), a first lumen (408), a second lumen (410), and a third lumen (412). The curved segment (406) may assist in guiding the distal end of the closure device to the target tissue, for example, the base of the left atrial appendage, and may have an angle and radius selected to facilitate appropriate positioning at the target tissue, for example, within the pericardial space. For example, FIG. 18 depicts a variation of an elongate body (1800) comprising a proximal straight segment (1802), a distal curved segment (1804) with a radius (1810) and an angle (1812), a handle (1806), and an illustrative loop (1808) (e.g., a snare loop, a suture loop, a snare loop assembly). The angle (1812) may be measured from a plane perpendicular to the longitudinal axis of the proximal straight segment (1802) to the plane formed by the loop (1808). In some variations, the angle (1812) may be about 20 degrees to about 100 degrees and the radius (1810) may be about 2.00 inches (5.08 cm) to about 6.00 inches (15.24 cm). In some instances, the angle (1812) may be about 45 degrees to about 90 degrees and the radius (1810) may be about 2.00 inches (5.08 cm) to about 4.00 inches (10.16 cm). In some variations, the angle (1812) may be about 86 degrees to about 88 degrees and the radius (1810) may be about 3.10 inches (7.87 cm) to 3.40 inches (8.64 cm). In some of these variations, the angle (1812) may be about 87 degrees and the radius may be about 3.30 inches (8.38 cm). In other variations, the angle (1812) may be between about 84 degrees and 86 degrees, and the radius (1810) may be between about 2.60 inches (6.60 cm) and about 2.90 inches (7.37 cm). In some of these variations, the angle (1812) may be about 85 degrees and the radius may be about 2.8 inches (7.11 cm). As mentioned above, in some instances, the configuration of the distal curved segment (1804), including the angle (1812) and radius (1810), may facilitate positioning the closure device relative to the target tissue. However, other features described herein, which may affect the flexibility and torqueability of the elongate body (e.g., cross-sectional shape, cross-sectional diameter/height, number of flexible portions, proximal stiffening elements), may also contribute to the ability to advance and position the closure device. Thus, the features described herein that may affect the flexibility and torqueability of the elongate body may determine what angle (1812) and radius (1810) may be most desirable for a particular procedure.

Turning back to FIG. 4, in some variations, the closure device may comprise one or more mechanisms that may act or function to change the shape of the elongate body (400), as will be described in more detail below. In instances where the elongate body (400) comprises one or more curved segments (406), a tube, mandrel, or other straightening mechanism (not shown) may be used to temporarily straighten the elongate body. The elongate body may be made of any suitable material, for example, one or more polymers (e.g., polyether block amide, polyethylene, silicone, polyvinyl chloride, latex, polyurethane, PTFE, nylon, and the like). While shown in FIG. 4 as having a single curved segment (406), the elongate body (400) may not have any curved segments, or it may have multiple curved segments along its length.

The elongate body may comprise any suitable length, and the length of the elongate body may vary depending on the type of procedure being performed. For example, the length of the elongate body may generally be between about 6 inches (15.24 cm) and about 19 inches (48.26 cm). As used herein, "about" means ±5%. During a minimally invasive procedure, the elongate body may have to travel a further distance through the body to reach a target tissue than when the device is used in a surgical procedure. Thus, it may be desirable to use a longer elongate body when using the device in a minimally invasive procedure and a shorter elongate body when using the device in a surgical procedure. For instance, it may be desirable to use an elongate body with a length between about 15 inches (38.10 cm) and about 18 inches (45.72 cm) during a minimally invasive procedure and an elongate body with a length between about 6 inches (15.24 cm) and about 12 inches (30.48 cm) during a surgical procedure. In some instances, it may be desirable to use an elongate body with a length between about 15.5 inches (39.37 cm) and about 16.5 inches (41.91 cm) during a minimally invasive procedure and an elongate body with a length between about 9.5 inches (24.13 cm) and about 10.5 inches (26.67 cm) during a surgical procedure.

Moreover, the elongate body may comprise any suitable cross-sectional shape, for example, circular (as depicted in FIG. 4), oval, D-shaped, triangular, and the like. In some embodiments, the cross-sectional shape of the elongate body may vary along its length. In some variations, the elongate body may be described as having multiple portions, each portion corresponding to a specific cross-sectional shape. For example, the elongate body may comprise a proximal portion with a first cross-sectional shape (e.g., circular) and a distal portion with a second cross-sectional shape (e.g., D-shaped). Of course, the elongate body may comprise any suitable number of portions, e.g., two, three, or four portions, and the length of each portion may be the same as or different from the other portions. In some variations, a tip (404) may be coupled to the elongate body.

The elongate body may also comprise any suitable outer diameter, and, in some instances, the outer diameter of the elongate body may also vary along its length. Typically, the outer diameter of the elongate body may be between about 0.120 inches (3.048 mm) and about 0.220 inches (5.588 mm); however, it may be desirable to restrict the largest outer diameter of the elongate body so that it can fit through a guide device having a specific diameter. For example, in instances in which the closure device is used during a minimally invasive procedure, it may be desirable to limit the outer diameter of the elongate body such that it may fit through 13-French percutaneous tubing.

As mentioned above, and depicted in FIG. 4, the elongate body may comprise multiple portions with different diameters. For example, the elongate body (400) may comprise a proximal portion (414) with a first diameter and a distal portion (416) with a second diameter. As shown in FIG. 4, the first diameter may be larger than the second diameter; however, this need not be the case. In some instances, the elongate body may comprise at least two, three, four, or five portions with different diameters. In some variations, the portions of the elongate body having different diameters may correspond to (i.e., may have the same length and be located at the same location along the length of the elongate body) the portions described above having different cross-sectional shapes. Of course, this need not be the case. Moreover, in instances in which the cross-section is D-shaped, a height will be referred to instead of a diameter. In some embodiments, the height may be larger than the diameter of one or more other portions, whereas in other embodiments the height may be smaller than the diameter of the other portions of the elongate body.

The elongate body may further comprise one or more transitions connecting the portions of the elongate body comprising different diameters or different cross-sectional shapes. These transitions may have any suitable length. In some variations, the transitions may connect two portions of the elongate body that have both different diameters (or heights) and different cross-sectional shapes. Turning back to FIG. 4, in the embodiment shown there, the elongate body (400) comprises a transition (418) that connects the proximal portion (414) (having the first diameter) and the distal portion (416) (having the second smaller diameter). While the transition (418) is depicted in FIG. 4 as beveled or tapered along only a portion of the circumference of the elongate body (i.e., the underside of the elongate body), it should be appreciated that it may be beveled or tapered along any portion of or along all of the circumference of the elongate body. Moreover, in some variations, the transition (418) may not be beveled or tapered at all and may instead create a shoulder or a ledge (using right angles or the like, as will be described below). In some instances, the diameter or height of the elongate body may change gradually along its length such that a discrete transition region is not apparent.

Lumens

The elongate bodies described here may have any suitable number of lumens. As used herein, "lumen" may refer to any bore or passageway extending through a length of the elongate body or other portion of the closure device (e.g., through a handle). It should be appreciated that a lumen need not be entirely enclosed (i.e., the lumen may comprise one or more slots, slits, gaps, or other openings along some or all of the length of the lumen). The elongate body may comprise one, two, three, four, or five or more lumens. Some or all of the lumens may extend entirely through the elongate body (i.e., from the proximal end of the elongate body to the distal end of the elongate body). Other lumens may pass through only a portion of the elongate body (e.g., from one end to an intermediate point along the elongate body, or between two intermediate points along the elongate body).

The various components of the snare loop assembly may be housed within any lumen or lumens of the elongate body. For example, in some variations, all of the components of the snare loop assembly may be housed in a single lumen. In other variations, different portions of the snare loop assembly may be at least partially housed in different lumens. For example, the free end of the suture loop may pass to the handle through a first lumen, while the free end of the snare may pass to the handle through a second lumen. In some variations, there may be excess suture housed within the elongate body, and this excess suture may be housed in any suitable lumen. For example, the excess suture may be held in the same lumen as the free end of the suture loop, in the same lumen as the free end of the snare, or in an altogether different lumen.

Figure 5B:
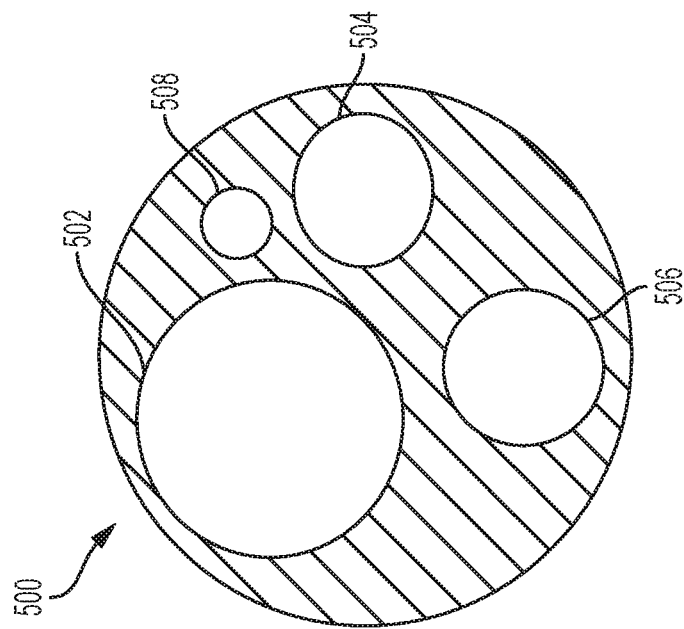
FIGS. 5A and 5B are cross-sectional views of variations of an elongate body suitable for use with the closure devices here.
Figure 5A:
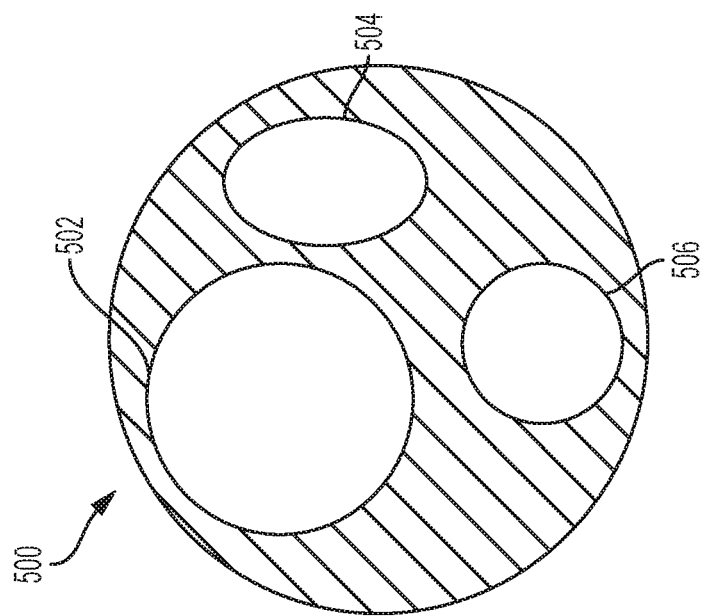

FIGS. 5A and 5B are cross-sectional views depicting the lumen configurations of illustrative elongate bodies. FIG. 5A depicts an exemplary elongate body (500) comprising a first lumen (502), a second lumen (504), and a third lumen (506). In this embodiment, the first lumen (502) may house the free or moving leg of the snare, and a portion of the suture loop and excess suture if necessary; the second lumen (504) may house the fixed leg of the snare and a portion of the suture loop; and the third lumen (506) may house a guide device, for example, a guide wire. As is depicted in FIG. 5A, the lumens may have different diameters and cross-sectional shapes. For example, referring to the embodiment depicted in FIG. 5A, the first lumen (502) and the third lumen (506) may be circular, whereas the second lumen (504) may be oval. The first lumen (502) may have a larger diameter than the semi-major axis of the second lumen (504), and the semi-major axis of the second lumen (504) may be larger than the diameter of the third lumen (506). In some instances, the diameter of the first lumen (502) may be between about 0.07 inches (1.78 mm) and about 0.08 inches (2.03 mm), the semi-major axis of the second lumen (504) may be between about 0.05 inches (1.27 mm) and about 0.06 inches (1.52 mm), and the diameter of the third lumen may be between about 0.04 inches (1.02 mm) and 0.05 inches (1.27 mm).

FIG. 5B depicts another variation of the elongate body (500) comprising four lumens (502, 504, 506, 508). In this embodiment, the second lumen (504) may house a portion of the suture, and the fourth lumen (508) may house a leg of the snare. In some variations, the fourth lumen (508) may also house a lockwire configured to anchor a leg of the snare to the elongate body (500). In some embodiments, the snare may be releasable, and the lockwire may optionally release the leg of the snare. Additionally, the second and third lumens (504, 506) may have the same or very similar diameters, which may be greater than the diameter of the fourth lumen (508). In this variation, the diameter of the fourth lumen may be between about 0.02 inches (0.508 mm) and about 0.03 inches (0.762 mm). While all the lumens are depicted as circular, this need not be the case, and the lumens may have any suitable shape.

While the lumens are depicted in specified locations within the elongate body, the lumens may be positioned in any location within the elongate body (i.e., their centers may be moved and their locations shifted); however, it may be desirable to maintain a minimum wall thickness between the lumens to prevent breakthrough. For example, in some variations, it may be necessary to heat the elongate body after it is extruded or otherwise manufactured to attach, insert, or bond stiffening or other elements to the closure device, as will be described in more detail below. Heating the elongate body may cause the lumens to shift locations or change in size. In some instances, a portion of the material separating the two lumens may sever such that the lumens converge or otherwise come together forming one lumen instead of two. In order to decrease the likelihood of this breakthrough, it may be desirable to maintain a minimum distance between the lumens during extrusion and/or heating. Additionally, as described above, in some variations, a portion of the elongate body may comprise a D-shaped cross-section, which may be created by cutting, shaving, skiving, or otherwise removing a portion of the elongate body. In these variations, maintaining a minimum wall thickness between the lumens may prevent the lumens from shifting during heating and becoming severed when the elongate body is cut to create the D-shape. Accordingly, in some variations, it may be desirable to maintain at least about a 0.005 inch (0.127 mm) wall thickness between the lumens.

Additionally, in some variations, the lumens may comprise a lining or a coating designed to reduce the frictional forces between the internal surface of the lumens and the components housed within them. The small size of the lumens, their relative locations, the materials used, and the precision required to fabricate the elongate body may result in manufacturing variations (e.g., different frictional characteristics inside the lumens) between different lots and/or different manufacturers. These variations may lead to an inconsistent user experience and may result in frustration with the closure device and/or improper usage. For example, if the frictional forces between the internal surface of the suture lumen and the suture vary, the user may be required to apply different amounts of force to tighten the suture each time the device is used. This may result in over or under tightening of the suture around the tissue. Accordingly, in some embodiments, the suture lumen may comprise a friction-reducing lining or coating (e.g., a polytetrafluoroethylene (PTFE)). It may be desirable to include a friction-reducing lining in any and/or all of the lumens of the elongate body, as doing so may result in a more consistent and predictable user experience.

Figure 6A:
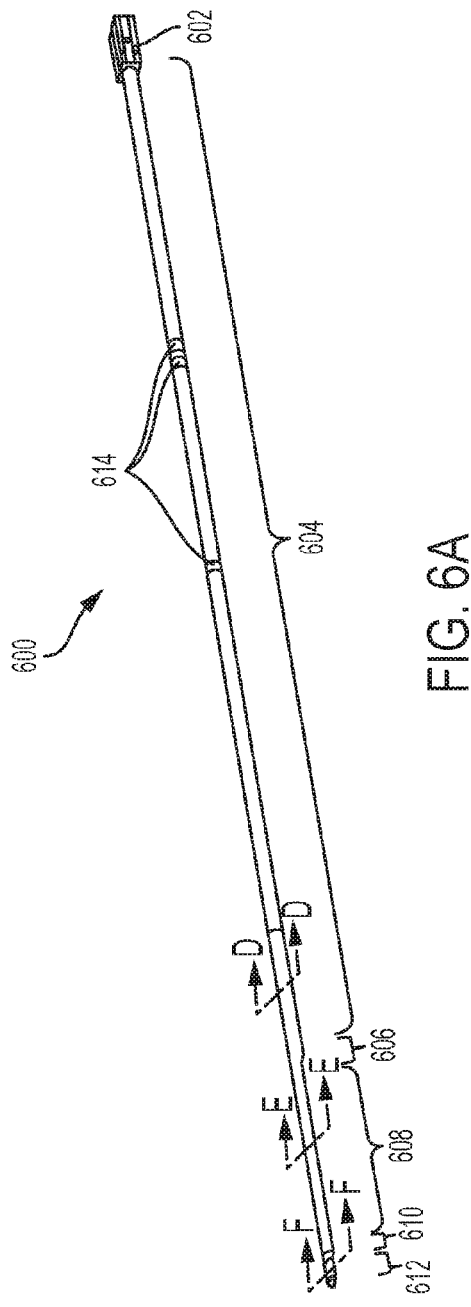
FIG. 6A depicts a perspective view and FIGS. 6B and 6D-6F depict cross-sectional views of an embodiment of an elongate body of the closure devices described here.
Figure 6G:
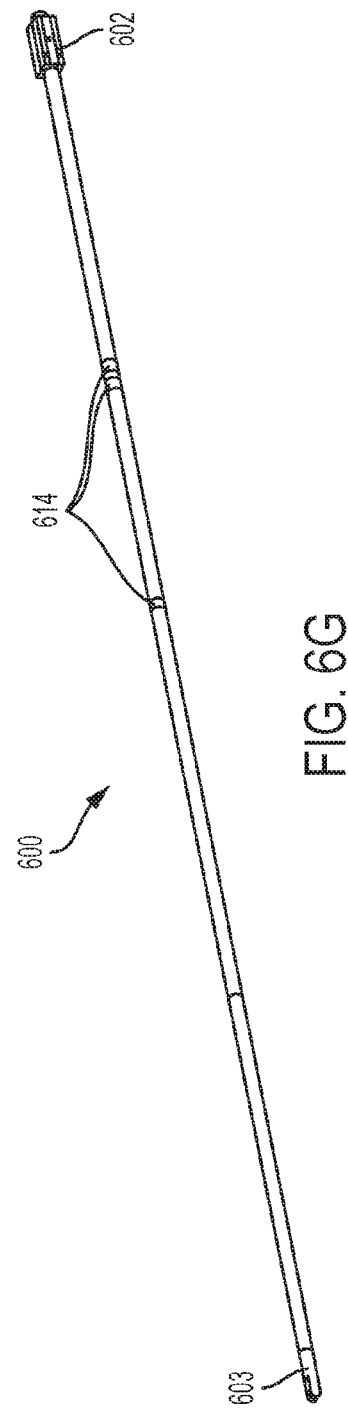
FIG. 6G depicts a perspective view of the embodiment shown in FIG. 6A with a tip.

Turning back now to features of the elongate body, FIG. 6A depicts another variation of an elongate body (600) comprising a collar (602), a first portion (604), a first transition (606), a second portion (608), a second transition (610), a third portion (612), and markers (614). FIG. 6G depicts the variation of the elongate body (600) shown in FIG. 6A with a tip (603) coupled to the distal end of the elongate body (600). As mentioned above, each portion of the elongate body may have different characteristics, for example, each portion may correspond to a particular cross-sectional shape, diameter or height, and/or stiffness. In the embodiment depicted in FIG. 6A, each portion of the elongate body corresponds to a particular cross-sectional shape or diameter of the elongate body and, in some instances, to both a particular cross-sectional shape and a particular diameter. The first transition (606) connects the first portion (604) to the second portion (608), and the second transition (610) connects the second portion (608) to the third portion (612). It should be appreciated that while the elongate body (600) is depicted with three portions and two transitions, it could have any suitable number of portions (e.g., two, three, four, five, six, seven, or eight) and transitions (e.g., one, two, three, four, five, six, or seven).

Figure 6B:
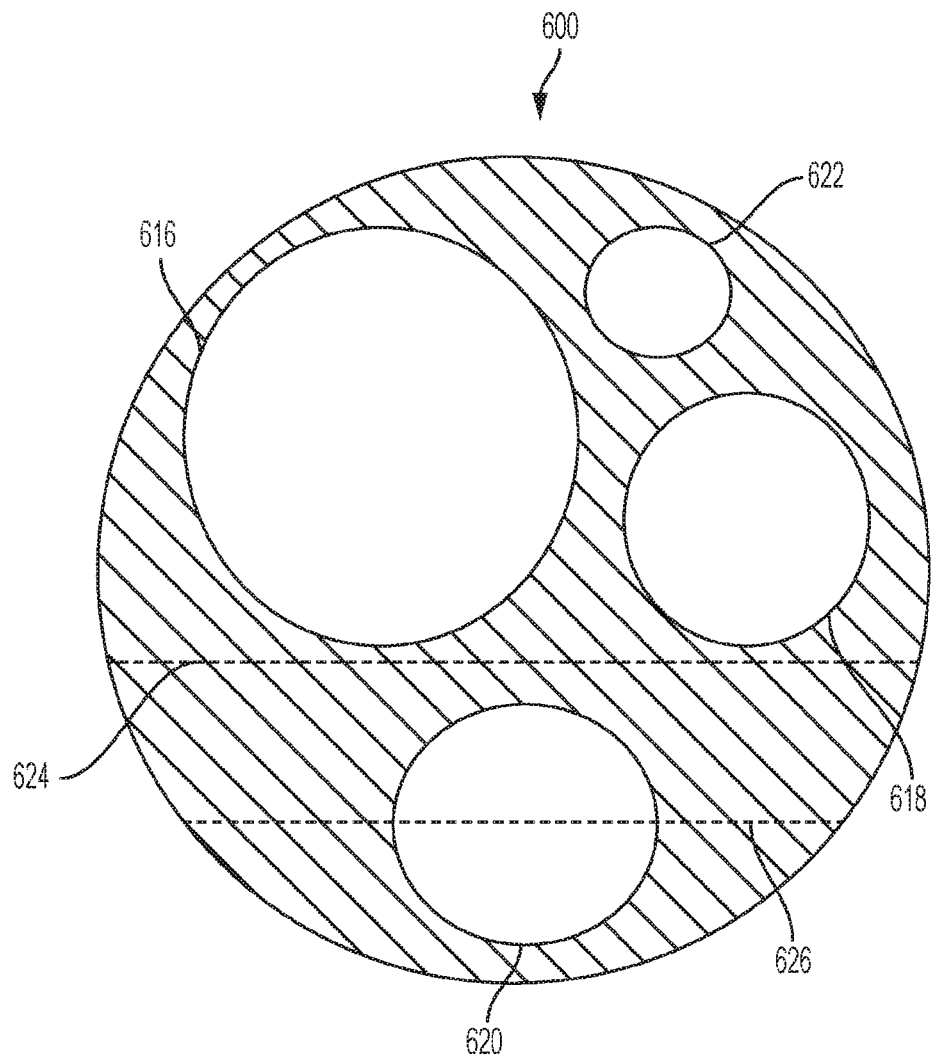
Figure 6C:
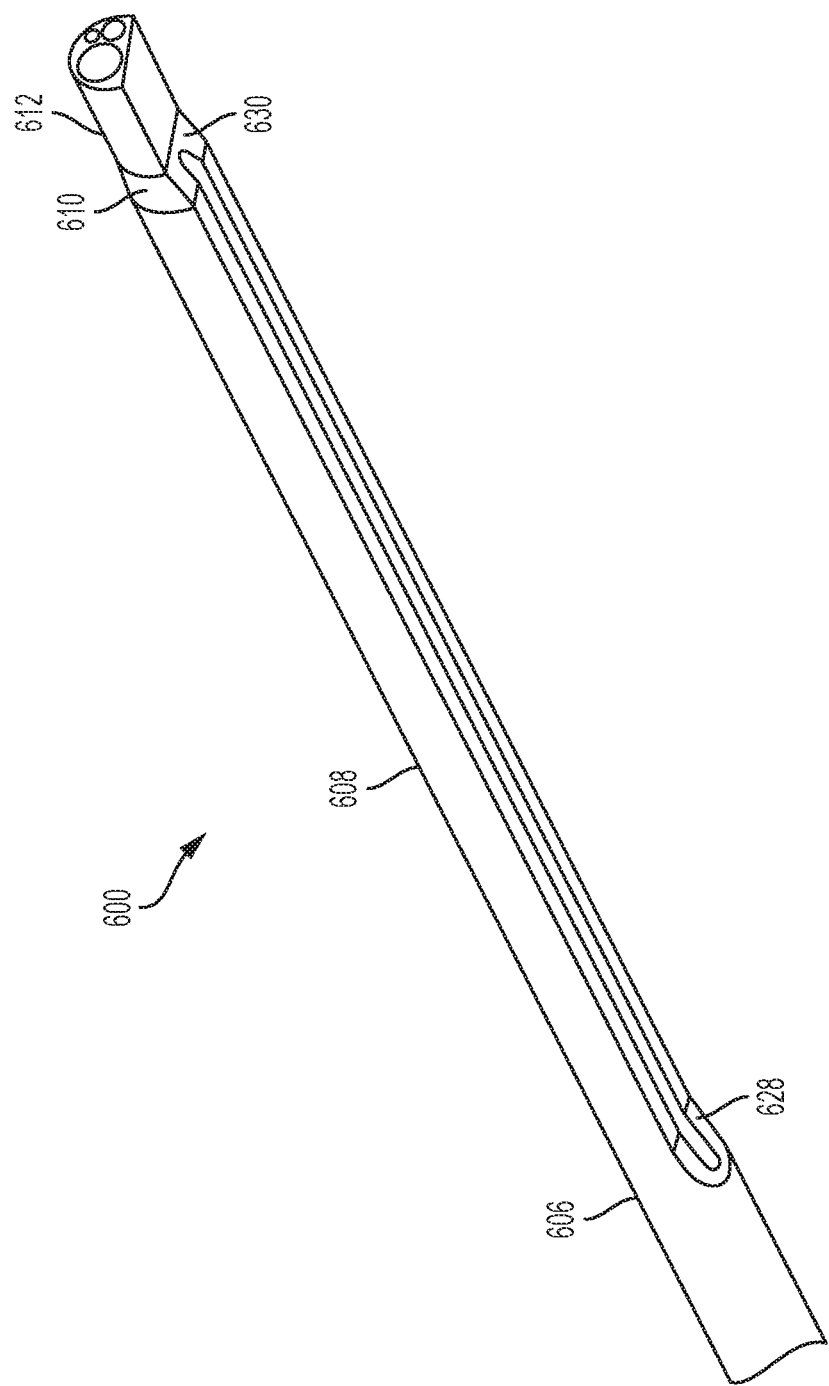
FIG. 6C depicts a distal end of an embodiment of an elongate body.
Figure 6E:
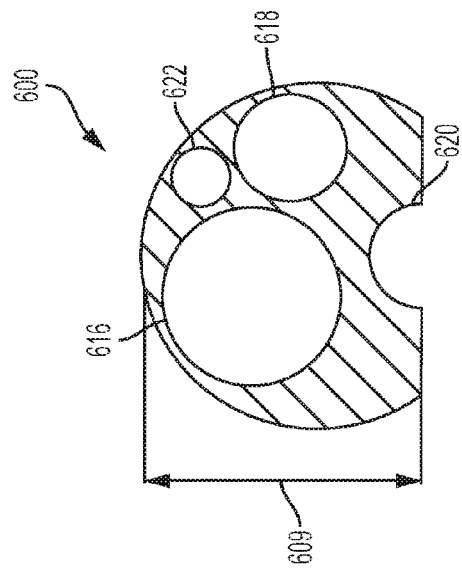
Figure 6F:
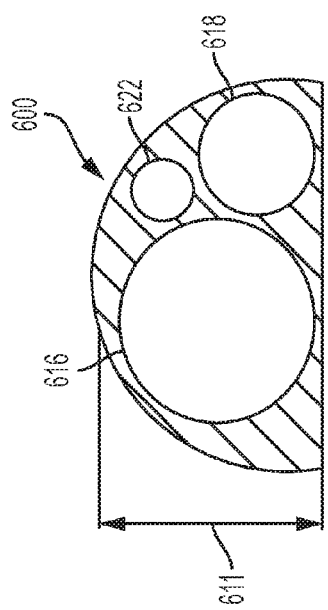
Figure 6D:
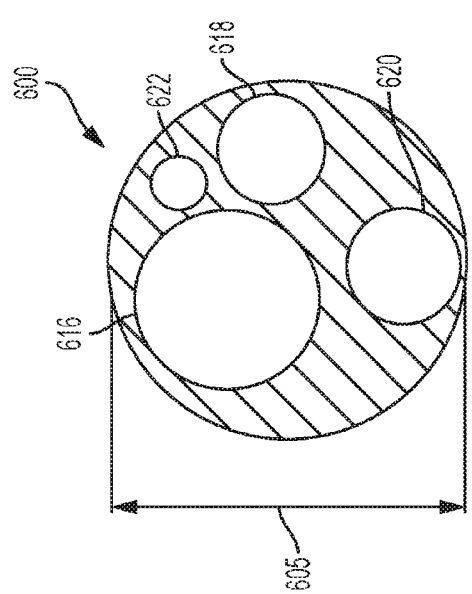

FIGS. 6D-6F depict cross-sectional views of the first, second, and third portions (604, 608, 612) along lines DD, EE, and FF of FIG. 6A, respectively. As shown in FIGS. 6D-6F, the first portion (604) comprises a cylindrical cross-section with a diameter (605), the second portion (608) comprises a D-shaped cross-section with a first height (609), and the third portion (612) comprises a D-shaped cross-section with a second height (611). In this variation, the diameter (605) of the first portion (604) may be greater than the first and second heights (609, 611). Moreover, as depicted here, the first height (609) may be greater than the second height (611), however, in some instances the second height (611) may be greater than the first height (609).

FIG. 6B depicts a cross-sectional view of the elongate body (600) comprising a first lumen (616), a second lumen (618), a third lumen (620), a fourth lumen (622), a first skive line (624), and a second skive line (626). The first, second, third, and fourth lumens (616, 618, 620, 622) may be analogous to the first, second, third, and fourth lumens (502, 504, 506, 508) of FIG. 5B, described in more detail above. As mentioned above and depicted in FIGS. 6E and 6F, in some instances, the elongate body may comprise a D-shaped cross-sectional shape. In order to fabricate an elongate body with a D-shaped cross-sectional shape, a portion of the elongate body may be cut or otherwise removed. In this embodiment, the first and second skive lines (624, 626) indicate where to cut the elongate body (i.e., at what height) to remove a bottom section of it to create a portion or portions of the elongate body comprising a D-shaped cross-sectional shape. Cutting the elongate body (600) at the first and second skive lines (624, 626) yields an elongate body (600) with the cross-sectional shapes depicted in FIGS. 6F and 6E, respectively. Thus, the first and second skive lines (624, 626) may correspond to the heights for the third and second portions (612, 608) of the elongate body (600), respectively. In removing the bottom section of the elongate body (600), a section of the elongate body forming all or part of the third lumen (620) may be removed. For example, when the elongate body (600) is cut at the first skive line (624), all of the third lumen (620) may be removed (as shown in FIG. 6F), and when the elongate body is cut at the second skive line (626), only a portion of the third lumen (620) may be removed (as shown in FIG. 6E) such that the elongate body (600) comprises a lumen in the form of a groove, as can be seen in FIG. 6C.

In some variations (e.g., when using the device in a minimally invasive procedure), cutting the elongate body along the first and/or second skive lines may allow the device to more easily access the neck of the left atrial appendage for closure. The devices described here may be advanced to the LAA along a guide wire housed in a lumen (e.g., the third lumen (620)) of the elongate body (600). In some embodiments, the devices may be used with a set of guide wires (e.g., a transeptal guide wire and a pericardial guide wire) comprising alignment members (e.g., magnets, interconnecting members, radiopaque or echogenic markers, and the like) on their distal ends that align the guide wires across tissue (e.g., the LAA). A closure device may be advanced pericardially to the LAA along the pericardial guide wire until it reaches the distal tip of the LAA. In order to advance the snare loop assembly or closure loop around the LAA and to its neck for closure, the distal tip of the elongate body, from which the closure loop extends, may need to be advanced past the distal tip of the LAA while the alignment members remain engaged or otherwise aligned. Removing the bottom section of a distal portion of the elongate body (600) and part or all of the lumen housing the guide wire (e.g., the third lumen (620)) may allow the distal end of the elongate body (600) and the closure loop to travel past the distal tip of the guide wire (and the alignment member attached thereto) and the LAA, to the neck of the LAA, while the guide wire remains in the remaining (proximal) portion of the guide wire lumen. After the suture loop is deployed, the elongate body (600) may then be removed from the body of a patient using the same pericardial guide wire that it was advanced along. Thus, the guide wire need not be removed or repositioned during a procedure to allow the distal end of the elongate body, and the closure loop attached thereto, to access the neck of the LAA for closure.

FIG. 6C is a perspective view of a distal end of the elongate body (600) and depicts the first and second transitions (606, 610) and the second and third portions (608, 612) of the elongate body (600). The first and second transitions (606, 610) may comprise an angled, ramped, tapered, and/or beveled bottom surface (628, 630), which may prevent the elongate body (600) from kinking or getting caught on tissue when advancing through the body. As depicted in FIG. 6G, in some embodiments, the third portion (612) may have a tip (603) covering it. The tip (603) may be designed to align with the distal edge of the second transition (610) such that the tip is flush with the distal edge of the second transition (610) (e.g., the height of the third portion (612) may be the same as the height of the distal edge of the second transition (610), and there may be no space or gap between the tip (603) and the distal edge of the second transition (610)). The tip may be made of any suitable material, and in some variations, may be a rigid polymer.

In some instances, it may be desirable to utilize an elongate body comprising additional portions, which may further vary the bending characteristics of the elongate body along its length. For example, in some instances, the orientation, shape, and/or location of a target tissue may make it difficult to access and/or ligate. Accordingly, in some circumstances, it may be desirable for a longer portion of the elongate body of the closure devices described here to be flexible, as this may facilitate access to and ligation of hard to reach tissues. This may be especially useful in variations of the closure devices described here comprising stiffened proximal portions because, while the stiffened proximal portions may assist with the torqueability of the closure devices, they may, in some instances, decrease the flexibility of the elongate body. Therefore, utilizing an elongate body comprising additional portions designed to increase bending flexibility may result in a closure device that is responsive and able to reach and/or ligate target tissues with various shapes, orientations, and locations.

Figure 19A:
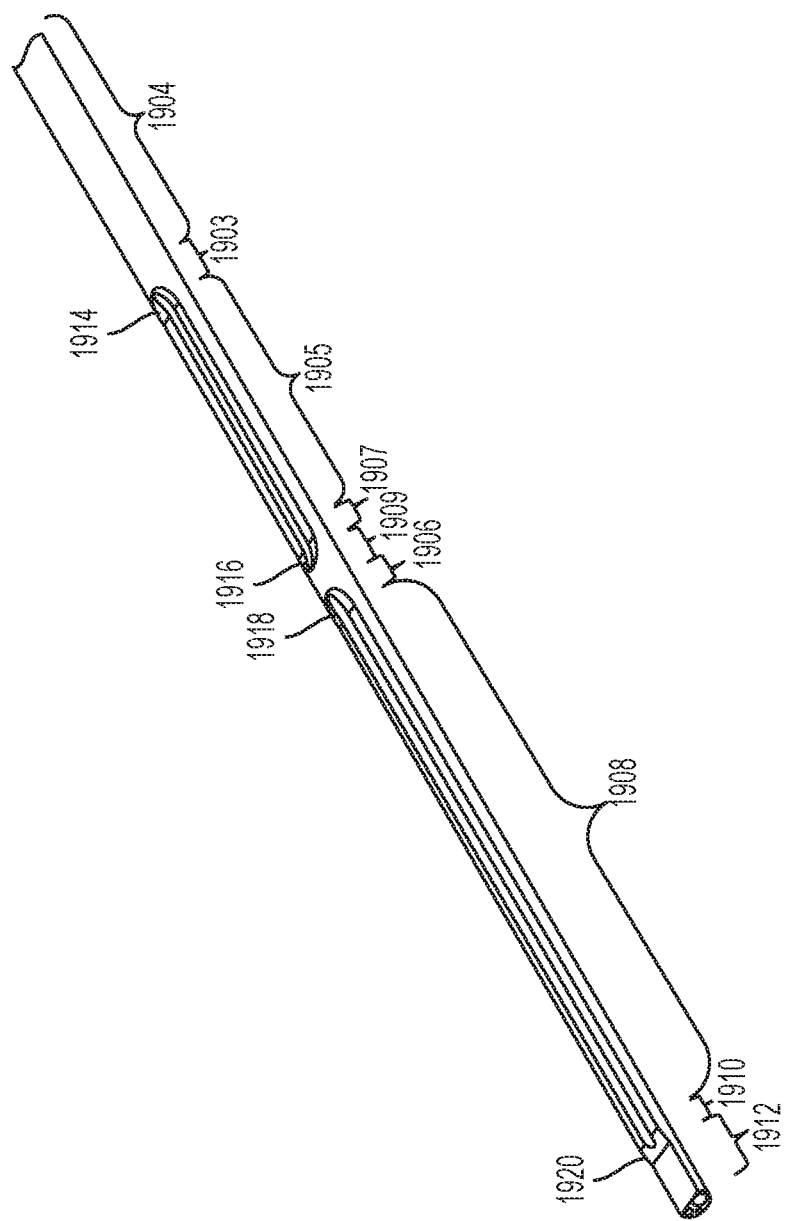
FIGS. 19A, 19B, and 19C depict perspective, side, and bottom views, respectively, of a variation of the elongate body of the closure devices described here.
Figure 19B:
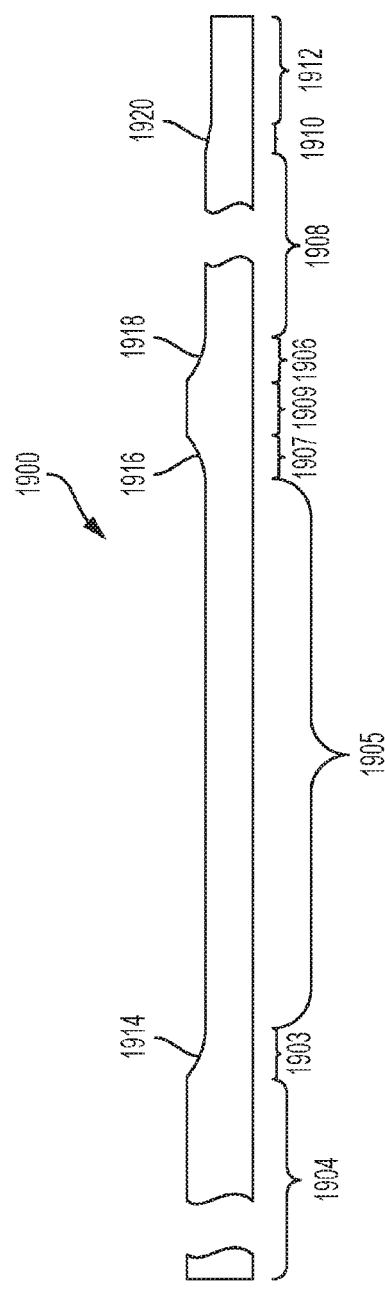
Figure 19C:
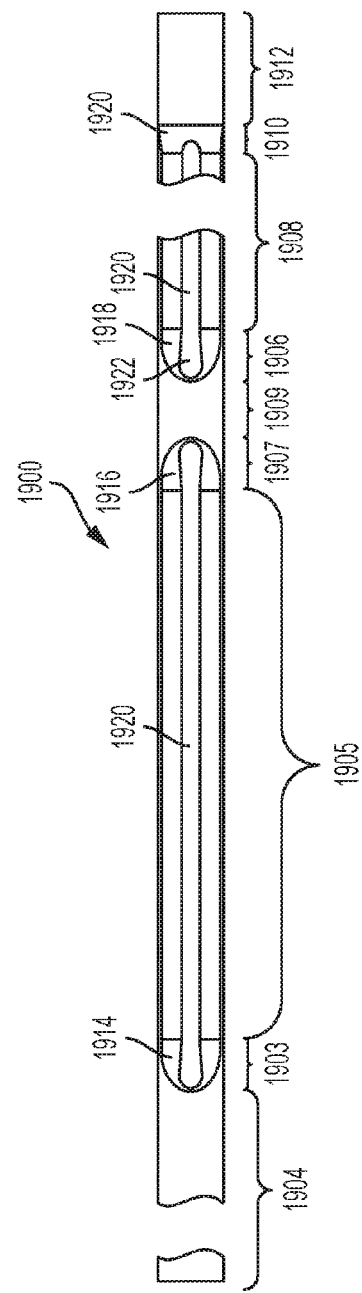

FIGS. 19A-19C depict a variation of the elongate body (600) depicted in FIGS. 6A-6G comprising two additional portions and transitions positioned between a proximal end of the elongate body and the first transition (606), which may increase the flexibility of the middle and/or distal parts of the elongate body. FIG. 19A depicts a perspective view of the elongate body (1900), while FIGS. 19B and 19C depict a side and bottom views, respectively. In this variation, the elongate body (1900) may comprise five portions and four transitions: a first portion (1904), a first transition (1903), a second portion (1905), a second transition (1907), a third portion (1909), a third transition (1906), a fourth portion (1908), a fourth transition (1910), and a fifth portion (1912). In this variation, the first portion (1904) and third portion (1909) may comprise circular cross-sectional shapes, while the second portion (1905), fourth portion (1908), and fifth portion (1912) may comprise D-shaped cross-sectional shapes. For example, the first and third portions (1904, 1909) may have a cross-section similar to or the same as the cross-section of the first portion (604) in the embodiment shown in FIG. 6A, depicted in FIG. 6D. The second and fourth portions (1905, 1908) may have a cross-section similar to or the same as the cross-section of the second portion (608) in the embodiment shown in FIG. 6A, depicted in FIG. 6E. The fifth portion (1912) may have a cross-section similar to or the same as the cross-section of the third portion (612) in the embodiment shown in FIG. 6A, depicted in FIG. 6F. It should be appreciated that the diameters and/or heights (605, 609, 611) may vary between the embodiment shown in FIG. 6A and that shown in FIG. 19A.

In this variation, the first, second, third, and fourth transitions (1903, 1907, 1906, 1910) may be similar to the first and second transitions (606, 610) in the embodiment depicted in FIG. 6A. For example, the first, second, third, and fourth transitions (1903, 1907, 1909, 1910) may also comprise an angled, ramped, tapered, and/or beveled surface (1914, 1916, 1918, 1920). In this variation, the first transition (1903) may be positioned between and connect the first portion (1904) and the second portion (1905), the second transition (1907) may be positioned between and connect the second portion (1905) and the third portion (1909), the third transition (1906) may be positioned between and connect the third portion (1909) and the fourth portion (1908), and the fourth transition (1910) may be positioned between and connect the fourth portion (1908) and the fifth portion (1912). As described above with respect to the embodiment depicted in FIGS. 6A-6G, in some variations, the fifth portion (1912) may have a tip (e.g., tip 603) covering it.

Figure 20:
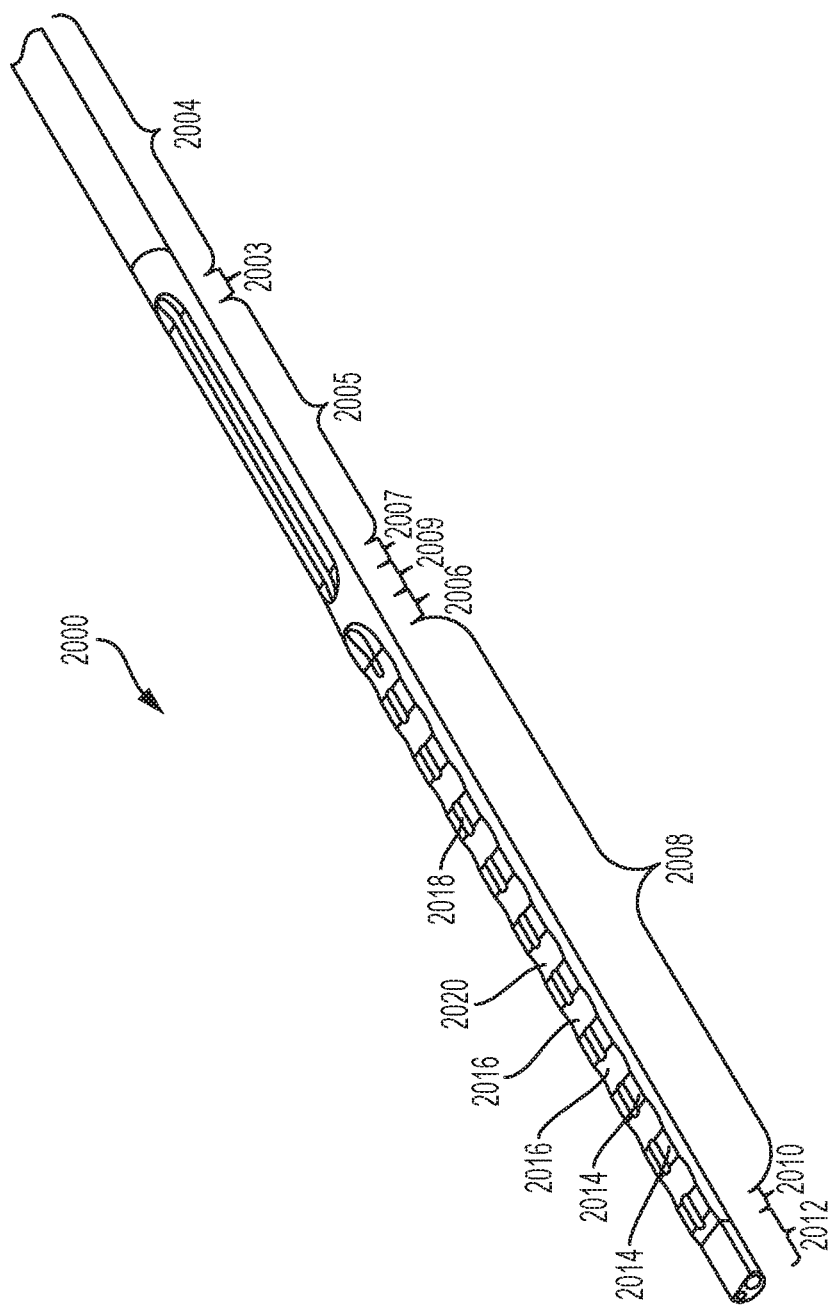
FIG. 20 illustrates a perspective view of a variation of the elongate body of the closure devices described here.

FIG. 20 depicts another variation of the elongate bodies (600, 1900) depicted in FIGS. 6A-6G and 19A-19C. In this variation, the elongate body (2000) may also comprise five portions and four transitions: a first portion (2004), a first transition (2003), a second portion (2005), a second transition (2007), a third portion (2009), a third transition (2006), a fourth portion (2008), a fourth transition (2010), and a fifth portion (2012), but the fourth portion (2008) may be scalloped, which may increase flexibility in a localized region (e.g., the fourth portion (2008)) of the elongate body (2000). For example, the fourth portion (2008) may comprise alternating regions: a first region (2014) with D-shaped cross-section similar to or the same as that depicted in FIG. 6E and a second region (2016) with D-shaped cross-section similar to or the same as that depicted in FIG. 6F. Thus, the first region (2014) may comprise a lumen (2018), while the second region (2016) may not. It should be appreciated that in some variations, the height of the elongate body (2000) in the second region (2016) may be the same as the height of the elongate body (2000) in the fifth portion (2012), while in other variations the height of the elongate body (2000) in the second region (2016) may be greater than or less than the height of the elongate body (2000) in the fifth portion (2012). In some instances, and as depicted in FIG. 20, the second region (2016) may comprise a concave lower surface (2020) instead of a flat lower surface. Additionally, in some variations, the second portion (2005) may also be scalloped and the fourth portion (2008) may or may not be scalloped (i.e., the fourth portion (2008) may have a similar construction as the fourth portion (1908) shown in FIGS. 19A-19C)).

While the first and second regions (2014, 2016) are shown having the same or similar lengths, this need not be the case. In some instances, the first regions (2014) may be longer than the second regions (2016), while in other variations the second regions (2016) may be longer than first regions (2014). In some variations, the lengths of the first and second regions (2014, 2016) may vary between occurrences of the regions. In addition, the elongate body (2000) may comprise any suitable number of first and second regions (e.g., 3, 4, 5, 6, 7, 8, 9, 10, or more), and need not contain the same number of each region.

As described above, the closure devices described here may be advanced to the LAA along a guide wire housed in a lumen (e.g., the third lumen) of the elongate body of the closure device. In some variations and as later described, a guide device may also be used to assist in advancing and retracting the guide wire and the closure device. In these variations, the configuration of the elongate body of the closure device may assist in managing the guide wire during retraction through the guide device and may therefore reduce the likelihood of the guide wire wrapping around the closure device or otherwise interfering with retraction of the closure device.

In use, after suture loop deployment, both the closure device and the guide wire may be retracted through the guide device. However, in some variations, the diameter of the guide device may be too small to accommodate passage of both the closure device and the guide wire side-by-side, especially in variations in which the guide wire comprises an alignment member with a larger diameter than the guide wire, for example, a magnet, at its distal tip. Thus, in order to remove the guide wire and the closure device through the guide device and prevent the guide wire from wrapping around or otherwise interfering with the removal of the closure device, the guide wire may be centered or otherwise positioned along and against an underside of the elongate body while the elongate body is retracted, after which the guide wire may also be retracted.

Accordingly, to assist in positioning the guide wire and closure device for retraction, in some variations, the guide wire (including the alignment element) may be advanced through the snare loop and distal to the tip of the closure device. The guide wire may then be retracted until the alignment element is held against or is flush with the elongate body (e.g., at the first transition). Because the alignment element may have a larger diameter than the lumen through which the guide wire is slideably disposed (e.g., the third lumen), a portion of the elongate body may prevent the guide wire from being fully retracted into the elongate body. For example, the guide wire may be retracted until the alignment element reaches an opening of the lumen, and upon continuous application of force to the proximal end of the guide wire, the alignment element may be held within or adjacent to the opening. This may center the alignment element next to and along the underside of the elongate body. The closure device may then be retracted into the guide device with the alignment element held centered against the underside of the elongate body until the alignment element is disposed within the snare loop, at which point the loop and then the alignment element may be retracted into the guide device.

In variations of the elongate bodies described here comprising additional portions that may increase the bending flexibility of the middle and/or distal sections of the elongate body, it may be desirable to maintain a portion of the elongate body for use in centering the guide wire so that the retraction method described above may be utilized. For example, referring to the elongate body shown in FIGS. 19A-19C, the fourth and second portions (1908, 1905) may comprise a third lumen (1920) in the form of a groove, while the third portion (1909) may comprise a full third lumen (1920). Thus, when the elongate body (1900) is used with a guide wire comprising an alignment element coupled to its distal end, the guide wire may be retracted until the alignment element reaches the distal opening (1922) of the third lumen (1920), at which point the diameter of the alignment element may prevent further retraction of the guide wire. Thus the bottom surface of the third transition (1906) and the third portion (1909) may act as an alignment tool during retraction of the guide wire and closure device. Accordingly, although removing the third portion (1909) and second and third transitions (1907, 1906) may result in a more flexible elongate body, and thus may be desirable in some instances, doing so may make it more difficult to retract the elongate body and closure device. Thus, in some variations, it may be desirable to include the third portion (1909) and second and third transitions (1907, 1906) at least because they may assist in guide wire management during retraction.

Referring back to FIG. 6A, the collar (602) may connect the elongate body (600) to the handle (not shown). The collar (602) may be integrally formed with the elongate body (600), or it may be a separate component and may be attached to the elongate body (600) as depicted in FIG. 6A. As shown in FIG. 6A, the collar (602) may comprise a lumen therethrough through which the proximal end of the elongate body (600) may be inserted. The collar (602) may be attached to the elongate body (600) and the handle using any suitable means (e.g., adhesive, bonding, and the like). In some embodiments, the collar (602) may be integrally formed with the handle. In some variations, the collar (602) may prevent the elongate body (600) from rotating with respect to the handle, while in other variations, the collar (602) may be attached to a toggle that enables a user to rotate the collar such that the entire elongate body may rotate with respect to the handle, as described in more detail in the U.S. Provisional Patent Application titled "Tissue Ligation Devices and Methods Therefor", and filed on Mar. 24, 2015.

In some variations, the elongate body (600) may also comprise markers (614) that may provide an indication of the location of the device in the body or in relation to another device or element (e.g., a guide device). These markers (614) may be especially useful when using a minimally invasive approach. The markers may comprise any suitable imaging element, for example, a visual, radiopaque, or echogenic marker, and may be attached to the elongate body in any suitable manner (e.g., printed on, adhesive, rings, and the like). The elongate body (600) may comprise any suitable number of markers (614), for example, one, two, three, four, or five, and the markers may be located at any suitable location along the length of the elongate body (600).

In some embodiments, the markers (614) may be placed at specific locations along the elongate body (600) to provide information to a user about the interaction of the elongate body with a guide device. For example, the markers (614) may be placed such that a marker may become apparent when the distal tip or a particular portion (e.g., the first portion, the second portion, the third portion, a transition, and the like) of the elongate body enters or exits a guide device. In some embodiments, the markers may be placed equidistant along the elongate body instead, which may provide a clear indication of how much of the elongate body is within a patient's body. In some variations, the placement of the markers (614) along the elongate body may allow a user to decrease the amount of time an imaging mechanism (e.g., radiation) is needed because the user may better understand the location of the device in a patient's body without imaging throughout an entire procedure.

Stiffened Portion

In some embodiments, the elongate body may comprise one or more stiffened portions that may prevent sections of the elongate body from bending or twisting undesirably during a procedure. In use, the elongate body may be forced into fairly significant curvatures due to patient anatomy, and it may be useful for the device to maintain the original orientation of the snare and suture loop during deployment. Additionally, a user may want to rotate the elongate body using the handle of the device (which may be outside a patient's body), and it may be desirable for the rotation of the handle to cause the distal tip of the elongate body to rotate the same or a similar amount as the handle (i.e., for there to be one-to-one rotation between the handle and the distal tip of the elongate body). This may provide a user with better control over the device and may make the device easier to maneuver. However, because the device may be advanced through a patient's body, it may also be desirable for the device to maintain some flexibility to prevent tissue damage and to allow the device to reach the LAA when the path is fairly tortuous. Thus, it may be desirable for the elongate body to be configured to resist twisting, while still being able to bend.

In some embodiments, the stiffened portion of the elongate body may be formed such that it is stiffer than the other portions of the elongate body. In some instances, the stiffened portion of the elongate body may comprise a braided catheter, and the flexible portion or portions may comprise a catheter made of the same or a similar material as the core of the braided catheter (i.e., the core material without the braided material). For example, the braided catheter may comprise a polyether block amide core with a stainless steel braid, and the flexible portion(s) may comprise polyether block amide (or a material with similar flexibility) without the stainless steel braid. In some variations, the stiffened portion may comprise a different material than the flexible portion. For example, the stiffened portion may comprise a nylon, and/or a hard polymer, and the flexible portion may comprise a soft polymer. In some variations, the stiffened and flexible portions may comprise materials with variable durometers such that the material of the stiffened portion has a higher durometer than the material of the flexible portion. In some embodiments, the thickness of the elongate body may vary such that the stiffened portion has a greater thickness than the flexible portion.

In some embodiments, the stiffened portion of the elongate body may comprise a catheter and one or more stiffening elements. As their name suggests, the stiffening elements may be designed to increase the stiffness of the elongate body relative to other sections of the elongate body that do not have stiffening elements. The portions of the elongate body that may be more flexible than the stiffened portion of the elongate body may be referred to as flexible portions, however, it should be appreciated that the entire elongate body may be flexible. The elongate body may comprise any suitable stiffening element(s). For example, in some embodiments, the stiffening element may comprise a braided sheath that may be adhered, or otherwise attached, to the catheter. For example, the construction of the braided sheath may be similar to that of the braid in the braided catheter, but the sheath may be fabricated separately from the catheter body and may be bonded to an external surface of the catheter body. In some variations, the stiffening element may be embedded within a wall of the elongate body. For example, the stiffening element may comprise a wire or other stiff material in a wall of the catheter. In other embodiments, the stiffening element may be housed within, or otherwise coupled to, a lumen of the elongate body. For example, in some variations, the stiffening element may comprise a wire or a hypotube (e.g., a stainless steel tube) coupled to a lumen of the elongate body. In other variations, the stiffening element may comprise a polymer tube that is more resistant to bending than the catheter, and the polymer tube may be disposed within, or coupled to, a lumen of the elongate body. The stiffening element may be coupled to the lumen of the catheter in any suitable manner, including, but not limited to, bonding, adhesive, shrink-fit, reflowing, coating, and the like.

Figure 7:
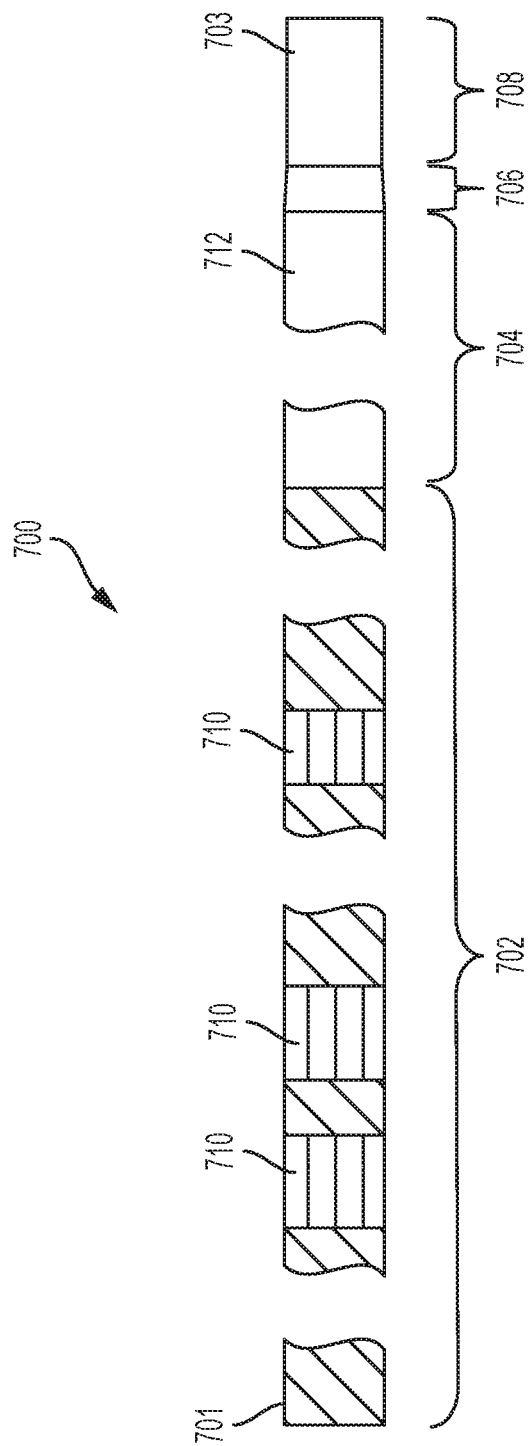
FIG. 7 illustrates an embodiment of an elongate body with stiffened and flexible portions.

FIG. 7 depicts an elongate body (700) having a proximal end (701) and a distal end (703), and comprising a stiffened proximal portion (702), a flexible middle portion (704), a transition (706), a flexible distal portion (708), and markers (710). The stiffened proximal portion (702) may be located at the proximal-most end of the elongate body and may be coupled to a collar, which may in turn be coupled to a handle (as described above with respect to FIG. 6A). The flexible middle portion (704) may be located between the proximal stiffened portion (702) and the transition (706), and the transition (706) may be located between the flexible middle portion (704) and the flexible distal portion (708). The markers (710) may assist a user with visualization of the device during a procedure, as is described above with respect to the markers (614) in FIG. 6A. While FIG. 7 includes one stiffened portion, two flexible portions, and one transition, the elongate body (700) may comprise any suitable number of stiffened portions (e.g., one, two, three, or four), transitions (e.g., one, two, three, four, five, or more), and flexible portions (e.g., one, two, three, four, five, six, or more). For example, as will be described in more detail below, in some variations, the elongate body (700) may comprise two flexible middle portions and two transitions. In other variations, the elongate body (700) may comprise four flexible middle portions and four transitions. Additionally, in some variations, the elongate body (700) may comprise a stiffened portion between flexible portions, or vice versa.

As mentioned above, in some variations, the closure device may further comprise a tip (e.g., tip (603) shown in FIG. 6G) coupled to, disposed over, and/or fixedly attached to (e.g., using adhesive or the like) the flexible distal portion of the elongate body. As also described above, in some variations, the tip may be hard or rigid and may therefore prevent the flexible distal portion from bending. In these variations, the flexible distal portion may no longer be flexible. In other variations comprising a tip, the tip may also be flexible such that the flexible distal portion remains flexible.

In some variations, the elongate body (700) may further comprise a jacket (712) over the entire external surface of the elongate body or just a portion of it. The jacket may be used to smooth the external surface of the elongate body and/or to increase the thickness of the elongate body, which may in turn modify its bending and/or torsional resistance. In some embodiments, the elongate body may comprise a jacket (712) over the stiffened proximal portion (702) and the flexible middle portion (704), but the jacket (712) may not extend over the transition (706) and the flexible distal portion (708). In some variations, the jacket (712) may extend over the stiffened proximal portion (702), the flexible middle portion (704), and the transition (706), but may not include the flexible distal portion (708). In still other embodiments, the jacket (712) may extend the entire length of the elongate body (700). The jacket (712) may be coupled to an external surface of the elongate body (700) by lamination, adhesion, bonding, or any other suitable technique, and may comprise any suitable polymer (e.g., polyether block amide).

As mentioned above, in some embodiments, the stiffened proximal portion (702) may comprise a braided catheter. The braid of the braided catheter may be formed from any suitable wire (i.e., 0.002 inch (0.0508 mm) thickness circular wire, 0.001 inch×0.007 inch (0.0254 mm×0.1778 mm) rectangular wire, a combination of the two, circular or rectangular wire with different dimensions, and the like). The wire may be any suitable material, for example, stainless steel, and may be annealed if desired. The braided catheter may be formed using a reflow process such that the braid becomes integral with the catheter and is embedded in the wall of the catheter, as opposed to attached to an external surface of the catheter using, for example, adhesive (which is also contemplated and is described in more detail below). Using an elongate body with the braid embedded within a wall of the catheter (braided catheter) may affect the responsiveness of the elongate body to torque applied to the handle of the device. For example, the integration of the braid into the catheter's core material may modify the distribution of force within and along the elongate body. In some instances, the material closest to the external surface of the elongate body may have a larger impact on the torsional response of the elongate body. In these instances, varying the location of the braid within the wall of the catheter may affect its torsional response, which may in turn impact a user's ability to steer and control the distal tip of the elongate body.

In some instances, the cross-sectional shape and diameter and/or height of the elongate body may vary throughout the elongate body, as described in detail above, and the elongate body may also comprise a stiffened proximal portion (702), a flexible middle portion (704), and a flexible distal portion (708). In some instances, the stiffened and flexible portions of the elongate body may correspond to (i.e., have the same location, length, cross-sectional shape, and/or lumen configuration) the first, second, and third portions (604, 608, 612) of the elongate body (600) illustrated in FIG. 6A, whereas in other variations, the first, second, and third portions (604, 608, 612) may overlap or otherwise include more than one of the stiffened proximal, flexible middle, and flexible distal portions. For example, in the embodiment depicted in FIG. 7, the stiffened proximal portion (702) may be located within the first portion (604), the flexible middle portion (704) may be located in both the first portion (604) and the second portion (608), and the flexible distal portion may be located in the third portion (612). As mentioned above, in some instances, a rigid tip may be coupled to the flexible distal portion, which may result in a rigid distal portion.

The stiffened and flexible portions may have any suitable cross-sectional shape (e.g., circular, oval, D-shaped, and the like) and diameter or height. In some embodiments, the elongate body (700) may have a circular cross-sectional shape along its entire length. In other embodiments, the stiffened proximal portion (702) may have a circular cross-sectional shape with a first diameter, the flexible middle portion (704) may have a circular cross-sectional shape with a second diameter, and the flexible distal portion (708) may have a D-shaped cross-sectional shape with a height. In these embodiments, the first diameter may be greater than the second diameter, which may be greater than the height.

For example, the stiffened proximal portion (702) may have a diameter between about 0.160 inches (4.064 mm) and about 0.169 inches (4.293 mm). In some variations, the stiffened proximal portion (702) may have a diameter of about 0.163 inches (4.140 mm). The flexible middle portion (704) may have a diameter between about 0.156 inches (3.962 mm) and about 0.162 inches (4.115 mm). In some embodiments, the flexible middle portion (704) may have a diameter of about 0.160 inches (4.064 mm). The flexible distal portion (708) may have diameter of about 0.144 inches (3.658 mm) to about 0.150 inches (3.81 mm). In some embodiments, the flexible distal portion (708) may have a diameter of about 0.148 inches (3.760 mm). In some variations, the flexible distal portion (708) may have a height of about 0.094 inches (2.388 mm) to about 0.098 inches (2.489 mm). In some embodiments, the flexible distal portion (708) may have a height of about 0.096 inches (2.438 mm). In some embodiments, the diameter of the stiffened proximal portion may be less than or equal to about 1.00, 1.02, 1.04, 1.06, 1.08, or 1.10 times the diameter of the flexible middle portion.

In some variations, the elongate body (700) may comprise multiple flexible middle portions and multiple transitions. For example, in one embodiment, the elongate body (700) may comprise a stiffened proximal portion (702), first and second flexible middle portions, first and second transitions, and a flexible distal portion (708). The first flexible middle portion may be just distal of the stiffened proximal portion (702) and just proximal of the first transition, and the second flexible middle portion may be between the first transition and the second transition (e.g., transition (706)). With reference to FIG. 6A, in these embodiments, the stiffened proximal portion (702) and the first flexible middle portion may be located in the first portion (604), the second flexible middle portion may correspond to the second portion (608), and the flexible distal portion (708) may correspond to the third portion (612). The first and second transitions may correspond to the first and second transitions (606, 610).

In this variation, the stiffened proximal portion (702) may have a circular cross-sectional shape with a first diameter, the first flexible middle portion may have a circular cross-sectional shape with a second diameter, the second flexible middle portion may have a D-shaped cross-sectional shape with a first height, and the flexible distal portion (706) may have a D-shaped cross-sectional shape with a second height. In these variations, the first diameter may be greater than the second diameter, which may be greater than the first height, which may be greater than the second height; however, this need not be the case.

For example, the stiffened proximal portion and flexible distal portion may have the diameters/heights described above and the first flexible middle portion may have a diameter of about 0.156 inches (3.962 mm) to about 0.162 inches (4.115 mm), and the second flexible middle portion may have a height of about 0.116 inches (2.946 mm) to about 0.122 inches (3.099 mm). In some variations, the first flexible middle portion may have a minimum diameter of about 0.158 inches (4.013 mm), and the second flexible middle portion may have a height of about 0.120 inches (3.048 mm).

In another variation, the elongate body (700) may comprise a stiffened proximal portion (702), a first flexible middle portion, a first transition, a second flexible middle portion, a second transition, a third flexible middle portion, a third transition, a fourth flexible middle portion, a fourth transition (706), and a flexible distal portion (708). In this embodiment, the flexible middle portion (704) may include the first, second, third and fourth flexible middle portions and the first, second, and third transitions (not shown). The stiffened and flexible portions and the transitions may be located within or correspond to the portions and transitions of the elongate body (1900) depicted in FIGS. 19A-19C. For example, the stiffened proximal portion (702) and first flexible middle portion may be located within the first portion (1904). The second, third, and fourth flexible middle portions may correspond to the second, third, and fourth portions (1905, 1909, 1908) respectively, and the flexible distal portion (708) may correspond to the fifth portion (1912). Additionally, the first, second, third, and fourth transitions may correspond to the first, second, third, and fourth transition (1903, 1907, 1906, 1910), respectively.

In this variation, the stiffened proximal portion (702) may have a circular cross-sectional shape with a first diameter, the first flexible middle portion may have a circular cross-sectional shape with a second diameter, the second flexible middle portion may have a D-shaped cross-sectional shape with a first height, the third flexible middle portion may have a circular cross-sectional shape with a third diameter, the fourth flexible middle portion may have a D-shaped cross-sectional shape with a second height, and the flexible distal portion (706) may have a D-shaped cross-sectional shape with a third height. In these variations, the first diameter may be greater than the second diameter, which may be the same as the third diameter. The second and third diameters may be greater than the first height, which may be the same as the second height. The first and second heights may be greater than the third height; however, this need not be the case.

For example, the stiffened proximal portion and flexible distal portion may have the diameters/heights described above, the first and third flexible middle portions may have a diameter of about 0.145 inches (3.683 mm) to about 0.151 inches (3.835 mm) and the second and fourth flexible middle portions may have a height of about 0.096 inches (2.438 mm) to about 0.120 inches (3.048 mm). In some variations, the first and third flexible middle portions may have a diameter of about 0.148 inches (3.759 mm) and the second and fourth flexible middle portions may have a height of about 0.108 inches (2.743 mm). While the first and third flexible middle portions and second and fourth flexible middle portions are described above has having the same diameters and heights respectively, this need not be the case. In some variations, the diameter of the first flexible middle portion may be greater than the diameter of the third flexible middle portion, or vice versa. Additionally, in some instances, the height of the second flexible middle portion may be greater than the height of the fourth flexible middle portion, and vice versa.

As mentioned above with respect to FIGS. 19A-19C, it may be desirable to utilize an elongate body comprising additional flexible middle portions, especially in combination with a stiffened proximal portion, to increase the bending flexibility of the middle and/or distal parts of the elongate body. This increased bending flexibility may assist in access to and ligation of hard to reach tissue. Additionally, as also described above, using a catheter with a curved distal segment may also assist in accessing and ligating tissue, and the cross-sectional shape, cross-sectional diameter/height, number of flexible portions and/or number and type of proximal stiffening elements may determine what angle (1812) and radius (1810) may be most desirable for a particular procedure. For example, in this variation and/or the variation described above with respect to FIG. 7 comprising multiple flexible middle portions, and when the target tissue is the LAA, it may be desirable to use an elongate body with a curved distal segment having an angle of about 86 to about 88 degrees and a radius of about 3.10 inches (7.87 cm) to about 3.40 inches (8.64 cm). In some instances, it may be desirable to use an elongate body with a curved distal segment having an angle of about 87 degrees and a radius of about 3.30 inches (8.38 cm).

The foregoing diameters and heights are exemplary and the stiffened proximal portion (702), flexible middle portion (704) or portions, and flexible distal portion (708) may have any suitable diameters or heights.

It should be appreciated that the diameters and/or heights of the stiffened portion(s) and flexible portion(s) of the elongate body may affect the torqueability of the elongate body and its responsiveness. In some instances, the stiffened proximal portion may transmit the torque applied to the handle of the elongate body directly to the flexible portion, but the flexible portion may not transmit all of the torque at its proximal end to its distal end. Put another way, in some instances, the elongate body will twist at a point or in regions along its length when the handle is rotated, which may prevent the distal end of the elongate body from rotating the same or a similar amount as the handle. In these instances, the elongate body has a low torsional response. Modifying the diameters and/or heights, lengths, and/or stiffness of the various portions of the elongate body may vary the amount of angular twist between the handle and the distal end of the elongate body and may increase the torsional response of the elongate body. In particular, varying the diameter of the flexible portion of the elongate body may have a greater effect on torsional response than varying the diameter of the stiffened portion. Because it may be desirable for the rotation of the elongate body to mirror the rotation of the handle to the extent possible, meaning that the rotation angle (i.e., 5 degrees, 10 degrees, 15 degrees, 30 degrees, etc.) of the distal tip of the elongate body matches the rotation angle of the handle (i.e., how much a user rotates the handle), it may be desirable to vary the diameter and/or height of the flexible portion with respect to the stiffened portion. For example, in some embodiments, the elongate body may be configured such that rotating the handle 180 degrees causes the distal tip of the elongate body (700) to rotate at least 120 degrees, 140 degrees, 160 degrees, 175 degrees, and/or 180 degrees. In embodiments in which rotating the handle 180 degrees causes the distal tip of the elongate body (700) to rotate 180 degrees, the device has 1:1 rotation.

As mentioned above, the elongate body may comprise one or more transitions connecting the portions of the elongate body comprising different diameters and/or different cross-sectional shapes. The transitions may provide smooth conversions between the different portions of the elongate body, which may aid in maneuverability. For example, using transitions may remove abrupt diameter changes that may cause the elongate body to kink. In some variations, an abrupt change in diameter between different portions of the elongate body may act as a stress-concentrator, which may make it more likely for the elongate body to kink or buckle at the transition when the elongate body is subjected to external forces. In these variations, it may be desirable to have transitions of sufficient lengths to decrease the stress concentration at these points or regions and thus decrease the likelihood that the elongate body will kink or buckle.

Figure 8B:
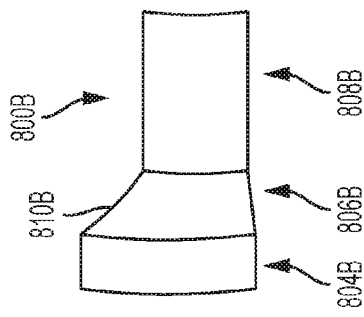
FIGS. 8A-8C depict variations of a transition of an elongate body.
Figure 8C:
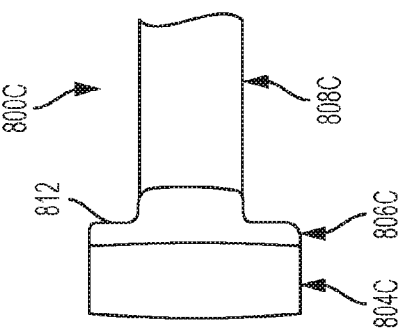
Figure 8A:
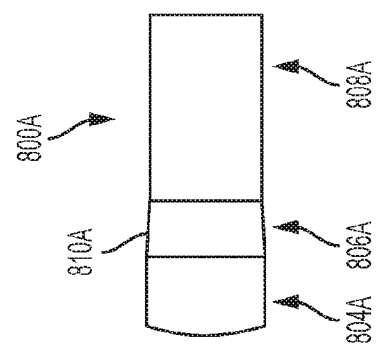

Turning to FIGS. 8A-8C, shown there are perspective views of variations of a transition (806A, 806B, 806C) positioned between a middle flexible portion (804A, 804B, 804C) and a flexible distal portion (808A, 808B, 808C) of an elongate body (800A, 800B, 800C). The transition (806A, 806B, 806C) may have a diameter and/or height that matches the diameter and/or height of the flexible middle portion (804A, 804B, 804C) at the transition's (806A, 806B, 806D) proximal end, and a diameter and/or height that matches the diameter and/or height of the flexible distal portion (808A, 808B, 808C) at its distal end. For example, in embodiments in which the flexible middle portion (804A, 804B, 804C) has a diameter of about 0.160 inches (4.064 mm) and the flexible distal portion (808A, 808B, 808C) has a diameter of about 0.148 inches (3.759 mm), the transition (806A, 806B, 806C) may have a diameter of about 0.160 inches (4.064 mm) at its proximal end and a diameter of about 0.148 inches (3.759 mm) at its distal end. In embodiments comprising a first flexible middle portion and a second flexible middle portion, a transition may be positioned between the second flexible middle portion and the flexible distal portion such that the proximal end of the transition has a diameter and/or height equal to the diameter and/or height of the second flexible middle portion, and the distal end of the transition has a diameter and/or height equal to the diameter and/or height of the flexible distal portion. In embodiments comprising multiple flexible middle portions, transitions may be positioned between the flexible middle portions having diameters and/or heights that match the diameters and/or heights of the portions the transitions connect, as described above. In some embodiments, the diameter and/or height of the transition may decrease symmetrically, as depicted in FIGS. 8A and 8C, while in other embodiments, the diameter and/or height of the transition may decrease asymmetrically, as depicted in FIG. 8B. Moreover, in some variations, the transition may comprise one or more angled surfaces (810A, 810B) such that the transition is tapered and its diameter gradually changes, as shown in FIGS. 8A and 8B. In other variations, the transition may comprise a vertical or substantially vertical surface (812) such that a shoulder or ledge is formed and its diameter abruptly changes, as shown in FIG. 8C. In yet other variations, the transition may comprise a combination of angled and vertical surfaces.

The stiffened proximal portion (702), flexible middle portion (704), transition (706), and flexible distal portion (708) may also have any suitable lengths. For example, the stiffened proximal portion (702) may have a length of about 12.00 inches (30.48 cm) to about 14.00 inches (35.56 cm). In some variations, the stiffened proximal portion (702) may have a length of about 13.00 inches (33.02 cm). The flexible middle portion (704) may have a length of about 3.50 inches (8.89 cm) to about 5.00 inches (12.70 cm). In some variations, the flexible middle portion (704) may have a length of about 4.20 inches (10.67 cm). The flexible distal portion (708) may have a length of about 0.20 inches (5.08 mm) to about 0.40 inches (10.16 mm). In some variations, the flexible distal portion (708) may have a length of about 0.25 inches (6.35 mm). In some embodiments, the length of the stiffened proximal portion (702) may be at least about 2.25, 2.50, 2.75, 3.00, 3.25, or 3.50 times greater than the length of the flexible middle portion.

In embodiments comprising a first flexible middle portion and a second flexible middle portion, the first flexible middle portion may have a length of about 1.50 inches (3.81 cm) to about 2.50 inches (6.35 cm), and the second flexible middle portion may have a length of about 2.00 inches (5.08 cm) to about 3.00 inches (7.62 cm). In some variations, the first flexible middle portion may have a length of about 1.90 inches (4.83 cm), and the second flexible middle portion may have a length of about 2.30 inches (5.84 cm). In some embodiments, the transition may have a length of about 0.070 inches (1.78 mm) to about 0.085 inches (2.16 mm). In some variations, the transition may have a length of at least 0.075 inches (1.91 mm).

In embodiments comprising first, second, third and fourth flexible middle portions, the first flexible middle portion may have a length of about 0.175 inches (4.45 mm) to about 0.220 inches (5.59 mm), the second flexible middle portion may have a length of about 1.20 inches (3.05 cm) to about 1.26 inches (3.20 cm), the third flexible middle portion may have a length of about 0.08 inches (0.20 cm) to about 0.16 inches (0.41 cm), and the fourth flexible middle portion may have a length of about 2.25 inches (5.72 cm) to about 3.25 inches (8.23 cm). In some variations, the first flexible middle portion may have a length of about 0.198 inches (5.03 mm), the second flexible middle portion may have a length of about 1.23 inches (3.12 cm), the third flexible middle portion may have a length of about 0.12 inches (0.30 cm), and the fourth flexible middle portion may have a length of about 2.75 inches (6.99 cm). In some embodiments, the first, second, and third transitions may have a length of about 0.067 inches (1.70 mm) to about 0.167 inches (4.24 mm), or more particularly, from about 0.097 inches (2.46 mm) to about 0.137 inches (3.48 mm), and the fourth transition may have a length of about 0.060 inches (1.52 mm) to about 0.080 inches (2.03 mm). In some variations, the first, second, and third transitions may have a length of about 0.117 inches (2.97 mm) and the fourth transition may have a length of about 0.067 inches (1.70 mm). Although the first, second, and third transitions may have the same length, they need not.

It should be appreciated that the elongate body (700) described in FIG. 7 may comprise any suitable number and configuration of lumens. For example, the elongate body may comprise one or more lumens in any of the configurations described with respect to FIGS. 5A, 5B, and 6B.

Figure 9:
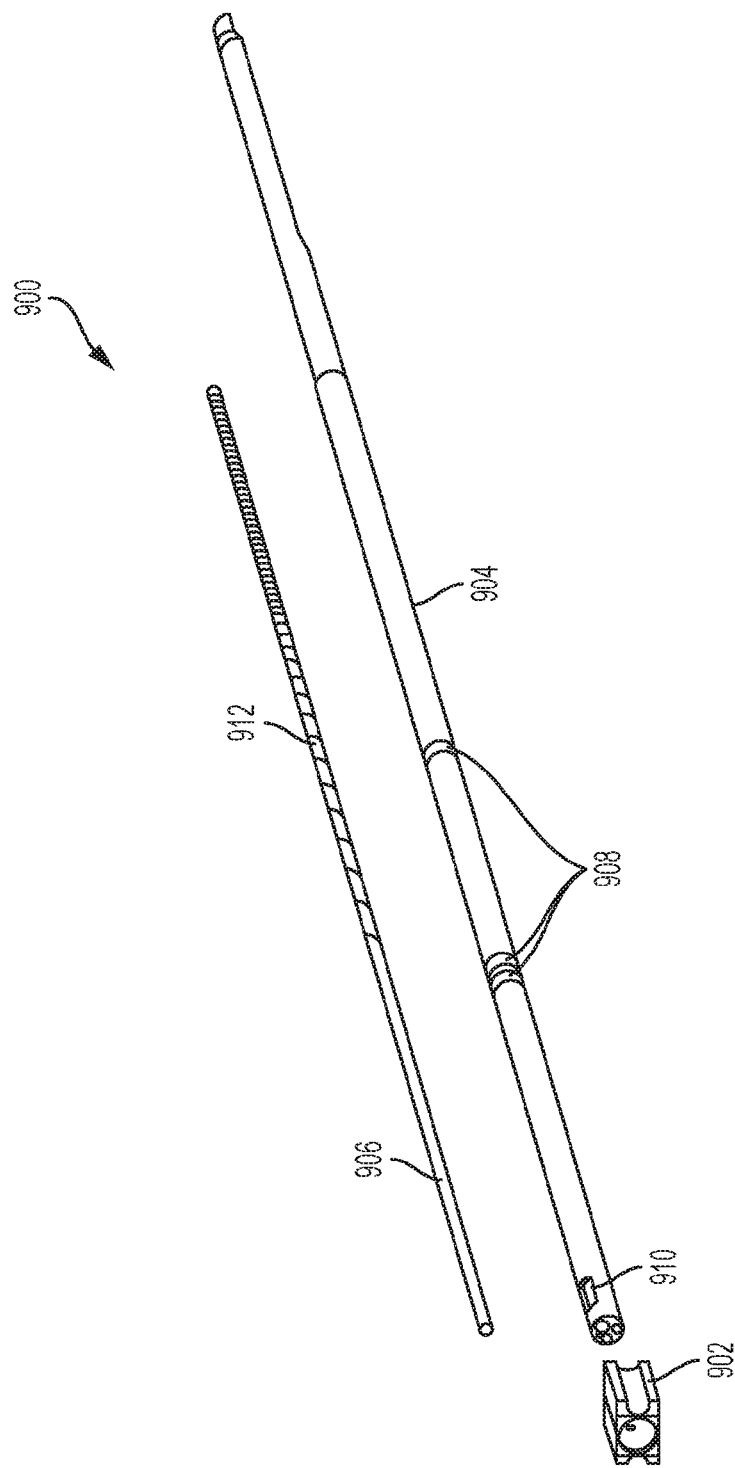
FIG. 9 is an exploded view of an embodiment of an elongate body.

In some variations, the elongate body may comprise more than one mechanism or element that may increase its stiffness. For example, the elongate body may comprise a stiffened proximal portion as described above and may additionally further comprise a second stiffening mechanism. FIG. 9 depicts an example of an embodiment comprising a stiffened proximal portion and a second stiffening element. FIG. 9 shows an exploded view of an elongate body (900) comprising a collar (902) at its proximal end, a catheter (904), a second stiffening element (906), and markers (908). The elongate body (900) may comprise a stiffened proximal portion, for example, a braided catheter, and any number of flexible portions and transitions. The elongate body (900) is depicted comprising four lumens, but may comprise any suitable number of lumens, as described above in detail. In this embodiment, the second stiffening element (906) may be fixedly disposed within a lumen of the elongate body (900) and may be any element configured to increase the rigidity of the catheter (904) compared to portions of the catheter without the second stiffening element (906). For example, the second stiffening element (906) may comprise a polymer tube that is more resistant to bending than the catheter (904) (stiffened or flexible portions), a hypotube (e.g., a stainless steel tube), or any other element configured to increase the stiffness of the catheter (904). The elongate body (900) may optionally comprise an opening (e.g., a slot, groove, or hole) (910) at its proximal end, which may be used to contain an adhesive and/or epoxy to couple the second stiffening element (906) to the catheter (904).

In some variations, the second stiffening element (906) may comprise a pattern (912). The pattern (912) may comprise a series of lines or shapes cut in the second stiffening element (906) that may make the second stiffening element (906) more flexible. It may be desirable to use a stiffening element comprising a pattern because doing so may allow more control over the increase in the stiffness of the elongate body due to presence of the second stiffening element (906). Referring now to FIGS. 10A and 10B, shown there are variations of a second stiffening element (1000A, 1000B) comprising a pattern (1002A, 1002B) cut in it. While depicted as a spiral cut pattern, any suitable cut pattern may be employed (e.g., longitudinal or concentric grooves, slits, aperture patterns, and the like.). The pattern may be cut using any suitable means, for example, a sharpened tool, an electric source (e.g., a laser), a thermal source, and the like. In some instances, the cut pattern may begin at the proximal end of the second stiffening element (1000A, 1000B) and may continue its entire length, whereas in other variations, the cut pattern may begin at a location distal to the proximal end of the second stiffening element (1000A, 1000B) and may travel any desired distance toward its distal end. Additionally, the cut pattern may optionally be discontinuous and include breaks (1006) in the cut pattern (i.e., portions of the pattern that would otherwise be cut but are instead uncut), as depicted in FIG. 10B.

The pattern (1002A, 1002B) may vary along the length of the second stiffening element (1000A, 1000B), for example, as depicted in FIG. 10A. In some embodiments, the angle ($\theta_A, \theta_B$) and/or the pitch (1004A, 1004B) of the cut pattern may vary. In some variations, the angle ($\theta_A, \theta_B$) may decrease and the pitch (1004A, 1004B) may increase from the distal to the proximal end of the second stiffening element (1000A, 1000B). This may provide an increased resistance to bending or twisting at the proximal end, compared to the distal end, of the second stiffening element (1000A, 1000B). It may be useful to have a stiffer proximal end of the elongate body as discussed above, while maintaining the flexibility of at least part of the middle and distal portions of the elongate body to decrease the risk of puncturing or otherwise damaging tissue, and to maintain the elongate body's ability to travel through a curved guide device and/or tortuous anatomy. In other variations, only one of the angle ($\theta_A, \theta_B$) and the pitch (1004A, 1004B) may vary along the length of the second stiffening element (1000A, 1000B). In yet other variations, the angle ($\theta_A, \theta_B$) and the pitch (1004A, 1004B) may remain constant.

The second stiffening element (906) may be any suitable length. In some embodiments, the second stiffening element (906) may be the same or a similar length as the stiffened proximal portion, whereas in other embodiments, the second stiffening element may be shorter than or longer than the stiffened proximal portion. As used herein, "similar lengths" refers to lengths that are within ±10% of each other. In some variations, the second stiffening element (906) may have a length equal to the length of the entire elongate body.

Malleable Shaft

In some instances, it may be desirable to modify the shape and/or curvature of the elongate body to assist in accessing difficult-to-reach anatomy during a procedure. For example, when the devices described here are used during a surgical procedure, it may be desirable to modify the curvature of the elongate body prior to advancing the device into the body, and it may be useful for the elongate body to maintain that pre-set curvature throughout the procedure, or at least until reaching the tissue to be ligated. Specifically, it may be desirable to curve the elongate body to better access the left atrial appendage with the closure element based on positioning at the operating table and a patient's particular unique anatomy.

To enable modification of the shape and/or curvature of the elongate body prior to using the device and allow the device to retain that shape and/or curvature during a procedure, in some embodiments, the elongate body may comprise a malleable member. The malleable member may make the elongate body shapeable. In these embodiments, when a force is applied to the elongate body to curve, bend, or otherwise place it in a particular shaped configuration, the malleable member may maintain that curvature, bend, or shape after the force has been removed or released, thus causing the elongate body to also maintain that curvature, bend, or shape.

The malleable member may be attached to the elongate body in any suitable fashion, including being disposed around the external surface of the elongate body, being disposed in or coupled to a lumen of the elongate body, and/or being embedded in a wall of the elongate body. It should be appreciated that the device may comprise any number of lumens and the lumens may have any suitable configuration, for example, any of the configurations described above with respect to FIGS. 5A, 5B and 6B. In embodiments comprising more than one lumen, the malleable member may be placed in any suitable lumen, for example, the first lumen, the second lumen, the third lumen, or the fourth lumen. In some instances, the malleable member may comprise a proximal end and a distal end, and the proximal end of the malleable member may be fixedly attached to a proximal end of the elongate body, and the distal end of the malleable member may be fixedly attached to the distal end of the elongate body. In variations in which the malleable member may be disposed within a lumen of the elongate body, for example, the third lumen, the proximal end of the malleable member may be fixedly attached to the proximal end of the third lumen, and the distal end of the malleable member may be fixedly attached to the distal end of the third lumen. The malleable member may be attached to the elongate body using any suitable means, for example, adhesive, bonding, and the like. In some embodiments, the malleable member may be disposed in a lumen of the elongate body, but it may not be physically adhered to the lumen.

Figure 11A:
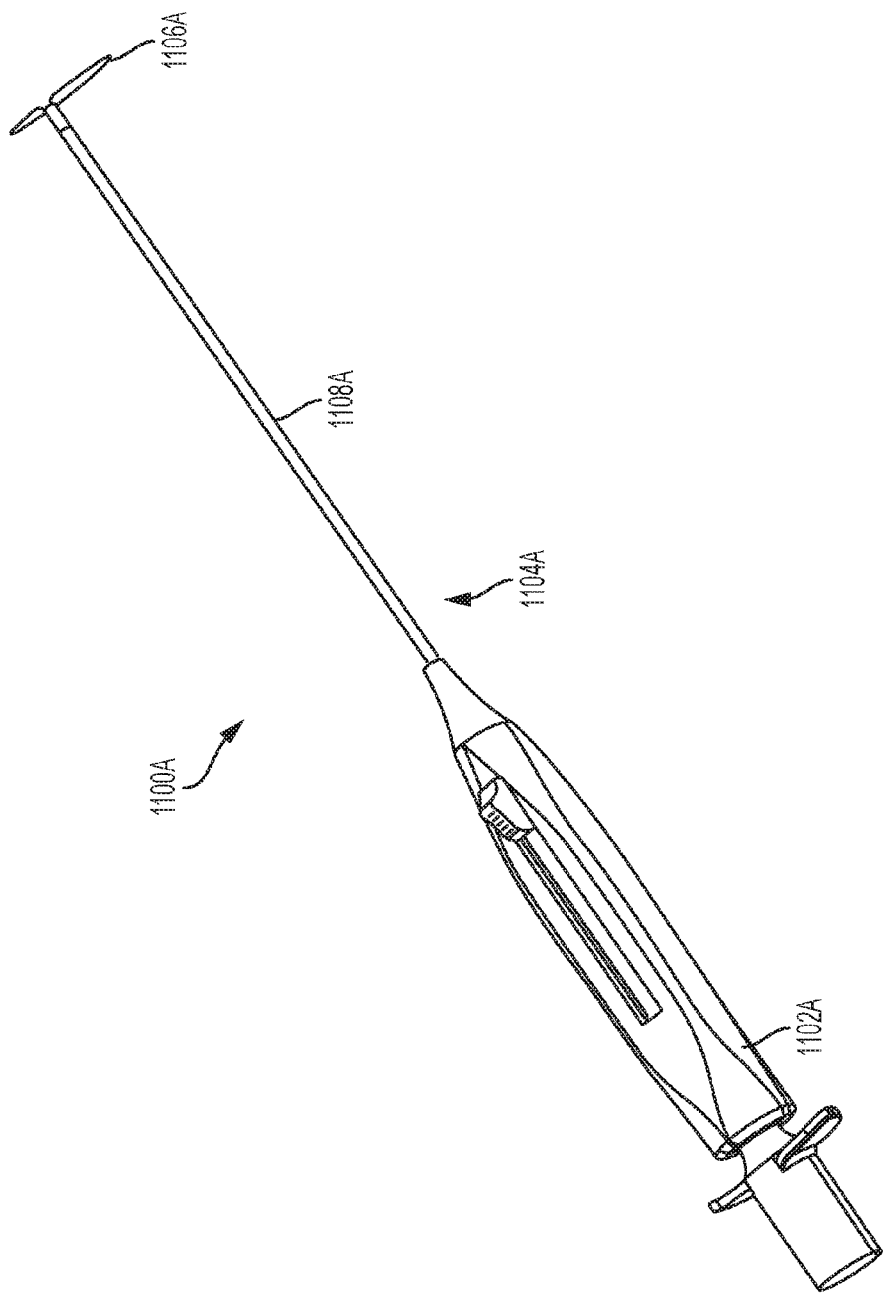

FIGS. 11A and 11B depict variations of a device (1100A, 1100B) for ligating tissue comprising a handle (1102A, 1102B), an elongate body (1104A, 1104B), a snare loop assembly (1106A, 1106B), and a malleable member (1108A, 1108B). FIG. 11C depicts a cross-sectional view of the elongate body (1104A) of the device (1100A) of FIG. 11A comprising a first lumen (1112), a second lumen (1114), a third lumen (1116), and a malleable member (1108A). In these variations, the malleable member (1108A, 1108B) is depicted in the form of a shapeable jacket. The shapeable jacket may surround the elongate body (1104A, 1104B) and may be coupled to an external surface of the elongate body (1104A, 1104B); however, the shapeable jacket may be disposed within and/or coupled to a lumen of the elongate body (1104, 1104B). The shapeable jacket may be coupled to the elongate body (1104A, 1104B) using any suitable means, including but not limited to, adhesive, epoxy and/or bonding, throughout the entire length of the shapeable jacket or on the proximal and/or distal ends of the shapeable jacket. The shapeable jacket may be fixedly attached to the elongate body (1104A, 1104B) such that the shapeable jacket cannot rotate or move longitudinally with respect to the elongate body (1104A, 1104B); however, it need not be. Moreover, the shapeable jacket may be made of any suitable malleable material, for example, stainless steel, shapeable polymers, and the like. In some variations, the shapeable jacket may be annealed. As depicted in FIG. 11B, in some variations, the malleable member (1108B) may comprise a cut pattern (1110B). The cut pattern (1110B) may vary along its length (e.g., in angle and pitch), as described above with respect to FIGS. 10A and 10B. In some variations, the thickness of the shapeable jacket may vary along the length of the shapeable jacket and therefore the length of the elongate body. For example, in some instances, the shapeable jacket may be thicker at its proximal end and thinner at its distal end. Varying the thickness of the shapeable jacket may provide the elongate body with more resistance to bending in locations where the shapeable jacket is thicker and less resistance to bending (i.e., it may be more flexible and easier to manipulate) in locations where the shapeable jacket is thinner. This may assist with the pushability and maneuverability of the closure device.

In some instances, the malleable member may comprise a shapeable wire disposed within a lumen of the elongate body (1104A, 1104B). The wire may be fixedly attached to the proximal and/or distal ends of the elongate body (1104A, 1104B), or the wire may be fixedly attached to the elongate body (1104A, 1104B) throughout its length. The wire may be made of any suitable malleable material, and in some instances, may be a stainless steel annealed wire. In some variations, the wire may be embedded within a wall of the elongate body (1104A, 1104B). In some embodiments, the device (1100A, 1100B) may comprise multiple malleable members. For example, the closure device may comprise both a shapeable jacket and a shapeable wire.

In some variations, the device may comprise a pull wire that may modify the curvature or shape of the malleable member and thus the elongate body. For example, in some embodiments, the closure device may comprise a pull wire and a shapeable jacket. The wire may be coupled to the distal end of the elongate body (1104A, 1104B) and to an actuator (e.g., a slider, knob, etc.) in the handle of the device. When the actuator is engaged, the pull wire may apply a force to the distal end of the elongate body to deflect it, curve the elongate body, and/or move it into a preferred shape. The actuator may then be disengaged, and the shapeable jacket or other malleable member may retain the curvature or shape, which may cause the elongate body to remain curved or shaped. The wire may have any suitable diameter and may be a round wire, a flat wire, or may comprise any suitable cross-sectional shape.

Visualization Tool

In some embodiments, the closure device may further comprise one or more visualization tools configured to allow a user to view the distal end of the elongate body, the snare loop assembly, and/or the tissue surrounding it during a procedure. The visualization tool may comprise any tool that may assist a user in viewing the end of the elongate body, the snare and/or snare loop assembly, and/or the surrounding tissue during a procedure. For example, in some embodiments, the visualization tool may comprise a scope (e.g., an endoscope), a light, a camera, or the like. The visualization tool may be a separate tool that is used with the closure device, or it may be part of the closure device itself. In embodiments in which the visualization tool is part of the closure device, the device may comprise a power source (e.g., batteries) for the visualization tool within its handle, or the visualization tool may be connectable to an external power source. The wires and/or other electronic components necessary to power the visualization tool, or otherwise enable the tool to function, and/or store images from the visualization tool, may be housed in any suitable location within the device. For example, the wires or other electronic components may be housed within a lumen of the elongate body or on or within the handle. In other variations, the electronic components may be external to the device and connected to the device at any suitable location. The visualization tool may be slideably disposed within any suitable lumen of the elongate body, or it may be fixedly attached to the lumen (e.g., at its proximal and/or distal end, in the center of the lumen, along a portion of the lumen, and the like) such that it will not move during a procedure. In some embodiments, the visualization tool may be coupled to an external surface of the elongate body, fixedly or releasably, using any suitable means (e.g., adhesive, bonding, snap fit elements, and the like).

Figure 12:
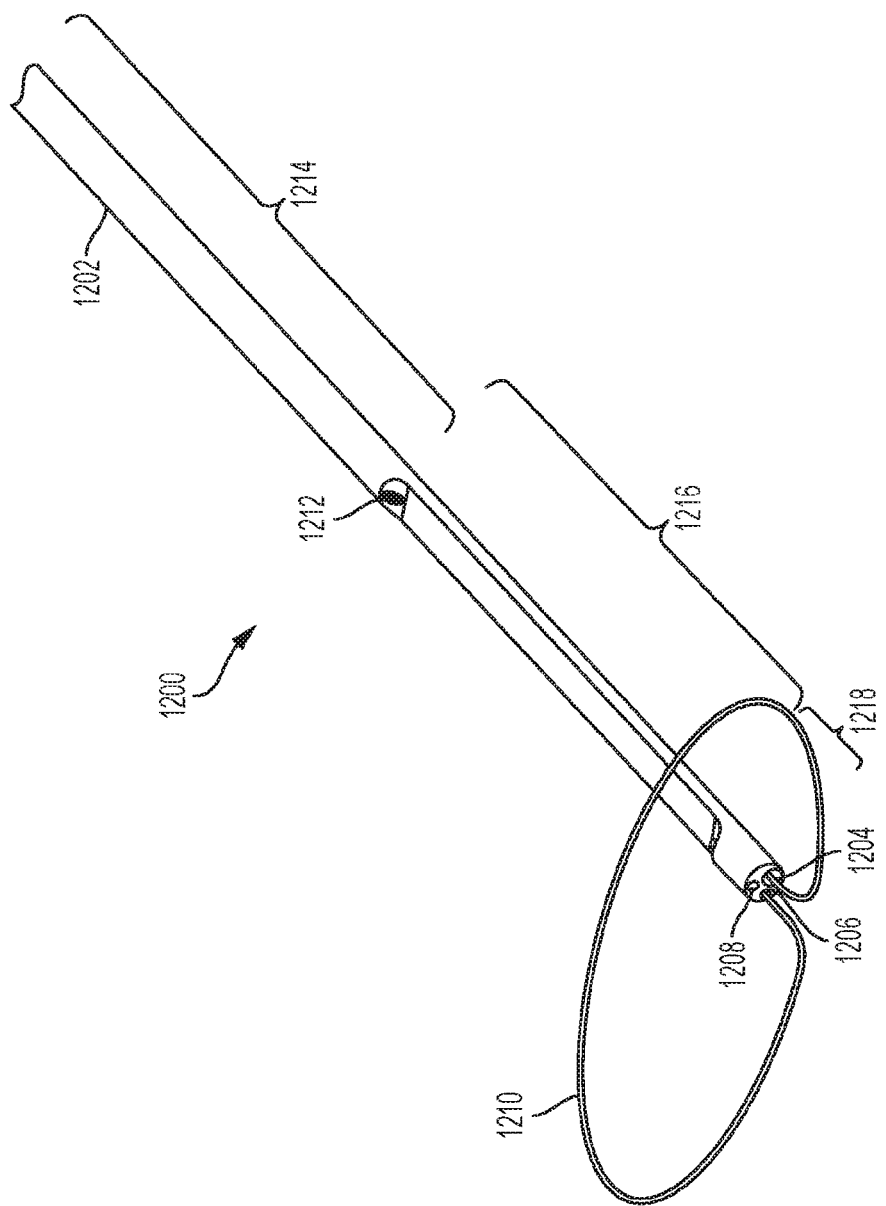
FIG. 12 provides an embodiment of the closure devices described here with a visualization tool.

FIG. 12 depicts a closure device (1200) comprising an elongate body (1202) having a first lumen (1204), a second lumen (1206), a third lumen (1208), a snare (1210), and a visualization tool (1212). While depicted with only the snare (1210), in some embodiments, the closure device (1200) may comprise a snare loop assembly, as described in more detail above. The elongate body may have any of the configurations previously described with respect to FIGS. 5A, 5B, 6A-6C, 7, 9, and 11A-11C (i.e., it may have any lumen configuration, multiple portions comprising different cross-sectional shapes and/or diameters, and/or it may have stiffened and flexible portions). As depicted here, the elongate body may comprise a first portion (1214) with a circular cross-sectional shape, a second portion (1216) with a D-shaped cross-sectional shape, and a third portion (1218) with a circular cross-sectional shape. The first and second lumens (1204, 1206) may house any component of the device as previously described, for example, portions of the snare and/or suture, while the third lumen (1208) may house the visualization tool (1212). In some of the previously described embodiments in which each of the lumens already comprises components of the device, an additional lumen may be added for the visualization tool, or the visualization tool may share a lumen with other components.

Turning back to FIG. 12, the lumen housing the visualization tool may comprise multiple entrances and exits, which may enable the use of the visualization tool in multiple locations along the elongate body. For example, here, a portion of the third lumen (1208) is cut-away in the second portion (1216) of the elongate body (1202), and thus the third lumen (1208) has an exit at the distal end of the first portion (1214) and at the distal tip of the device. The visualization tool (1212) may be used at either and/or both exits, or at any location between them. For example, in some instances, it may be beneficial for the visualization tool (1212) to exit the elongate body (1202) at the distal end of the first portion (1214) such that the visualization tool (1212) is proximally off-set from the distal tip of the elongate body (1202). In these instances, keeping the visualization tool (1212) at a location proximal to the distal tip of the elongate body (1202) may assist a user in viewing the closure element (1210), and the tissue surrounding it, during a procedure. In some instances, advancing the visualization tool (1212) to the distal tip of the elongate body (1202) may make it difficult to view the closure element (1210).

However, at times, it may be beneficial to advance the visualization tool (1212) to the distal tip of the device. For example, advancing the visualization tool (1212) to the distal tip of the elongate body (1202) may allow a user to view the tissue in front of the device and therefore may assist a user in steering and/or guiding the device through the body. In some instances, a user may employ the visualization tool (1212) in multiple locations during a procedure by sliding or otherwise moving (e.g., retracting and/or advancing) the visualization tool (1212). For example, a user may advance the visualization tool (1212) to the distal tip of the elongate body (1202) for use while the device is advanced through the body to the tissue to be ligated, and the user may then retract the visualization tool (1212) through a lumen of the elongate body (1202) to a location proximal of the distal tip (e.g., to any location in the second portion (2016) of the elongate body), for use while the tissue is ligated.

Figure 13A:
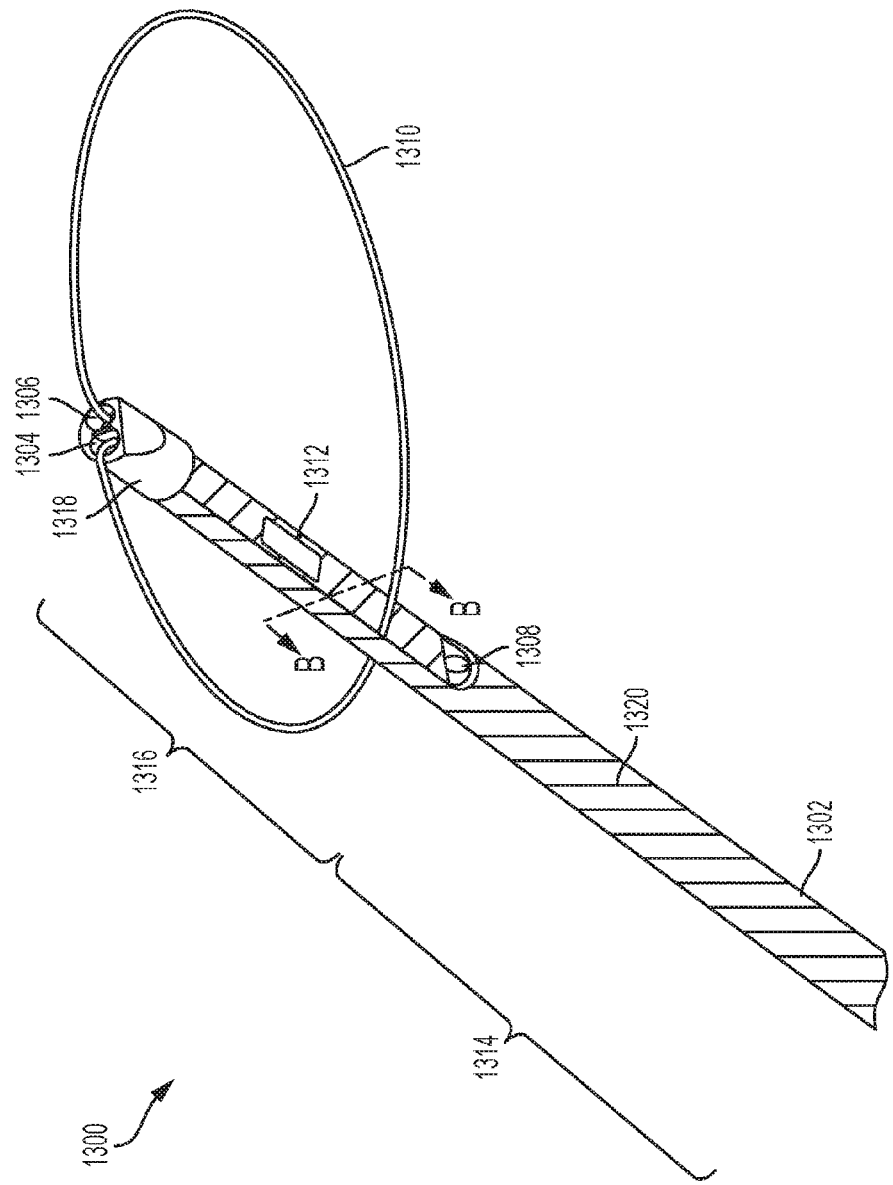
FIG. 13A is a perspective view of an embodiment of the closure devices described here with a visualization tool.
Figure 13B:
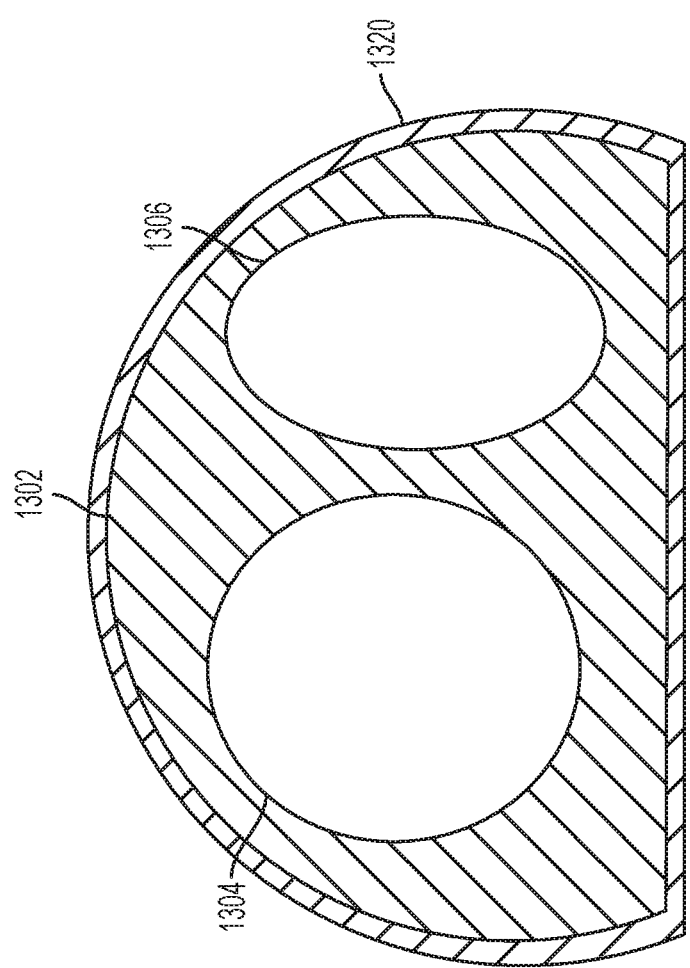
FIG. 13B is a cross-sectional view of a portion of the embodiment of the closure device shown in FIG. 13A.

FIG. 13A shows another embodiment of a closure device (1300) comprising an elongate body (1302) having a first lumen (1304), a second lumen (1306), a third lumen (1308), a snare (1310), and a visualization tool (1312). While depicted with only the snare (1310), in some embodiments, the closure device (1300) may comprise a snare loop assembly, as described in more detail above. FIG. 13B depicts a cross-sectional view of the elongate body (1302) of the closure device (1300) of FIG. 13A along line BB, but it should be appreciated that the elongate body need not have the depicted configuration and may instead have any of the configurations previously described with respect to FIGS. 5A-5B, 6A-6F, 7, 9, and 11A-11C (i.e., it may have any lumen configuration, multiple portions comprising different cross-sectional shapes and/or diameters, and/or it may have stiffened and flexible portions). Here, the elongate body (1302) may comprise a first portion (1314) with a circular cross-sectional shape, a second portion (1316) with a D-shaped cross-sectional shape distal to the first portion (1314) as depicted in FIG. 13B, and may have a tip (1318) on its distal end. The first, second, and third lumens (1304, 1306, 1308) may house any of the components as previously described, including a visualization tool as described with respect to FIG. 12 above. Additionally, the closure device (1300) shown here further comprises a jacket (1320), which may act as a stiffening element or a malleable member, as described in more detail above.

The closure device (1300) may comprise a visualization tool (1312) in the form of a camera mounted on an external surface of the second portion (1316) of the elongate body (1302), for example on the underside of the device, as depicted in FIG. 13A. The visualization tool (1312) here may assist a user in viewing the tissue surrounding the device during a procedure and may allow a user to capture still and moving images while a procedure is performed. The captured images may be analyzed during and/or after the procedure is completed. It should be appreciated that the visualization tool (1312) may be mounted on any suitable external surface of the elongate body (1302) and need not be on the underside of the device in the second portion (1316), as depicted. It should also be appreciated that mounting a visualization tool (1312) on an external surface of the elongate body (1302) may include mounting the visualization tool (1312) within a wall of the elongate body (1302) such that the visualization tool (1312) lays flush with the external surface of the elongate body (1302).

Moreover, in some variations, the visualization tool (1312) may be coupled to the tip (1318), which may assist a user in viewing the tissue in front of the device (1300), as described above. In some embodiments, the closure device (1300) may comprise multiple visualization tools (1312) (e.g., two, three, four, five, and the like). For example, the closure device (1300) may comprise multiple cameras, and/or the closure device (1300) may comprise a light disposed in a lumen of the elongate body and one or more cameras mounted on an external surface of the elongate body (1302).

Handle and Tensioning Mechanism

As described above, the closure devices described here may comprise a handle or other control mechanism. The handle may have any suitable shape or configuration, for example, any of those described in U.S. patent application Ser. No. 12/752,873, entitled "Tissue Ligation Devices and Controls Therefor" and filed on Apr. 1, 2010, which was previously incorporated by reference, or U.S. patent application Ser. No. 14/195,797, entitled "Tissue Ligation Devices and Methods Therefor" and filed Mar. 3, 2013, the contents of which are hereby incorporated by reference herein in their entirety.

The handle may serve many purposes. Of course, the handle may provide an interface between the device and the user as the user may hold onto and control the device and its components using the handle. The handle may be used to control and actuate the snare loop assembly through the elongate body, guide the elongate body, and/or modify the shape of the elongate body using a pull wire controlled through the handle. The handle may enable a user to control the release of the suture loop from the closure element, and it may be used to house electronic or other components for the visualization tool. The handle may comprise any suitable elements to facilitate use of the device for the closure of tissue, including sliders, knobs, switches, latches, push buttons, and the like, which may be coupled to any component of the snare loop assembly to pull, push, open, close, deploy, or otherwise use the component.

In some embodiments, the closure devices described here may comprise a tensioning mechanism for managing the tension applied to a portion of the suture loop (e.g., a tail of the suture loop) of the closure device. When the closure devices are used to place and tighten a suture loop around a tissue, it may be desirable to manage the tension applied to the suture as the suture loop is tightened. In some instances, it may be desirable to limit the maximum tension that is applied to a suture loop at different times during tightening. For example, if a sufficiently large tension is applied to the suture loop, the suture loop may cut through, shear off, or otherwise damage the ensnared tissue, and/or may break or damage one or more components of the closure device. Accordingly, it may be desirable for a user to know how much tension is applied to the tissue so that the user is able to control and modify the amount of applied force applied to appropriately close the ligated tissue without damaging it.

Figure 14:
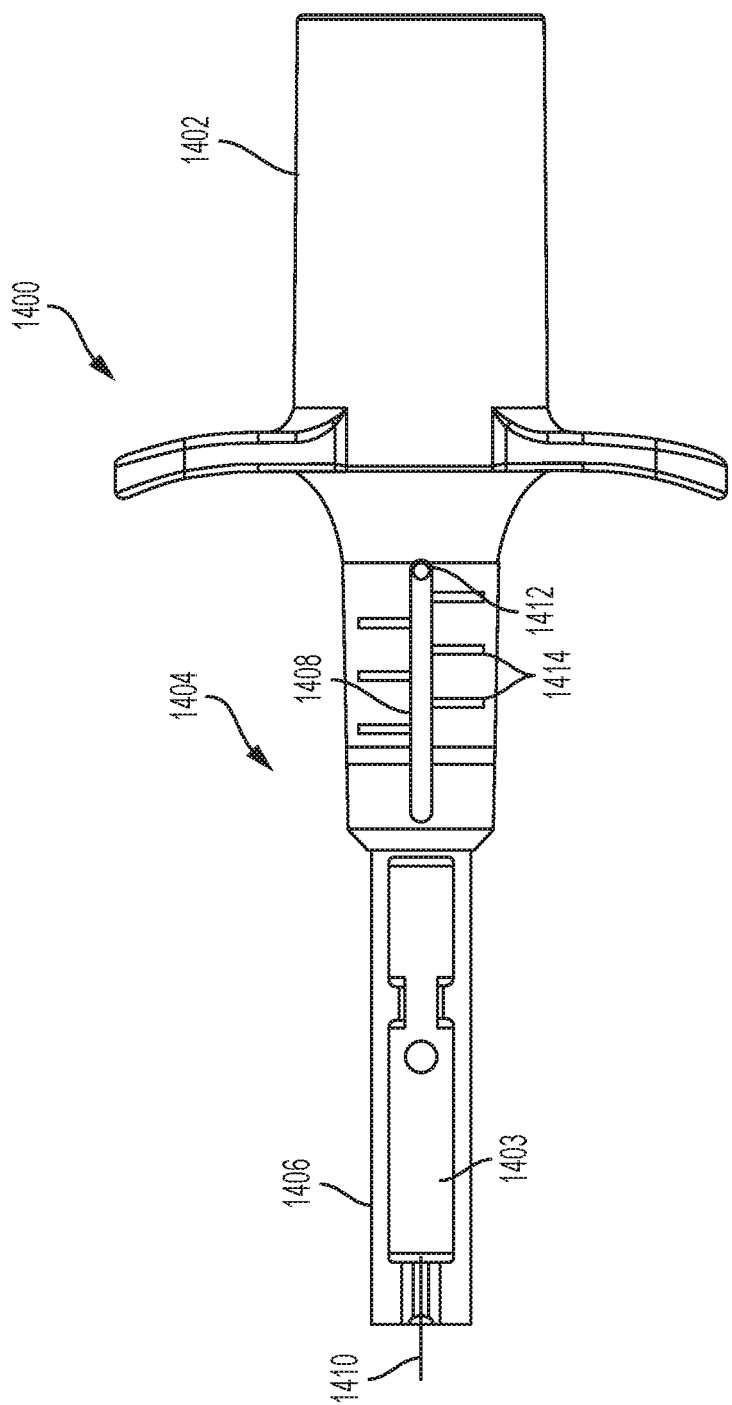
FIG. 14 depicts an embodiment of a tensioning mechanism.

In some variations, a tensioning device or mechanism may comprise a force gauge and may be used to provide a force measurement or other force indication to a user during tensioning of a suture loop. For example, FIG. 14 depicts a variation of a tensioning mechanism (1400) comprising a handle (1402) and a body (1404). It should be appreciated that the handle (1402) and the body (1404) of the tensioning mechanism (1400) may be integrally formed, or they may be formed separately and attached using any suitable means.

The body (1404) may comprise a suture attachment mechanism (1406) and a force indicator (1408). Generally, the suture attachment mechanism (1406) may grip, hold, or otherwise attach to a suture (1410) of a closure device (not shown). For example, in some variations, the suture attachment mechanism (1406) may grip, hold, or otherwise attach to a suture fob (1403), which may be fixedly attached to a tail of the suture (1410). In some instances, the suture attachment mechanism (1406) may comprise one or more lumens (e.g., two, three, etc.), and a tail of the suture (1410) (with or without a suture fob (1403)) may be fixedly attached to a lumen of the suture attachment mechanism (1406). A user may pull the handle (1402) of the tensioning mechanism (1400) away from the closure device to apply a tensile force to the suture (1410). The suture attachment mechanism (1406) may be attached to a force gauge (not shown) housed within the tensioning mechanism (1400), which may measure or otherwise provide an indication of the tension applied to the suture (1410) via the force indicator (1408). For example, the force indicator (1408) may comprise a pin (1412) and markers (1414) that may indicate the amount of force applied to the suture (1410).

Figure 15B:
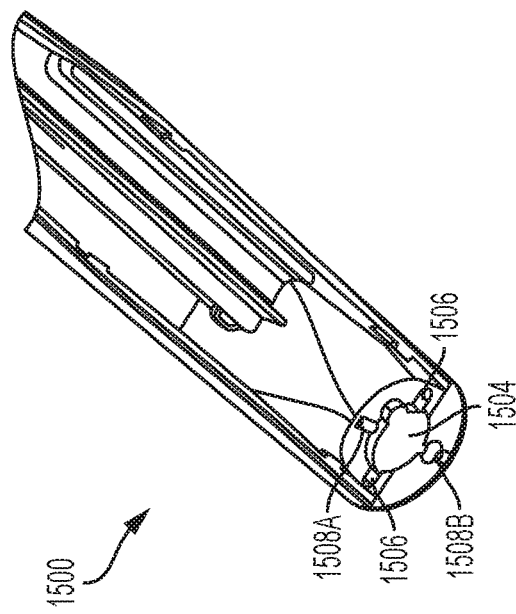
FIGS. 15A and 15B are perspective and cut-away views, respectively, of a portion of an embodiment of a handle of a closure device.
Figure 15A:
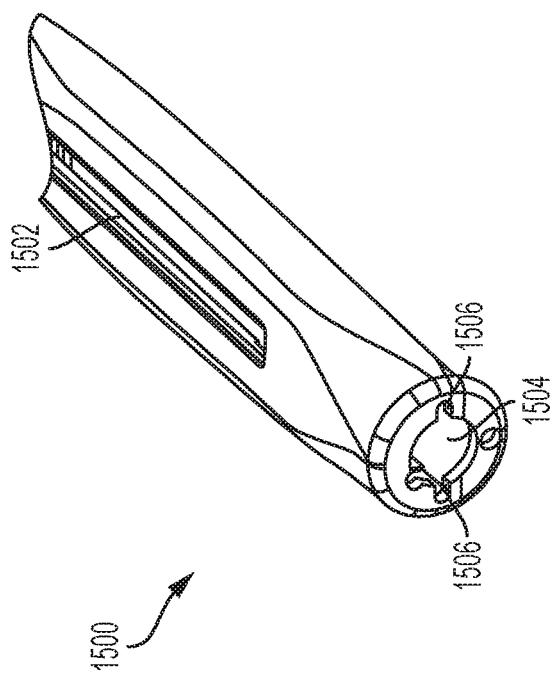
Figure 16B:
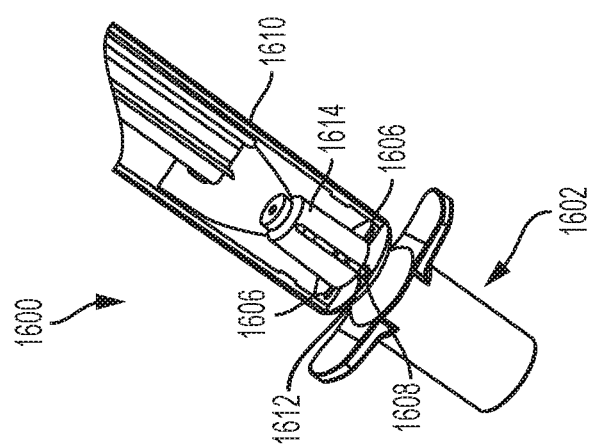
FIGS. 16A and 16B illustrate an embodiment of a closure device with a tensioning mechanism coupled to the handle.
Figure 16A:
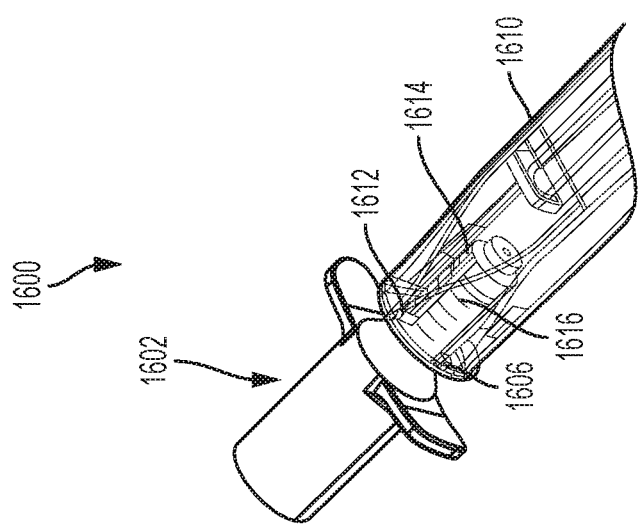

In some variations, the closure devices may be configured such that the tensioning mechanism may be releasably coupled to the handle of the device. For example, FIGS. 15A and 15B show a perspective view and a cut-away view respectively of a portion of an illustrative handle (1500) of the closure devices described here. As shown there, the handle (1500) may comprise a track (1502) for a slider (not shown) that may be used to control the closure element and/or the components of the snare loop assembly (not shown). The handle may also comprise an aperture (1504) in its proximal end configured to receive a tensioning mechanism. The handle may comprise release slot(s) (1506) extending from the aperture (1504) and at least one lock (1508A, 1508B). The release slot(s) (1506) may be configured to allow passage of the tensioning mechanism pin through the handle so that the body of the tensioning mechanism can be advanced into the handle (1500), as shown in FIGS. 16A and 16B. The tensioning mechanism may then be rotated such that the pin is placed within the lock (1508A, 1508B), thereby rotatably coupling the tensioning mechanism (1400) to the handle (1500). The lock (1508A, 1508B) may comprise any element configured to hold the pin of the tensioning mechanism, for example, an indentation, groove, aperture, hook, or the like. The lock (1508A, 1508B) may be located at any suitable angle with respect to a release slot (1506), for example, 10, 20, 30, 40, 50, 60, 70, 80, 90, 100, 110, 120, 130, 140, 150, 160, 170, 190, 200, 210, 220, 230, 240, 250, 260, 270, 280, 290, 300, 310, 320, 330, 340, or 350 degrees.

As depicted in FIG. 15B, in some variations, the handle (1500) may comprise a first lock (1508A) and a second lock (1508B). Here, each lock (1508A, 1508B) is in the form of a cylindrical indentation on an internal surface of the handle (1500). The first and second locks (1508A, 1508B) may be located 180 degrees from one another and 90 degrees from the release slots (1506). The pin of the tensioning mechanism may extend through the tensioning mechanism such that a first end of the pin rests in the first lock (1508A) and a second end of the pin rests in the second lock (1508B). While both locks are depicted as cylindrical indentations, it should be appreciated that the handle (1500) may comprise locks having different forms. Of course, the handle may comprise any suitable number of release slots and locks (e.g., one, two, three, four, or more) and need not comprise the same number of each.

As mentioned briefly above, FIGS. 16A and 16B depict a perspective view and a cut-away of a variation of the closure devices described here. In this embodiment, the closure device (1600) comprises a tensioning mechanism (1602) releasably coupled to the handle (1610). The body (1614) of the tensioning mechanism (1602) may be disposed within the handle (1610) of the closure device. The pin (1612) may extend through the body (1614) of the tensioning mechanism (1602) and radially outward such that it may rest in the lock (1608). In this way, the tensioning mechanism (1602) may be held in place within the handle (1610) and may be temporarily coupled to the handle (1610). A user may wish to keep the tensioning mechanism (1602) coupled to the handle (1610) during a procedure so that the tensioning mechanism (1602) is nearby and ready for use when the user wants to tighten the suture loop. Once the user is ready to tighten the suture loop, the user may rotate the tensioning mechanism (1602) such that the pin (1612) is removed from the lock (1608) and aligned with the release slot(s) (1606). The user may then pull the tensioning mechanism proximally such that the pin (1612) travels through the release slot(s) (1606) and the tensioning mechanism's body (1614) travels through the aperture in the handle (1610) of the closure device (1600), thereby removing the tensioning mechanism (1602) from the handle (1610). The user may then continue to pull the tensioning mechanism (1602) proximally relative to the handle (1610) until a desired amount of force is applied to the suture loop (not shown) and communicated to the user via the force indicator (1616).

II. Methods

The closure devices described here may be useful for closing tissue, for example, the left atrial appendage. The closure devices may access the left atrial appendage using percutaneous or surgical techniques, as described in more detail above. When percutaneous techniques are employed, the closure device may be used with a curved guide device to assist a user in inserting the closure device into a patient's body and accessing the desired portions of a patient's anatomy. In some instances, both the elongate body of the closure device and the guide device may be curved, and the curvature of the elongate body may or may not match the curvature of the guide device. When the curvatures of the elongate body and the guide device differ, in some instances, the elongate body may twist or otherwise rotate along its longitudinal axis when it is inserted into the guide device. This twisting may cause the elongate body's distal tip, and the closure element, to exit the guide device in a different orientation (e.g., at a different angle with respect to the top of the handle) than when it entered. When the elongate body twists or rotates within the guide device, the distal tip of the elongate body, and the closure element attached thereto, may also rotate. This may make it more difficult for a user to maneuver the device within the body and to ligate tissue.

Thus, it may be desirable for the elongate body to follow the curvature of the guide device without twisting or rotating within the guide device, regardless of whether the curvatures of the elongate body and guide device match when the elongate body is inserted into the guide device. This may allow the closure device to advance to the proper location within the body while the closure element is maintained in a user's desired orientation. Moreover, configuring the elongate body so that it does not twist or rotate within the guide device may allow the user to predict the orientation of the closure element once the closure element and the distal tip of the elongate body exit the guide device and properly place the closure element within the body. Furthermore, it may be desirable to be able to rotate the elongate body a predictable amount using the handle of the device, even when external forces (e.g., bending forces) are applied to the elongate body (e.g., from the curvature of the guide device, anatomy of the body, and the like).

The closure devices described here may be configured to be self-aligning or self-orienting when used with (e.g., inserted into or otherwise advanced along) a guide device. For example, a user may insert the elongate body into the guide device with the distal tip and closure element in any orientation, and the distal tip and closure element may exit the guide device in the same orientation (e.g., with the top of the handle and the orientation of the closure element aligned), regardless of whether the curvatures of the elongate body of the closure device and the guide device are aligned.

Figure 17C:
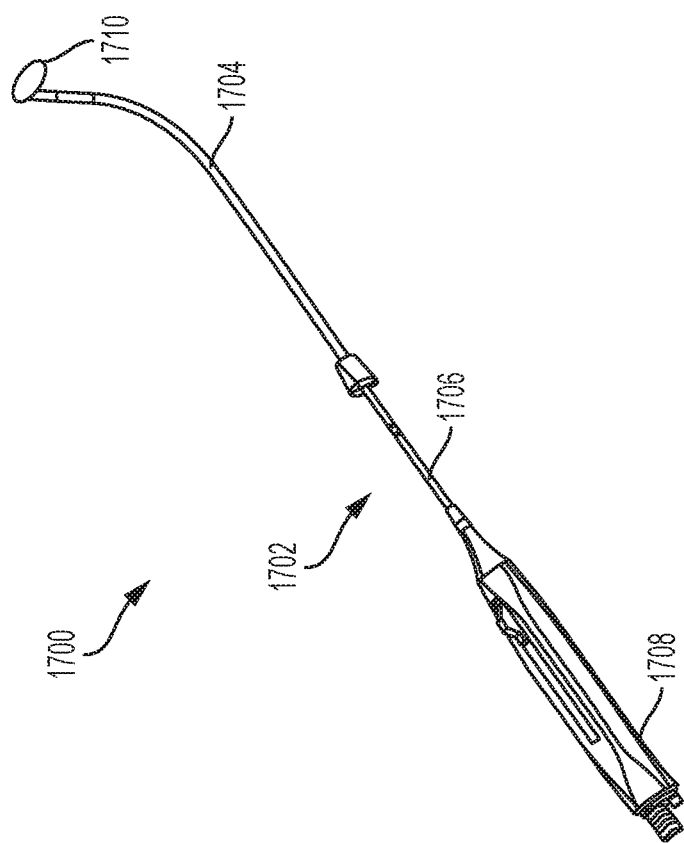

FIGS. 17A-17C may more clearly demonstrate this concept. FIGS. 17A-17C depict a system (1700) comprising a closure device (1702) in use with a guide device (1704). The closure device (1702) may be any of the closure devices described above and may comprise an elongate body (1706) with a curvature such that the distal tip of the elongate body (1706) is displaced toward the underside the handle (1708) when the elongate body is not subjected to any external force. It should be appreciated that the elongate body (1706) may have any suitable curvature and it need not be curved toward the underside of the handle (1708). Furthermore, as used herein, the top of the handle of the closure device generally refers to the surface of the handle comprising a control mechanism for the closure loop, and the underside of the handle generally refers to the surface opposite the top of the handle. In some embodiments, the control mechanism for the closure loop may be located on a side of the handle, in which case, the top of the handle refers to the portion of the handle facing upwards when a user is holding the handle as instructed to begin a procedure.

The guide device (1704) may comprise any device used to direct the distal tip of the elongate body to a specified or desired location within a patient's body, for example, a guide cannula, a trocar, a guide rail, percutaneous tubing, and the like. The guide device (1704) may have a curvature along its length and may comprise a lumen configured to receive the elongate body (1706) of the closure device (1702). To begin a procedure, a user may insert the elongate body (1706) into a lumen of the guide device (1704), and the guide device may steer or otherwise direct the distal tip of the elongate body (1706) to a desired location in the body.

FIGS. 17A and 17C depict configurations of the closure devices described here in which the elongate body is configured to resist twisting. In contrast, FIG. 17B depicts a closure device in which the elongate body is not configured to resist twisting, and has in fact twisted within the guide device. In FIG. 17A, the closure device (1702) has been inserted into the guide device (1704) with the pre-insertion curvature of the elongate body (1706) matching the curvature of the guide device (1704) (e.g., both the distal ends of the elongate body (1706) and the guide device (1704) are curved in the same direction, i.e., toward the underside of the handle (1708)). As shown there, the closure element or loop (1710) has the same orientation with respect to the handle (1708) both before and after it is inserted into the guide device. In some instances, the orientation of the closure loop (1710) depicted in FIG. 17A may be the preferred orientation for the closure loop (1710); however, this need not be the case. For example, in some instances, the closure loop may have a different orientation.

In FIG. 17C, the closure device (1702) has been inserted into the guide device (1704) with the pre-insertion curvature of the elongate body (1706) facing the opposite, or a different, direction than the curvature of the guide device (1704) (e.g., the distal tip of the elongate body (1706) is curved toward the underside of the handle while the distal tip of the guide device (1704) is curved toward the top of the handle (1708)). Despite the misalignment of the curvatures of the elongate body (1704) and the guide device (1706), the closure loop (1710) has remained in the same orientation with respect to the handle (1708).

In contrast, in FIG. 17B, the closure device (1702) has been inserted into the guide device (1704) with the pre-insertion curvature of the elongate body (1706) facing an opposite, or a different, direction than the curvature of the guide device (1704). However here, the elongate body (1706) has twisted inside the guide device (1704) causing the closure loop (1710) to rotate with respect to the handle (1708). The configuration depicted in FIG. 17B may be undesirable in some instances because the twist in the elongate body may make it more difficult to steer the device through the body, control the location of the distal tip, deploy the closure loop, and, in embodiments with a suture loop, deploy the suture loop.

As depicted in FIGS. 17A and 17B and described above, the closure loop (1710) may comprise a first configuration in which the closure loop (1710) and the handle (1708) are aligned, and a second configuration in which the closure loop (1710) and the handle (1708) are misaligned. The closure loop (1710) and the handle (1708) may be aligned when the closure loop (1710) is in the proper configuration to begin a procedure when the handle faces up. The closure loop (1710) and the handle (1708) are misaligned when the closure loop (1710) is rotated with respect to the top of the handle (1708) such that the closure loop (1710) is rotationally offset from its proper configuration when the top of the handle is facing up.

The closure device (1702) and the guide device (1704) may comprise a delivery configuration in which the curvatures of the elongate body (1706) of the closure device (1702) and the guide device (1704) are misaligned (i.e., their curves have different orientations). In some variations, the closure device (1702) may be configured to remain in the first configuration (i.e., with the closure loop and the handle aligned), when the closure device (1702) and the guide device (1704) are in the delivery configuration (e.g., when they are curved in different directions). In this way, the closure device (1702) and the guide device (1704) may be configured to be self-orienting or self-aligning.

III. Systems

Described here are systems for closing tissue, for example, a left atrial appendage. In general, the systems may comprise a closure device useful for performing a left atrial appendage closure procedure, together with one or more additional components. For example, the system may comprise a curved guide device comprising a lumen therethrough. The lumen may be sized and configured to receive an elongate body of a closure device described here. In some embodiments, the system may comprise a first guide wire having a size and length adapted for accessing the left atrial appendage through the vasculature and comprising an alignment member, a second guide wire having a size and a length adapted for accessing the pericardial space from a subthoracic region and comprising an alignment member, and a closure device. The alignment member may be any suitable alignment member. For example, the alignment member may comprise radiopaque or echogenic markers, members configured to produce an audible response, one or more interconnecting members, one or more vacuum members, or magnets.

The closure device may be any of the closure devices described above. For example, the closure device may be one comprising an elongate body with a first stiffened portion and a second flexible portion, and a closure element comprising a loop. The system may further comprise an expandable member or a device comprising an expandable member. The expandable member may be any suitable expandable member, such as, for example, a balloon catheter. The expandable member may have one or more apertures therein for allowing contrast or other fluids to pass therethrough. The system may further comprise a suture loop, and the suture loop may or may not be coupled or coupleable to the closure device. Of course, the system may comprise instructions for using any, all, or a portion of the system's components (e.g., guide device, first guide wire, second guide wire, closure device, or some combination thereof).

Although the foregoing invention has, for the purposes of clarity and understanding, been described in some detail by of illustration and example, it will be apparent that certain changes and modifications may be practiced, and are intended to fall within the scope of the appended claims. Additionally, it should be understood that the components and characteristics of the devices described herein may be used in any combination. The description of certain elements or characteristics with respect to a specific figure are not intended to be limiting or nor should they be interpreted to suggest that the element cannot be used in combination with any of the other described elements.

What is claimed is:

1. A surgical device for closing the left atrial appendage comprising:
    an elongate body comprising a first lumen, a second lumen, and a third lumen;
    a closure element comprising a loop defining a continuous aperture therethrough, a first end of the closure element slideably disposed in the first lumen and a second end of the closure element fixedly disposed in the second lumen;
    a suture loop;
    a malleable member fixedly attached to the elongate body, wherein the malleable member is configured to retain a curve after a force is applied, and wherein applying a force to the malleable member modifies a curvature of the elongate body;
    a handle; and
    a tensioning mechanism, wherein the tensioning mechanism is releasably coupled to the handle and is configured to close the suture loop around tissue after it is released from the handle.

2. The device of claim 1 wherein the malleable member is disposed in the third lumen.

3. The device of claim 2 wherein the malleable member comprises a first end and a second end, and wherein the first end is fixedly attached to a proximal end of the third lumen and the second end is fixedly attached to a distal end of the third lumen.

4. The device of claim 3 wherein the malleable member comprises an annealed stainless steel wire.

5. The device of claim 1 wherein the malleable member comprises a jacket around the elongate body.

6. The device of claim 5 wherein the jacket is annealed stainless steel.

7. The device of claim 6 wherein the jacket comprises a spiral cut pattern.

8. The device of claim 1 wherein the tensioning mechanism is rotatably coupled to the handle.

9. The device of claim 1 wherein the tensioning mechanism locks into the handle.

10. The device of claim 1 further comprising at least one of a scope, a light, or a camera.

11. The device of claim 1 wherein the device is configured to close a left atrial appendage during an open surgical procedure.

12. The device of claim 11 wherein the open surgical procedure is a median sternotomy, mini sternotomy, thoracotomy, or a thoracoscopy.

13. A surgical device for closing the left atrial appendage comprising:

an elongate body comprising a first lumen, a second lumen, and a third lumen;

a closure element comprising a loop defining a continuous aperture therethrough, a first end of the closure element slideably disposed in the first lumen and a second end of the closure element fixedly disposed in the second lumen; and a malleable member fixedly attached to the elongate body and comprising a jacket around the elongate body, wherein the malleable member is configured to retain a curve after a force is applied, and wherein applying a force to the malleable member modifies a curvature of the elongate body; and a pull wire disposed in the third lumen, wherein the pull wire is configured to deflect a distal end of the elongate body.

14. The device of claim 13 wherein the jacket is annealed stainless steel.

15. The device of claim 14 wherein the jacket comprises a spiral cut pattern.

* * * * *